United States Patent [19]

Togano et al.

[11] Patent Number: 5,116,530

[45] Date of Patent: May 26, 1992

[54] MESOMORPHIC COMPOUND, LIQUID CRYSTAL COMPOSITION CONTAINING SAME AND LIQUID CRYSTAL DEVICE USING SAME

[75] Inventors: Takeshi Togano, Yokohama; Takao Takiguchi, Tokyo; Yoko Yamada, Atsugi; Masanobu Asaoka, Yokohama; Kenji Shinjo, Atsugi, all of Japan

[73] Assignee: Canon Kabushiki Kaisha, Tokyo, Japan

[21] Appl. No.: 421,948

[22] Filed: Oct. 16, 1989

[30] Foreign Application Priority Data

Oct. 17, 1988 [JP] Japan ................ 63-262516

[51] Int. Cl.$^5$ .......... C09K 19/34; C09K 19/32; C09K 19/12; C07D 333/02
[52] U.S. Cl. .......... 252/299.61; 252/299.66; 252/299.62; 549/1; 549/29; 549/59
[58] Field of Search ........ 252/299.01, 299.61, 252/299.63, 299.66, 299.67, 299.62; 544/242, 245, 299, 294, 333; 548/126, 136, 143; 549/41, 43

[56] References Cited

U.S. PATENT DOCUMENTS

| | | | |
|---|---|---|---|
| 3,478,020 | 11/1969 | Zienty et al. | 549/59 |
| 3,549,624 | 12/1970 | Conover et al. | 260/240 |
| 4,128,314 | 12/1978 | Sevostiyanov et al. | 350/341 |
| 4,137,235 | 1/1979 | Irick, Jr. et al. | 260/307 R |
| 4,367,924 | 1/1983 | Clark et al. | 350/334 |
| 4,480,104 | 10/1984 | Postle et al. | 549/71 |
| 4,812,259 | 3/1989 | Yoshinaga et al. | 252/299.65 |
| 4,816,178 | 3/1989 | Katagiri et al. | 252/299.6 |
| 4,874,544 | 10/1989 | Yong et al. | 252/299.61 |
| 4,876,027 | 10/1989 | Yoshinaga et al. | 252/299.65 |
| 4,880,560 | 11/1989 | Yoshinaga et al. | 252/299.01 |
| 4,882,085 | 11/1989 | Yoshinaga et al. | 252/299.61 |
| 4,904,410 | 2/1990 | Nohira et al. | 252/299.61 |
| 4,952,699 | 8/1990 | Yong et al. | 548/136 |

FOREIGN PATENT DOCUMENTS

| | | |
|---|---|---|
| 263054 A1 | 7/1987 | German Democratic Rep. ........ 548/136 |
| 56-107216 | 8/1981 | Japan . |
| 59-193426 | 11/1984 | Japan . |
| 59-193427 | 11/1984 | Japan . |
| 60-156046 | 8/1985 | Japan . |
| 60-156047 | 8/1985 | Japan . |
| 1028152 | 5/1966 | United Kingdom ........ 260/240 |
| 2143541 | 7/1983 | United Kingdom ........ 548/136 |

OTHER PUBLICATIONS

H. Schadt and W. Halfrich, *Voltage-Dependent Optical Activity of a Twisted Nematic Liquid Crystal*, Applied Physics Letters, vol. 18, No. 4, (Feb. 15, 1971) pp. 127-128.

*Primary Examiner*—Robert L. Stoll
*Assistant Examiner*—Cynthia Harris
*Attorney, Agent, or Firm*—Fitzpatrick, Cella, Harper & Scinto

[57] ABSTRACT

A mesomorphic compound represented by the following formula (I):

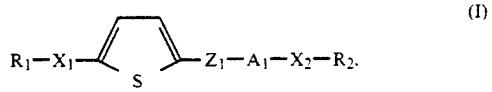

wherein $R_1$ and $R_2$ respectively denote a linear or branched alkyl group having 1-18 carbon atoms capable of having a substituent; $X_1$ denotes any one of a single bond, —O—,

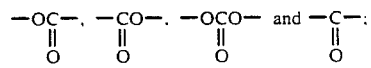

$X_2$ denotes any one of a single bond, —O—, $Z_1$ denotes any one of
—CH$_2$O— and —CH=C(CN)—; and $A_1$ denotes —$A_2$— or —$A_2$—$A_3$— wherein $A_2$ and $A_3$ respectively denote any one of
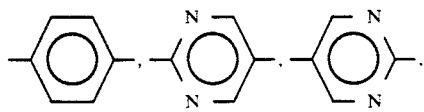
-continued
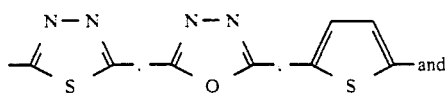
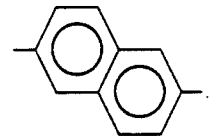
8 Claims, 2 Drawing Sheets

MESOMORPHIC COMPOUND, LIQUID CRYSTAL COMPOSITION CONTAINING SAME AND LIQUID CRYSTAL DEVICE USING SAME

FIELD OF THE INVENTION AND RELATED ART

The present invention relates to a novel mesomorphic compound, a liquid crystal composition containing the compound and liquid crystal device using the composition, and more particularly to a novel liquid crystal composition with improved responsiveness to an electric field and a liquid crystal device using the liquid crystal composition for use in a liquid crystal display apparatus, a liquid crystal-optical shutter, etc.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of milli-seconds, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected or regions where a scanning electrode is not selected and a signal electrode is selected (which regions are so called "half-selected points"). If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. As a result, this leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed. However, any method is not sufficient to overcome the above-mentioned drawbacks. As a result, it is the present state that the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216, U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, ferroelectric liquid crystal materials developed heretofore cannot be said to satisfy sufficient characteristics required for a liquid crystal device including low-temperature operation characteristic, high-speed responsiveness, etc. Among a response time $\tau$, the magnitude of spontaneous polarization Ps and viscosity $\kappa$, the following relationship exists: $\tau = \kappa/(Ps \cdot E)$, where E is an applied voltage. Accordingly, a high response speed can be obtained by (a) increasing the spontaneous polarization Ps, (b) lowering the viscosity $\kappa$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Further, if it is assumed that the operation temperature of an actual display device is 5°-40° C., the response speed changes by a factor of about 20, so that it actually exceeds the range controllable by driving voltage and frequency.

As described hereinabove, commercialization of a ferroelectric liquid crystal device requires a ferroelectric chiral smectic liquid crystal composition having a low viscosity, a high-speed responsiveness and a small temperature-dependence of response speed.

SUMMARY OF THE INVENTION

An object of the present invention is to provide a mesomorphic compound, a liquid crystal composition, particularly a ferroelectric chiral smectic liquid crystal composition, containing the mesomorphic compound for providing a practical ferroelectric liquid crystal device, and a liquid crystal device using the liquid crystal composition and having a high response speed and a smaller temperature-dependence of the response speed.

Accordingly to the present invention, there is provided a mesomorphic compound represented by the following formula (I):

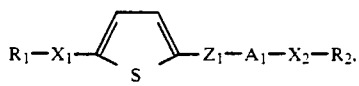

wherein $R_1$ and $R_2$ respectively denote a linear or branched alkyl group having 1-18 carbon atoms capable of having a substituent; $X_1$ denotes any one of a single bond, —O—,

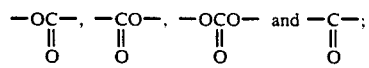

$X_2$ denotes any one of a single bond, —O—,

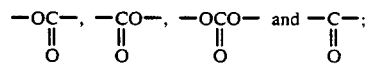

$Z_1$ denotes any one of

—CH$_2$O— and —CH=C(CN)—; and
$A_1$ denotes —$A_2$— or —$A_2$—$A_3$— wherein $A_2$ and $A_3$ respectively denote any one of

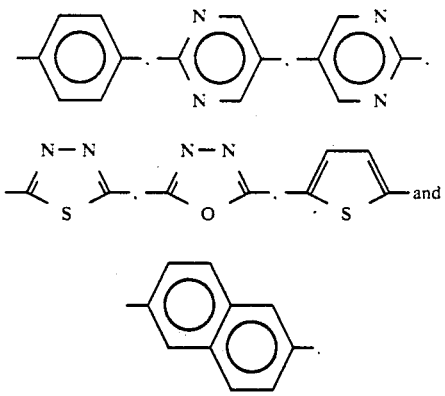

According to the present invention, there is further provided a ferroelectric chiral smectic liquid crystal composition containing at least one species of the mesomorphic compound as described above.

The present invention further provides a liquid crystal device comprising a pair of substrates and such a ferroelectric liquid crystal composition as described above disposed between the electrode plates.

These and other objects, features and advantages of the present invention will become more apparent upon a consideration of the following description of the preferred embodiments of the present invention taken in conjunction with the accompanying drawings.

DETAILED DESCRIPTION OF THE INVENTION

Figure 1:
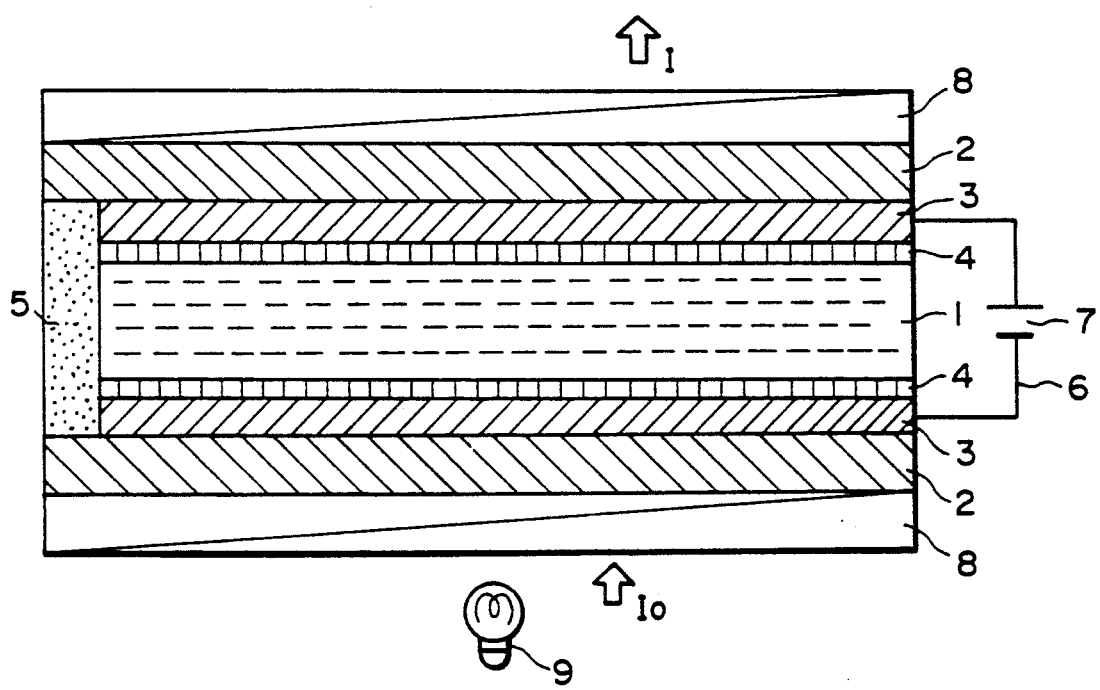
FIG. 1 is a schematic sectional view of a liquid crystal display device using a ferroelectric liquid crystal.

In the formula (I) as described above, preferred examples of $X_1$, $X_2$ and $Z_1$ may respectively include the following combinations:

$X_1$ is a single bond, —O—, or

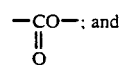

$X_2$ is a single bond, —O—,

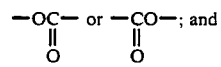

$Z_1$ is

or —CH$_2$O—, particularly

Further, preferred examples of $R_1$ and $R_2$ in the formula (I) may include the following groups (i) to (iv):

(i) n-alkyl group having 1-18 carbon atoms, particularly having 3-14 carbon atoms;

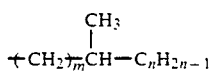 (ii)

wherein m is 0-7 and n is 2-9 (optically active or inactive);

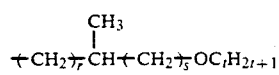 (iii)

wherein r is 0-7, s is 0 or 1 and t is 1-14 (optically active or inactive); and

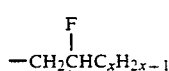 (iv)

wherein x is 1-16. Herein * denotes an optically active center. Still further, in the formula (I), $A_1$ may include the following combinations:

Case where $A_1$ is $-A_2-$ $-A_2-$ may preferably be

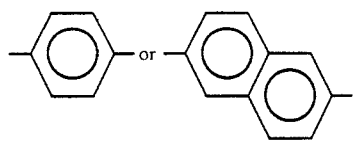

and $X_2$ may preferably be a single bond, $-O-$,

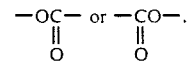

further preferably be a single bond or $-O-$; and

Case where $A_1$ is $-A_2-A_3-$ $-A_2-A_3-$ may preferably be

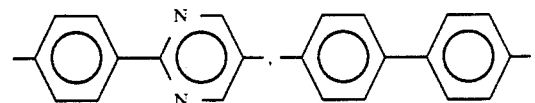

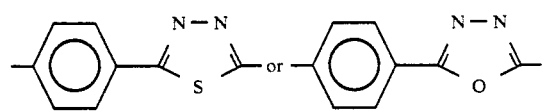

and $X_2$ may preferably be a single bond, $-O-$,

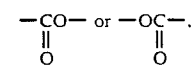

further preferably be a single bond.

The mesomorphic compounds represented by the general formula (I) may be sythesized through the following reaction schemes.

(Case where $X_1$ is a single bond or $-\underset{\underset{O}{\|}}{C}-$)

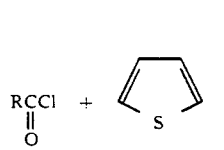

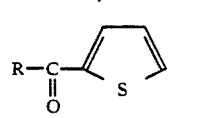 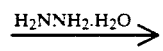 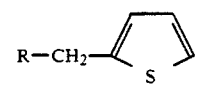

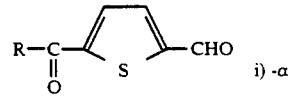

  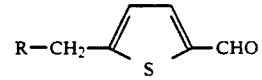

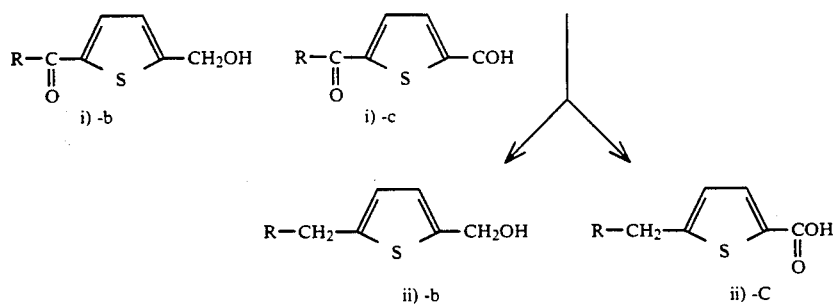
In the above, R denotes a linear or branched alkyl group.
In the above, R denotes a linear or branched alkyl group and $Z_2$ denotes —CH$_2$OH, —COOH or —CHO.
(Case where $X_1$ is —O—, —CO— or —OCO)
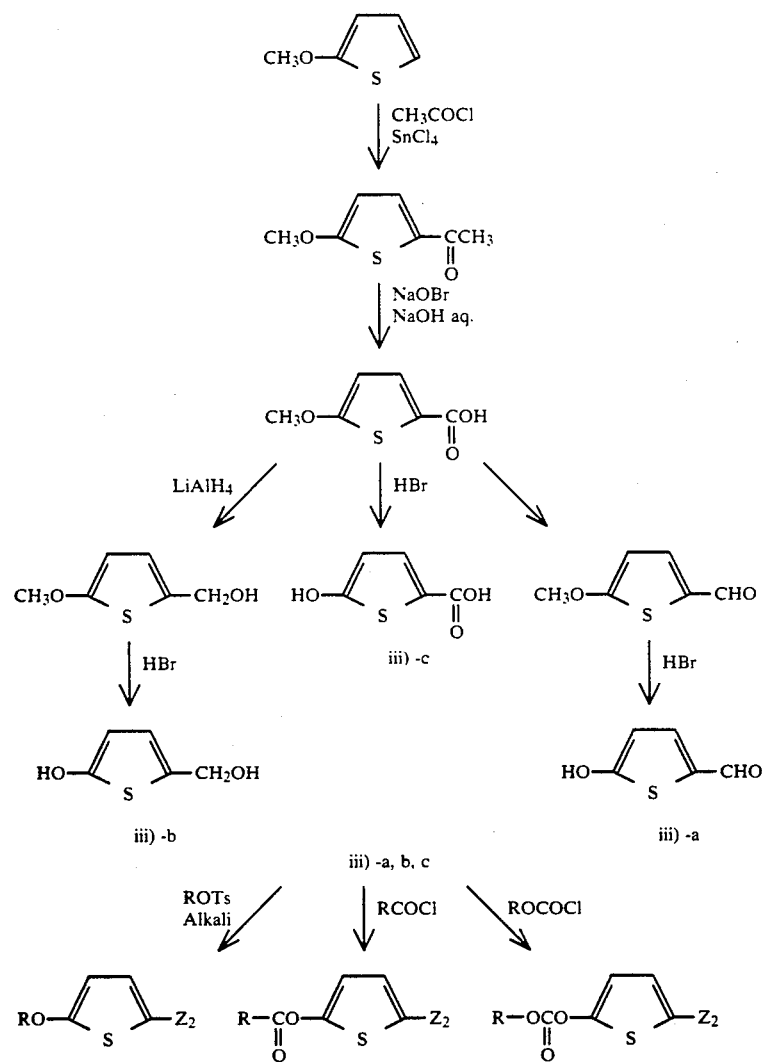
(Case where $X_1$ is —OC—)

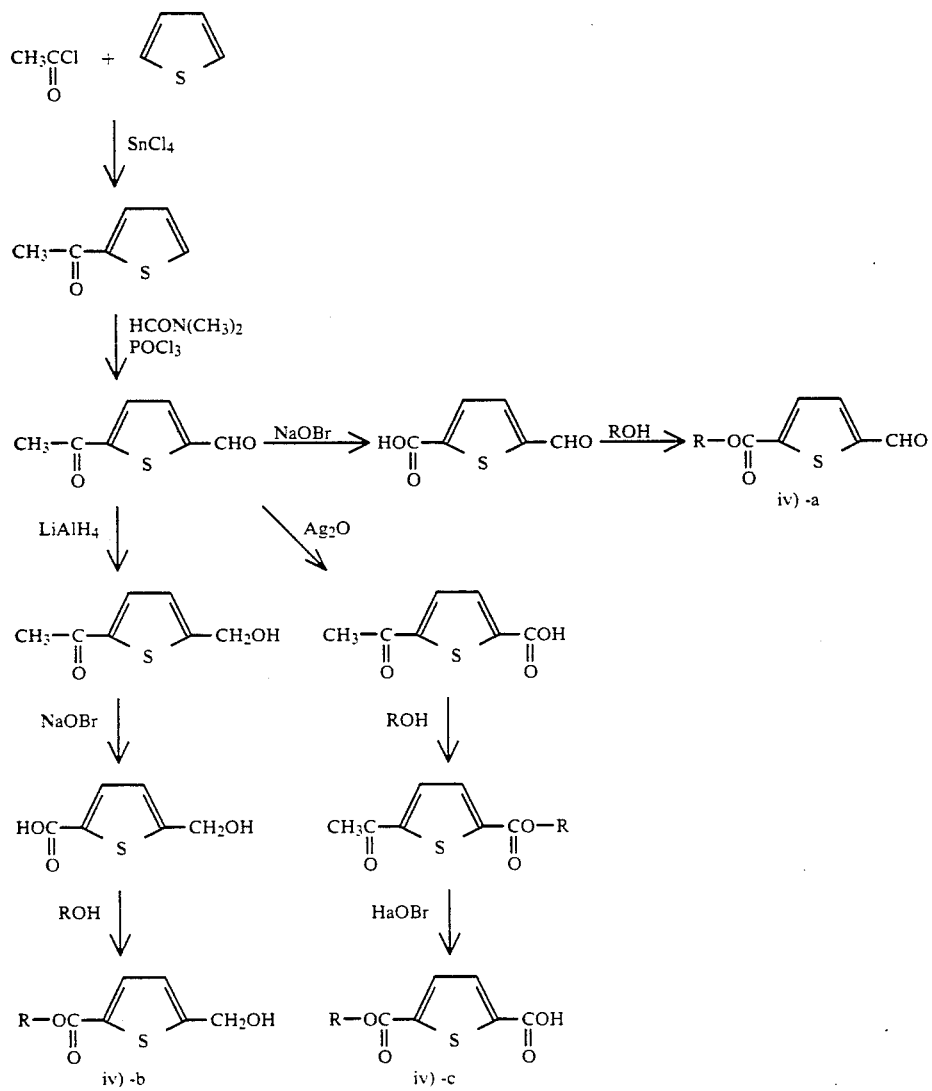
In the above, R denotes a linear or branched alkyl group.
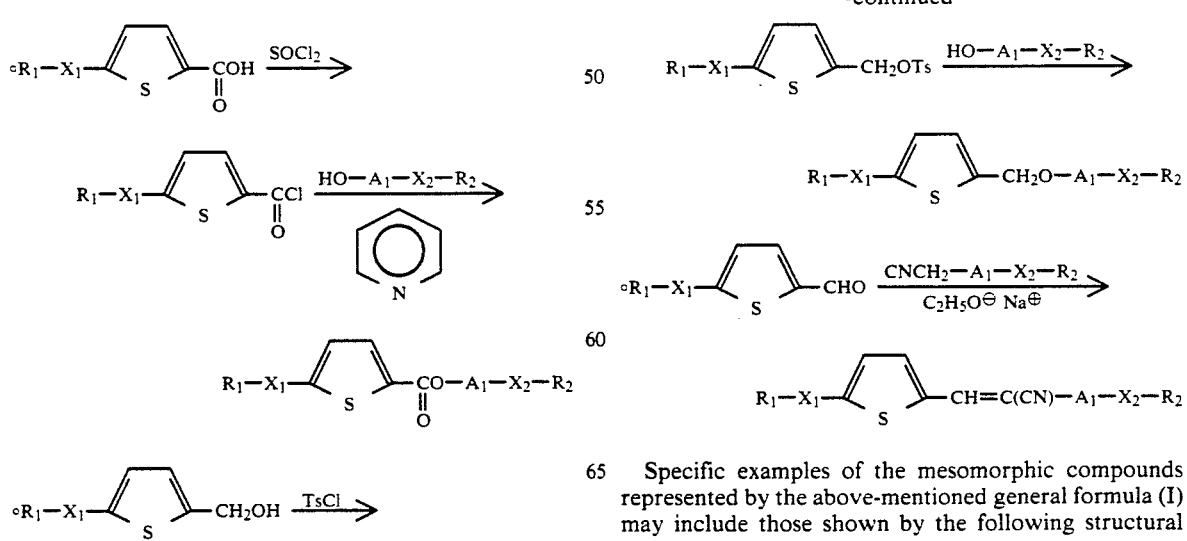
Specific examples of the mesomorphic compounds represented by the above-mentioned general formula (I) may include those shown by the following structural formulas.

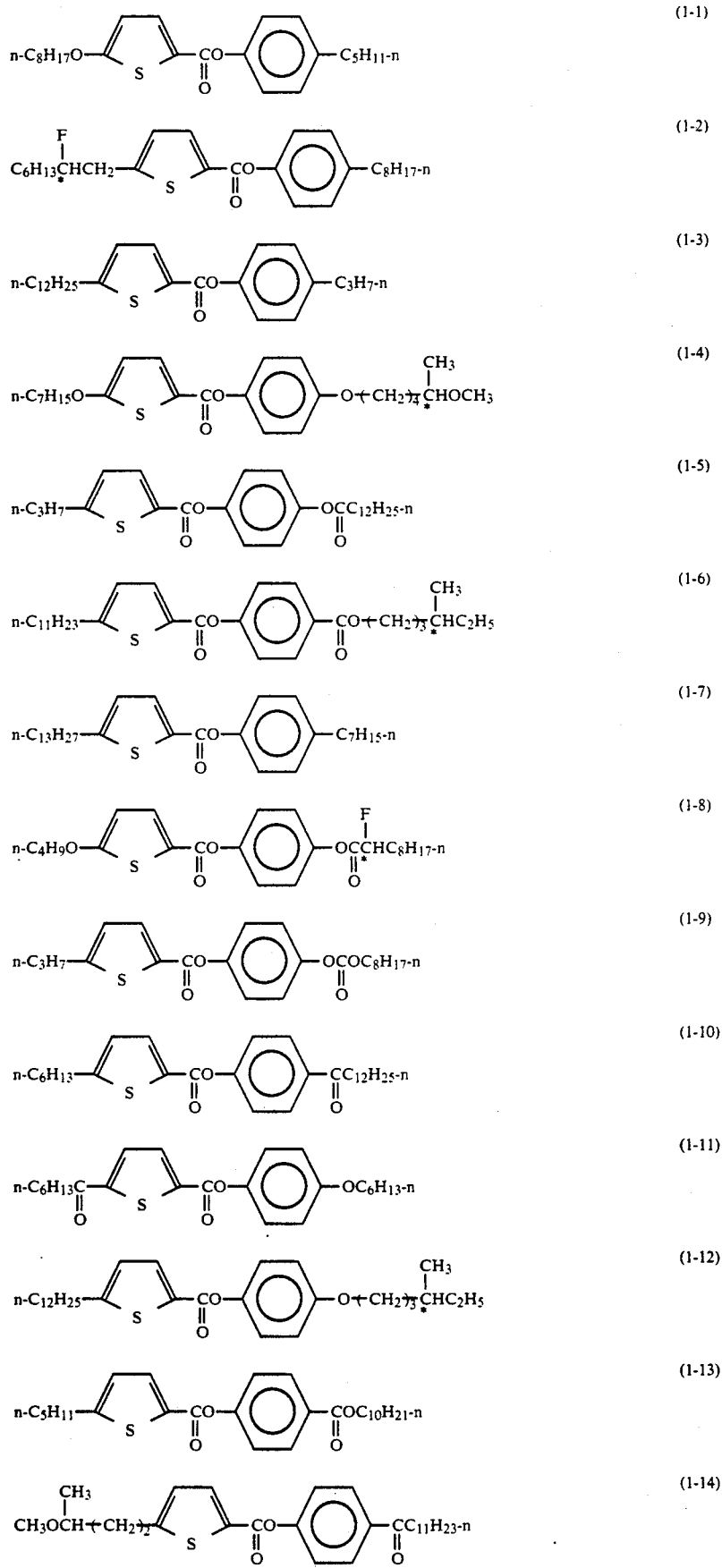

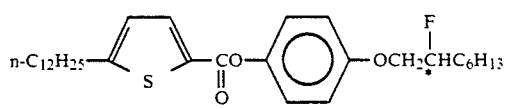 (1-15)
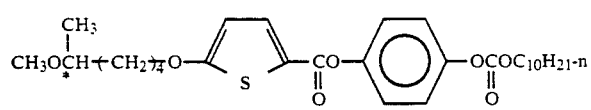 (1-16)
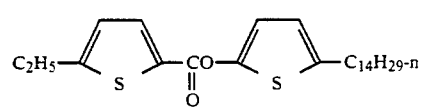 (1-17)
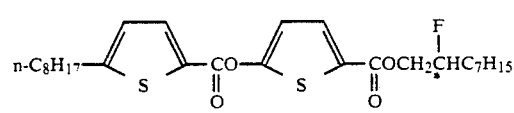 (1-18)
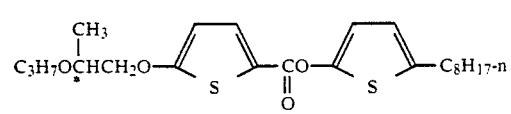 (1-19)
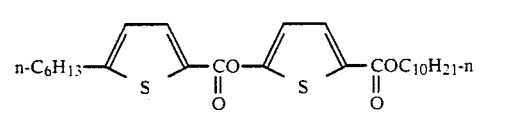 (1-20)
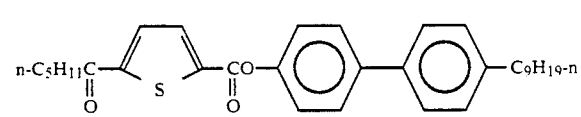 (1-21)
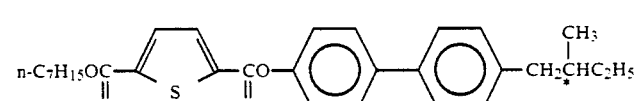 (1-22)
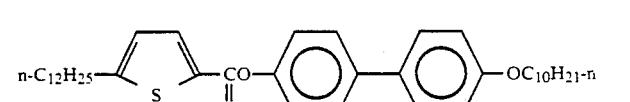 (1-23)
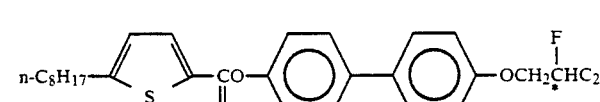 (1-24)
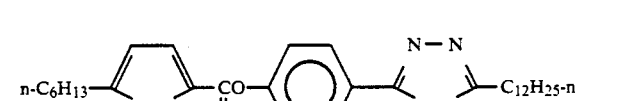 (1-25)
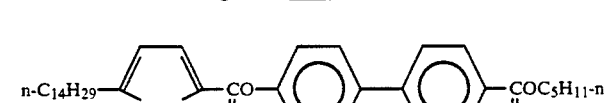 (1-26)
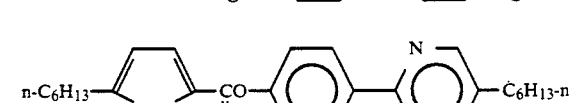 (1-27)

-continued
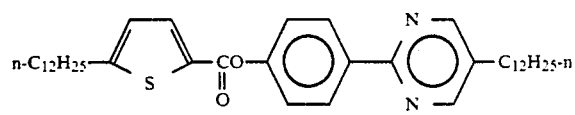
(1-28)
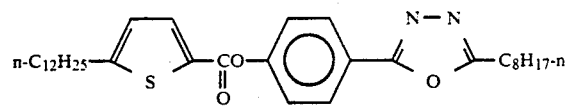
(1-29)
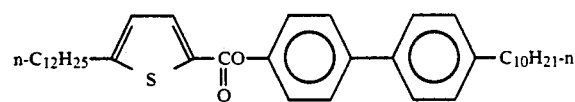
(1-30)
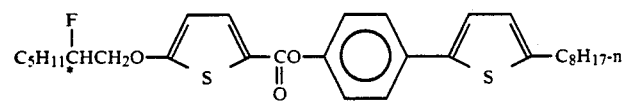
(1-31)
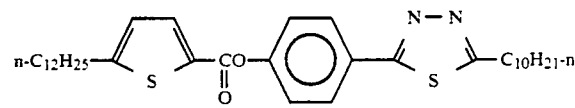
(1-32)
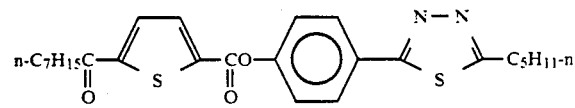
(1-33)
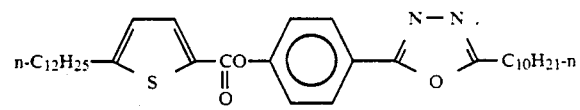
(1-34)
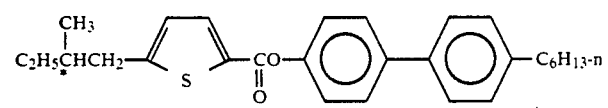
(1-35)
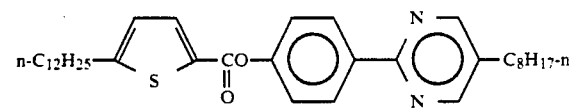
(1-36)
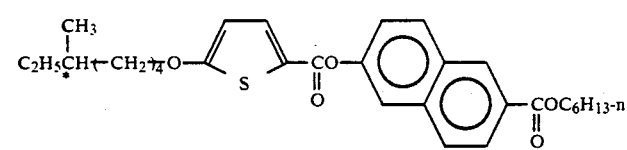
(1-37)
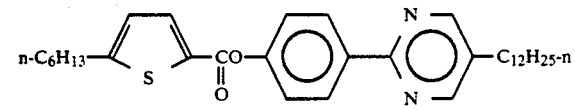
(1-38)
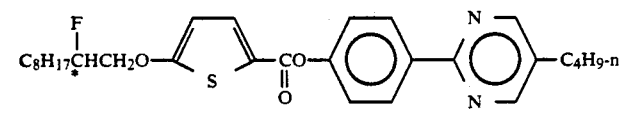
(1-39)
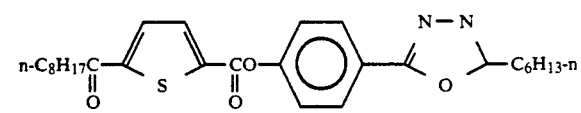
(1-40)

-continued
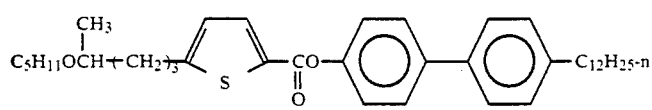 (1-41)
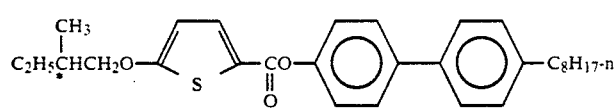 (1-42)
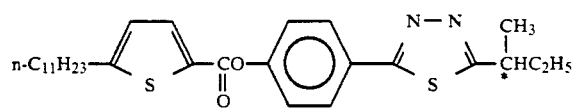 (1-43)
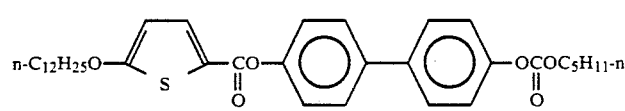 (1-44)
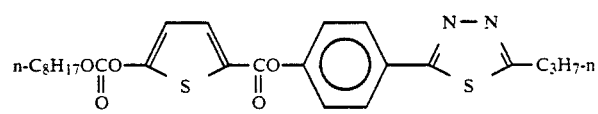 (1-45)
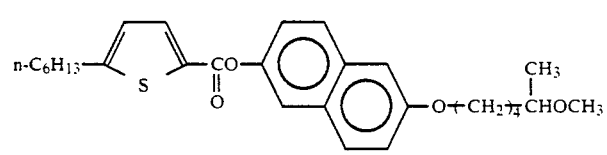 (1-46)
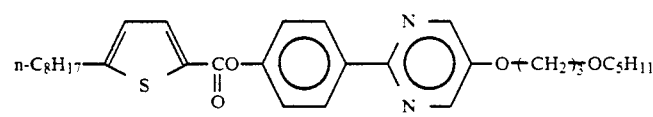 (1-47)
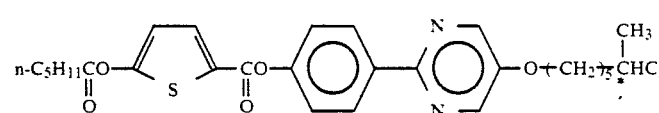 (1-48)
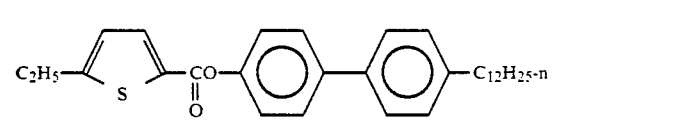 (1-49)
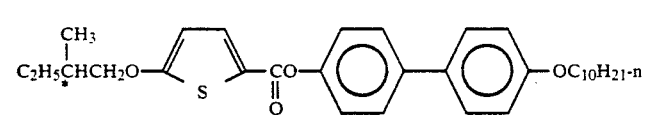 (1-50)
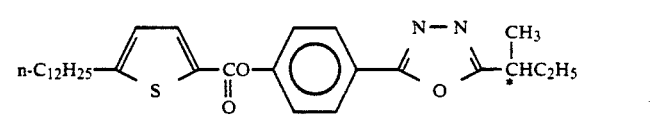 (1-51)
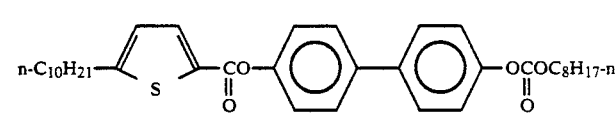 (1-52)
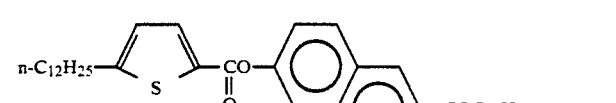 (1-53)

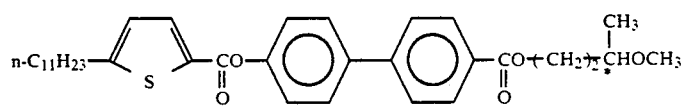
(1-54)
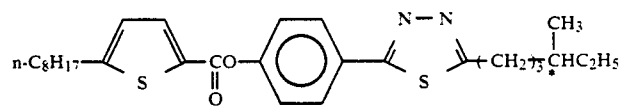
(1-55)
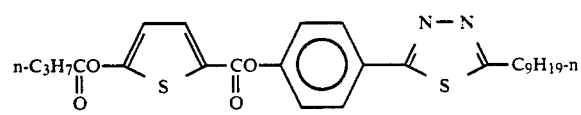
(1-56)
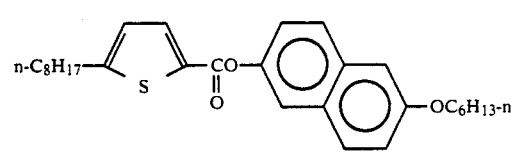
(1-57)
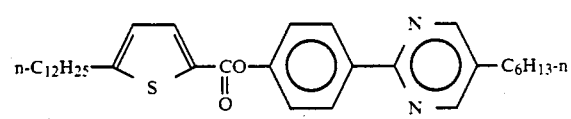
(1-58)
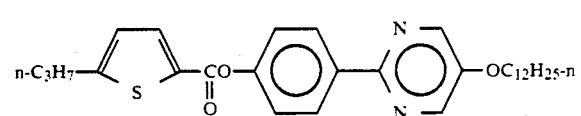
(1-59)
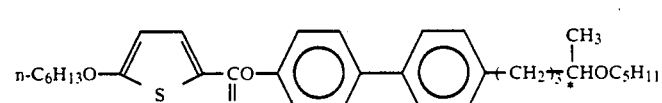
(1-60)
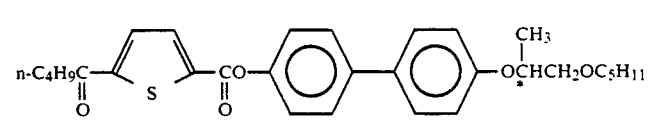
(1-61)
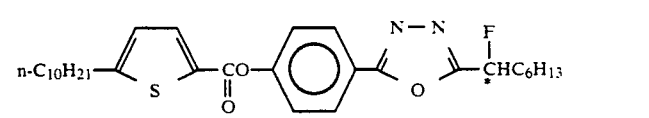
(1-62)
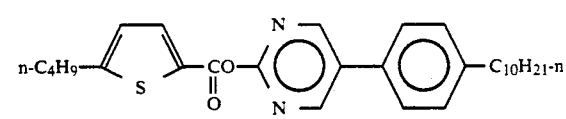
(1-63)
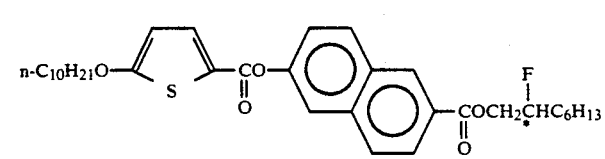
(1-64)
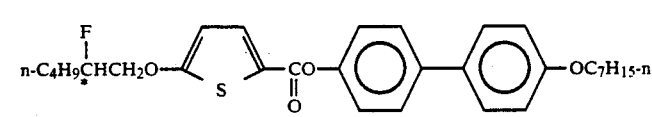
(1-65)
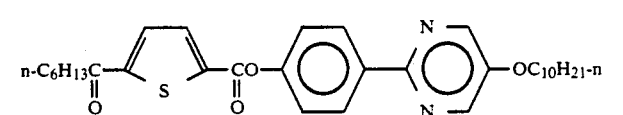
(1-66)

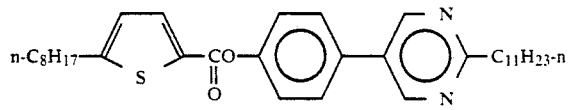 (1-67)
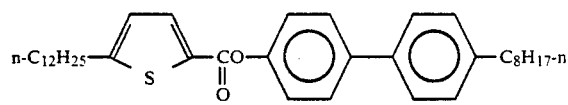 (1-68)
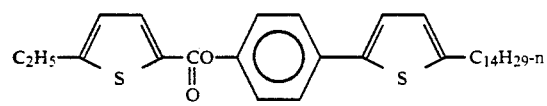 (1-69)
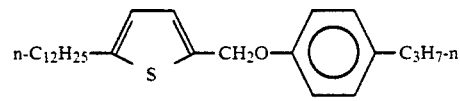 (1-70)
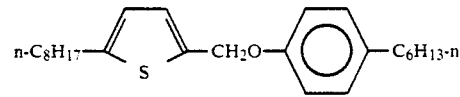 (1-71)
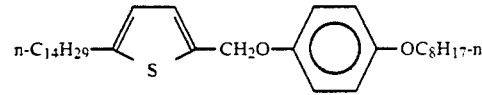 (1-72)
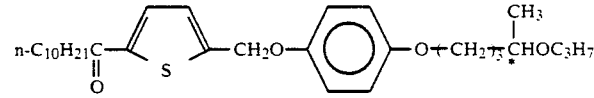 (1-73)
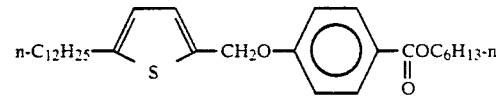 (1-74)
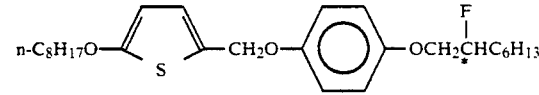 (1-75)
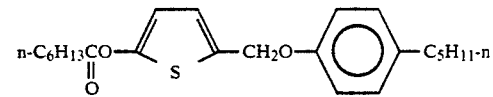 (1-76)
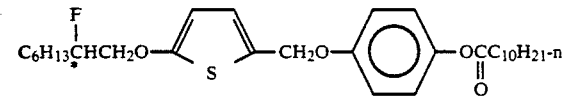 (1-77)
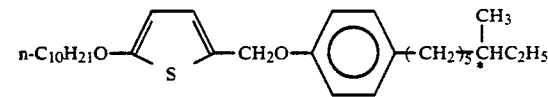 (1-78)
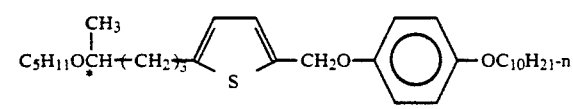 (1-79)

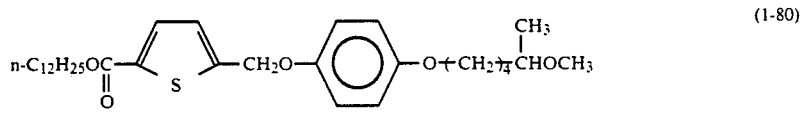 (1-80)
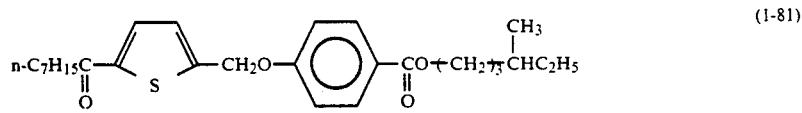 (1-81)
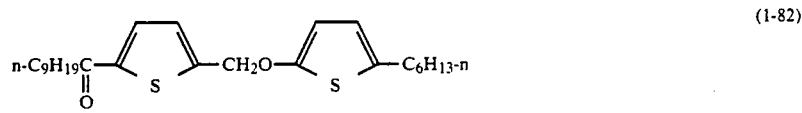 (1-82)
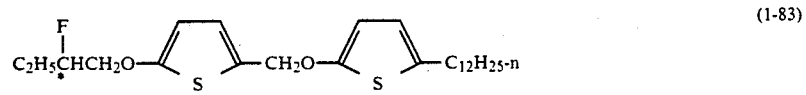 (1-83)
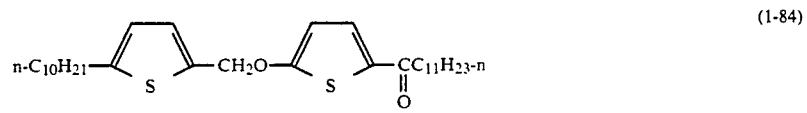 (1-84)
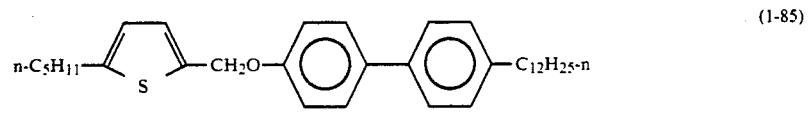 (1-85)
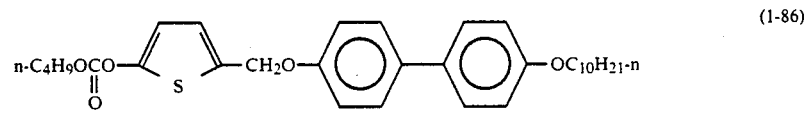 (1-86)
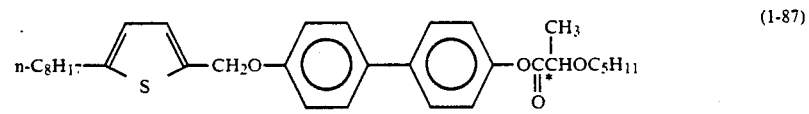 (1-87)
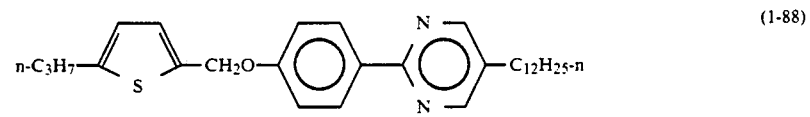 (1-88)
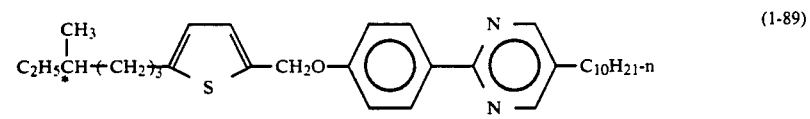 (1-89)
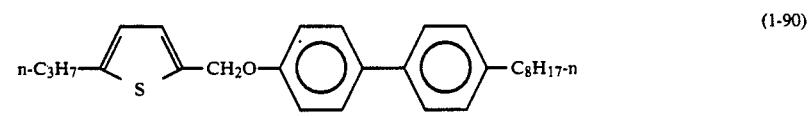 (1-90)
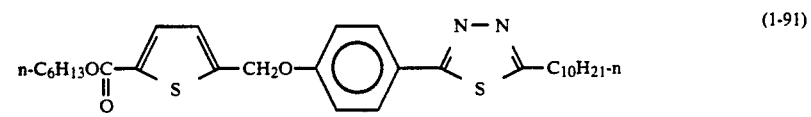 (1-91)
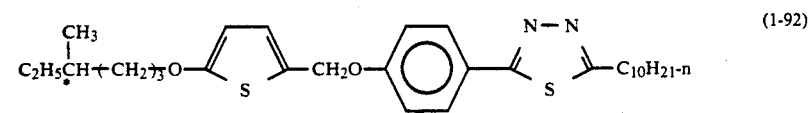 (1-92)

-continued
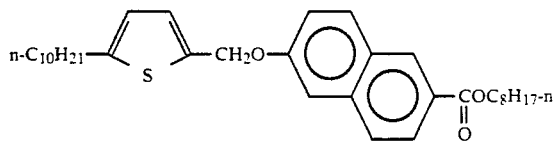 (1-93)
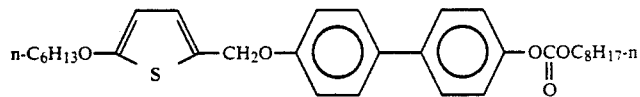 (1-94)
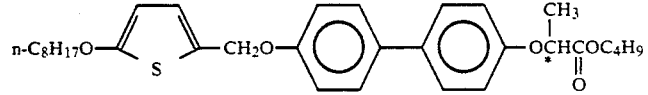 (1-95)
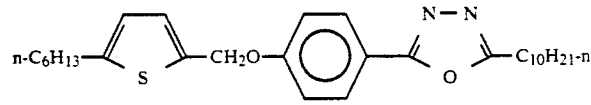 (1-96)
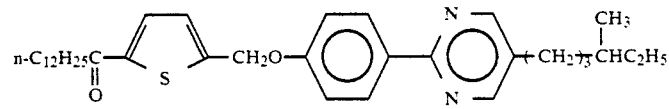 (1-97)
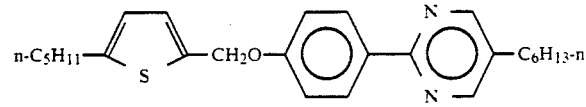 (1-98)
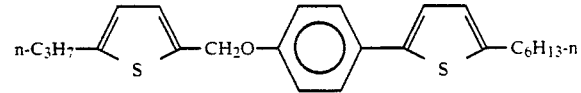 (1-99)
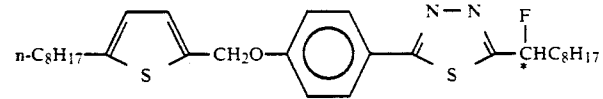 (1-100)
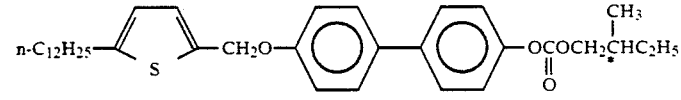 (1-101)
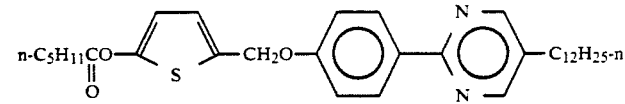 (1-102)
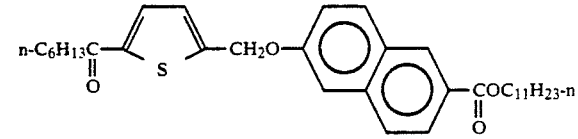 (1-103)
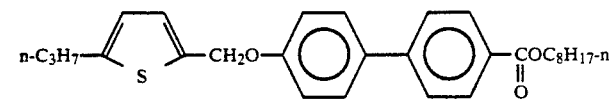 (1-104)
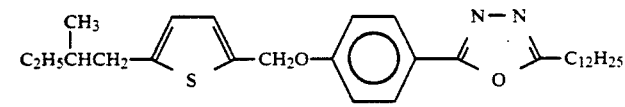 (1-105)

-continued
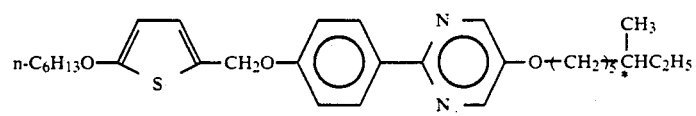 (1-106)
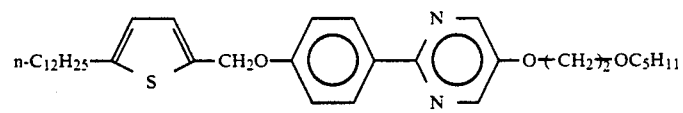 (1-107)
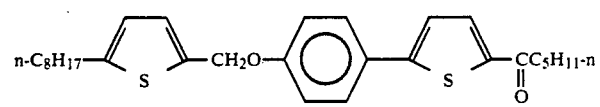 (1-108)
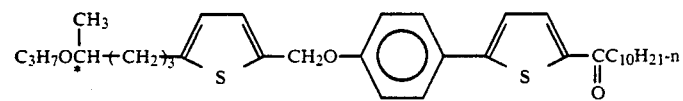 (1-109)
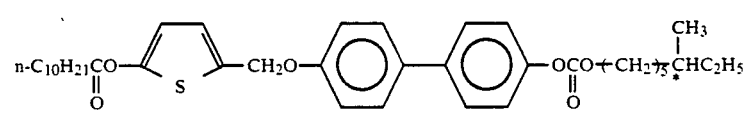 (1-110)
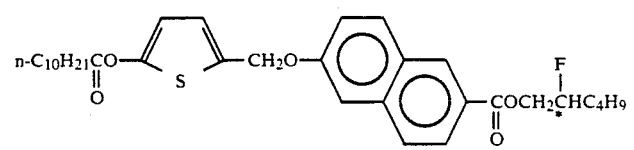 (1-111)
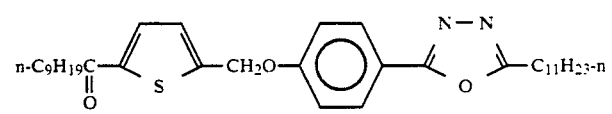 (1-112)
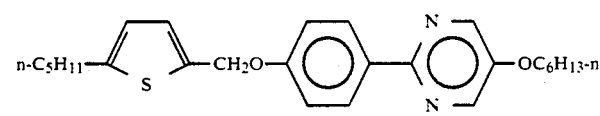 (1-113)
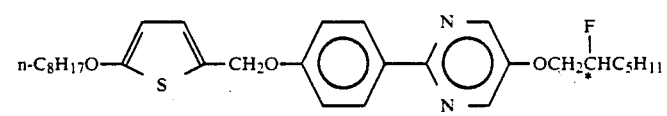 (1-114)
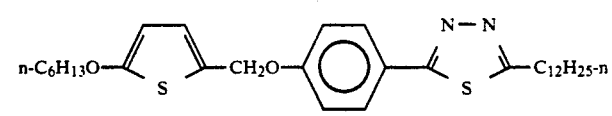 (1-115)
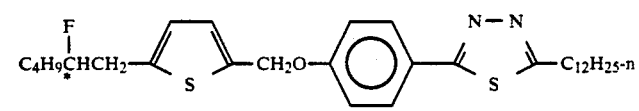 (1-116)
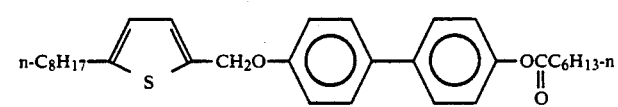 (1-117)
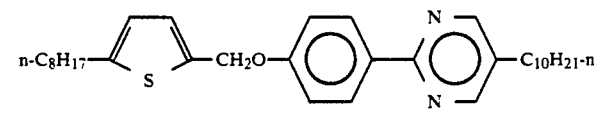 (1-118)

-continued
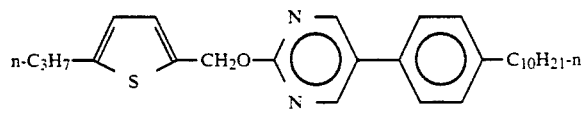 (1-119)
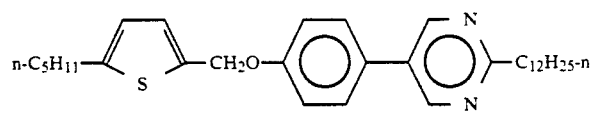 (1-120)
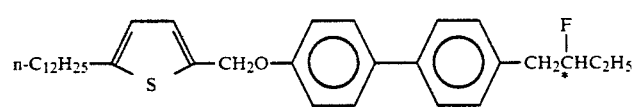 (1-121)
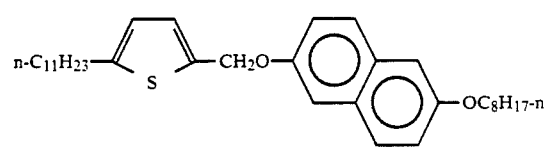 (1-122)
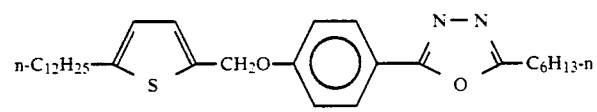 (1-123)
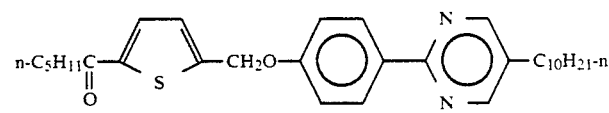 (1-124)
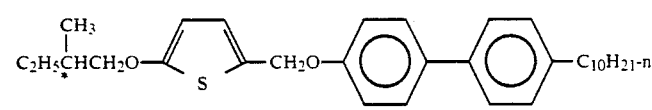 (1-125)
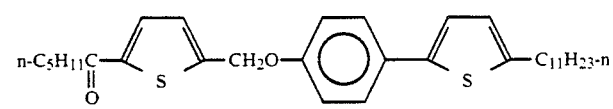 (1-126)
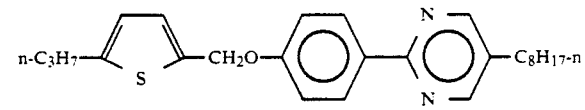 (1-127)
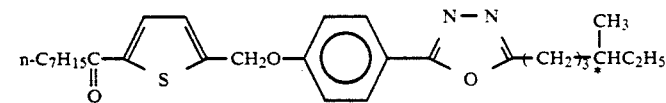 (1-128)
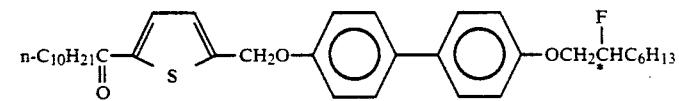 (1-129)
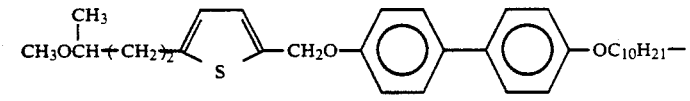 (1-130)
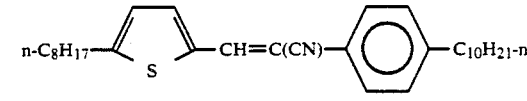 (1-131)

-continued
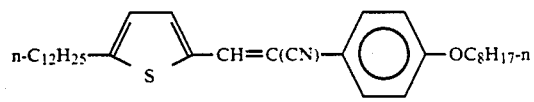 (1-132)
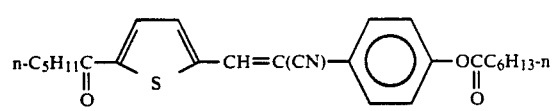 (1-133)
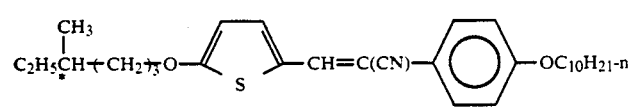 (1-134)
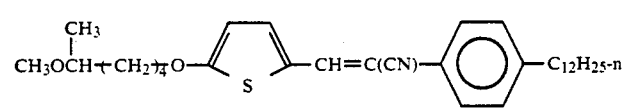 (1-135)
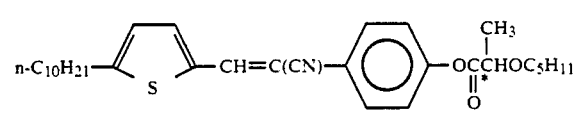 (1-136)
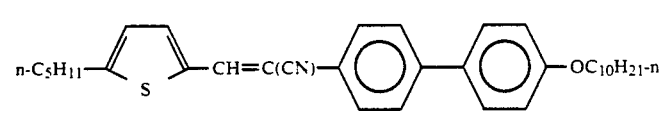 (1-137)
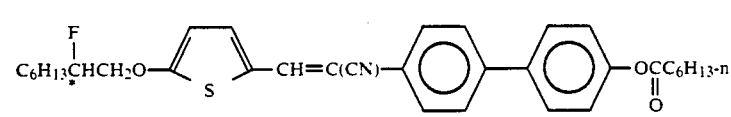 (1-138)
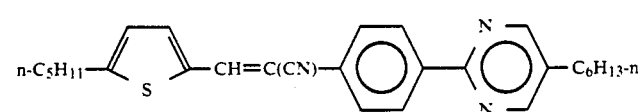 (1-139)
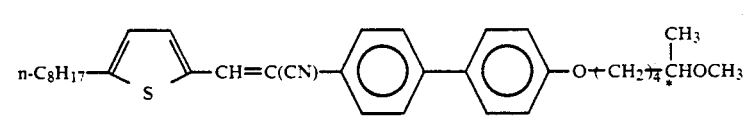 (1-140)
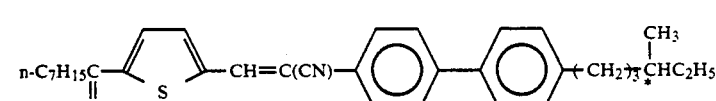 (1-141)
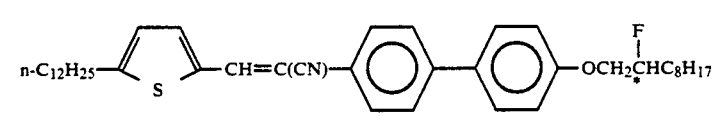 (1-142)
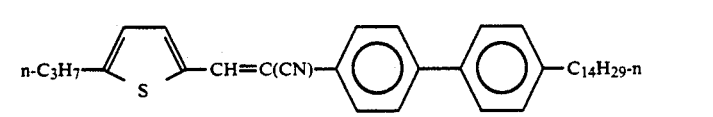 (1-143)
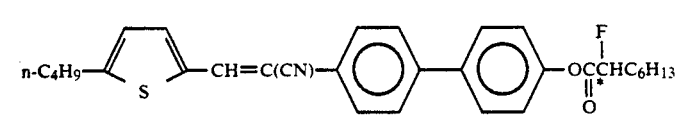 (1-144)

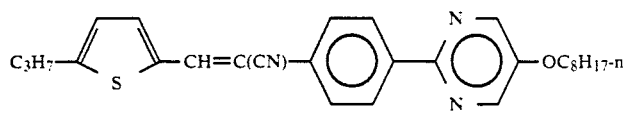 (1-145)
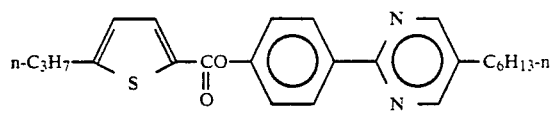 (1-146)
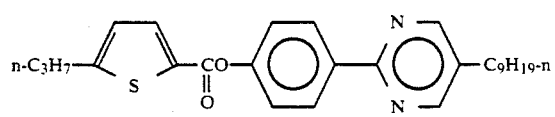 (1-147)
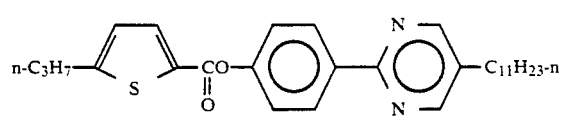 (1-148)
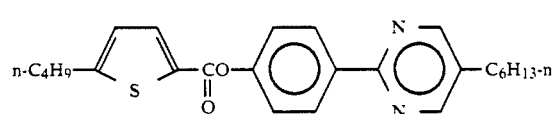 (1-149)
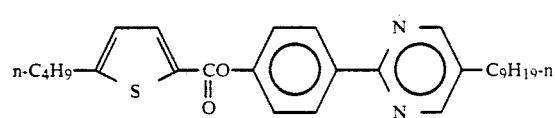 (1-150)
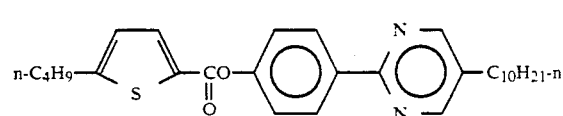 (1-151)
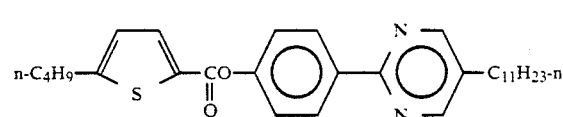 (1-152)
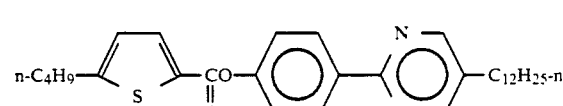 (1-153)
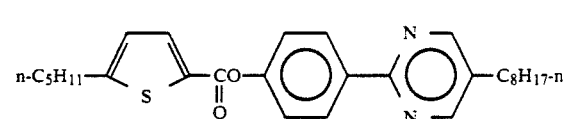 (1-154)
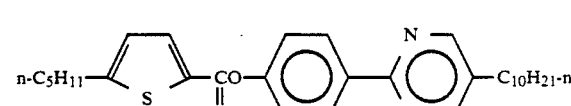 (1-155)
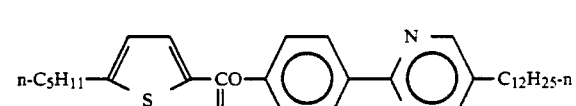 (1-156)
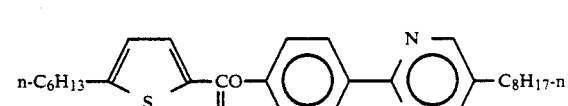 (1-157)

-continued
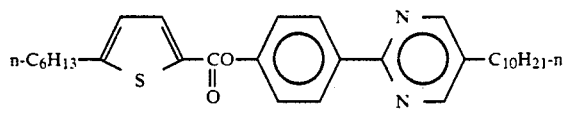 (1-158)
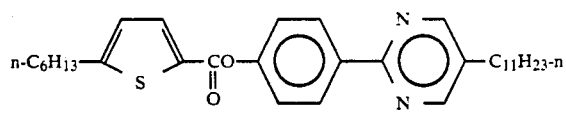 (1-159)
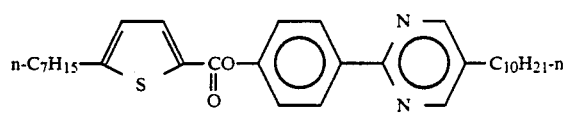 (1-160)
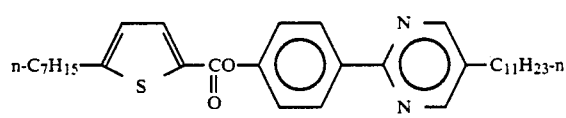 (1-161)
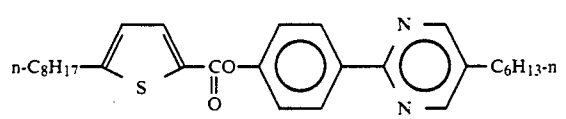 (1-162)
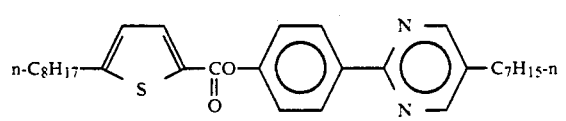 (1-163)
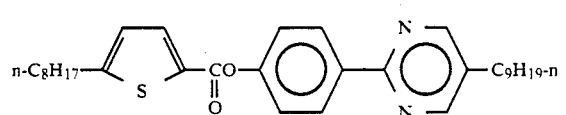 (1-164)
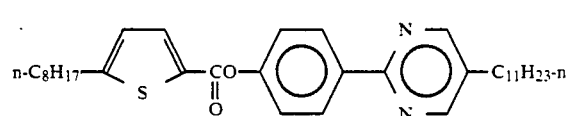 (1-165)
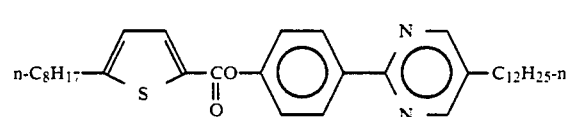 (1-166)
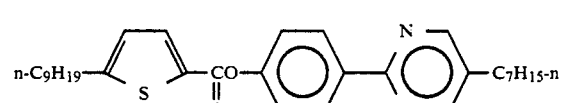 (1-167)
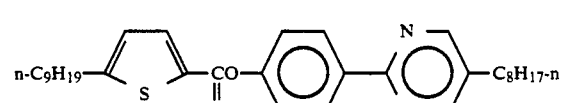 (1-168)
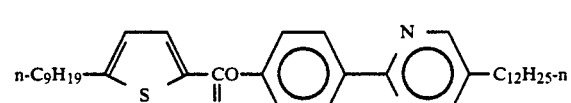 (1-169)
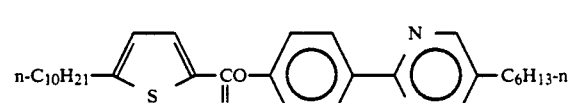 (1-170)

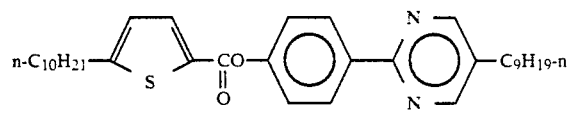 (1-171)
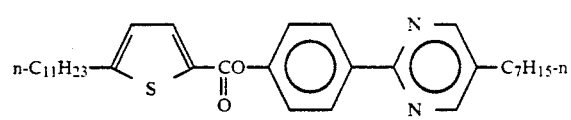 (1-172)
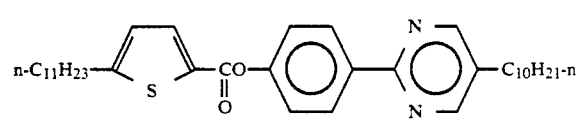 (1-173)
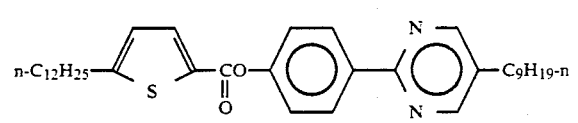 (1-174)
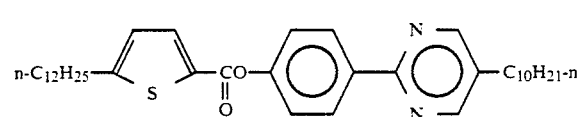 (1-175)
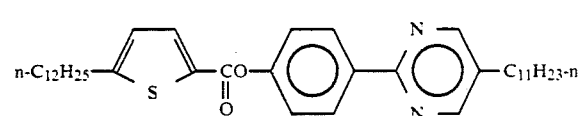 (1-176)
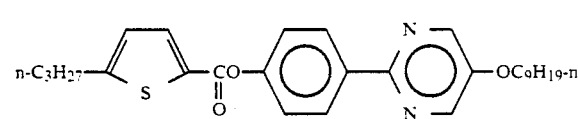 (1-177)
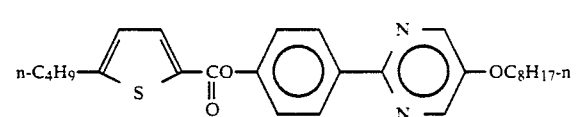 (1-178)
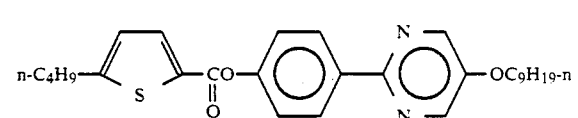 (1-179)
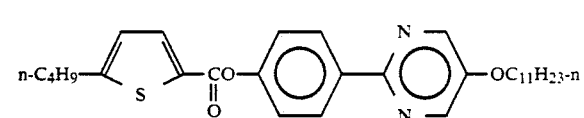 (1-180)
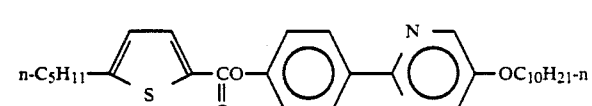 (1-181)
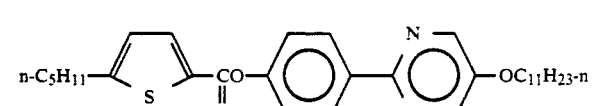 (1-182)
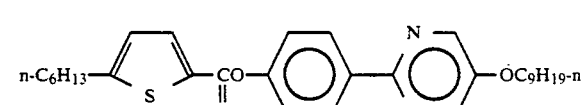 (1-183)

-continued

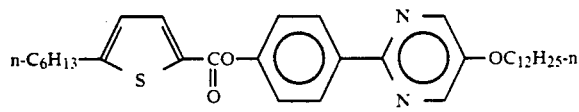 (1-184)

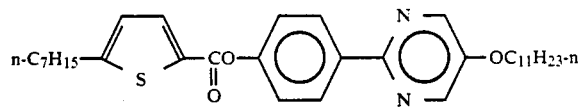 (1-185)

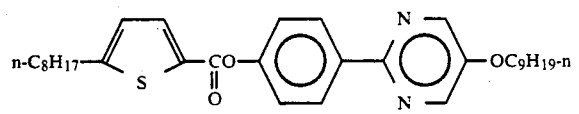 (1-186)

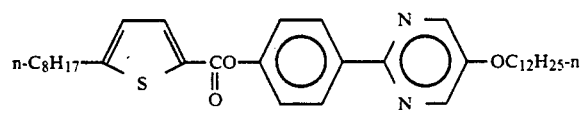 (1-187)

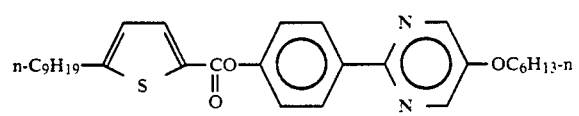 (1-188)

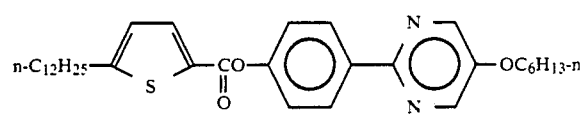 (1-189)

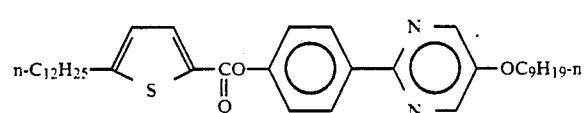 (1-190)

The liquid crystal composition according to the present invention may be obtained by mixing at least one species of the compound represented by the formula (I) and another mesomorphic compound in appropriate proportions. The liquid crystal composition according to the present invention may preferably be formulated as a ferroelectric liquid crystal composition, particularly a ferroelectric chiral smectic liquid crystal composition.

Specific examples of another mesomorphic compounds as described above may include those denoted by the following structural formulas:

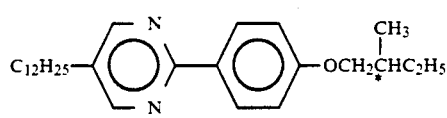 (1)

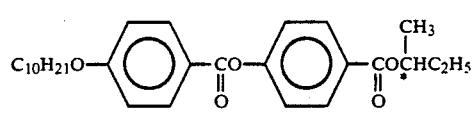 (2)

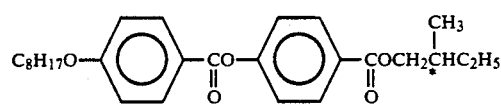 (3)

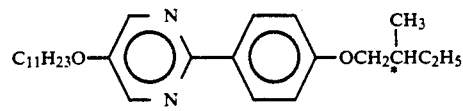 (4)

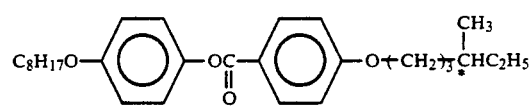 (5)

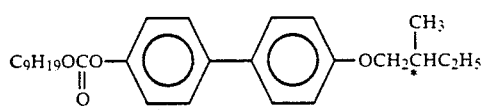
(6)
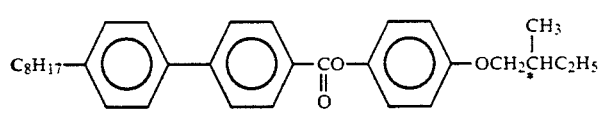
(7)
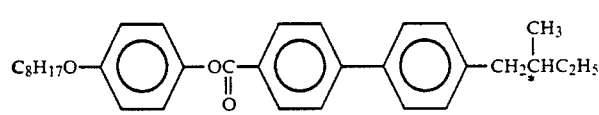
(8)
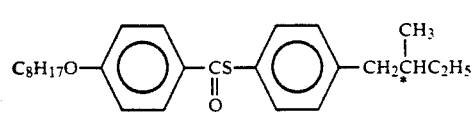
(9)
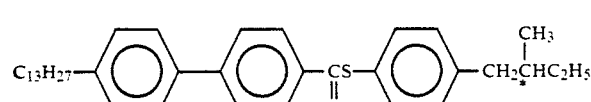
(10)
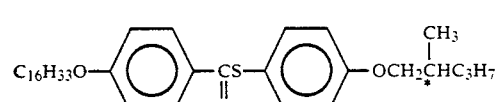
(11)
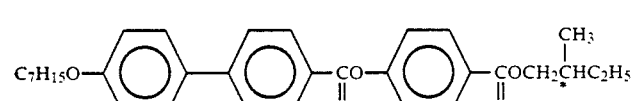
(12)
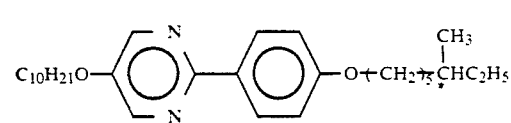
(13)
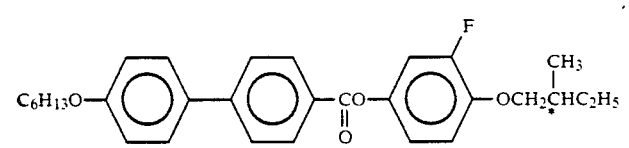
(14)
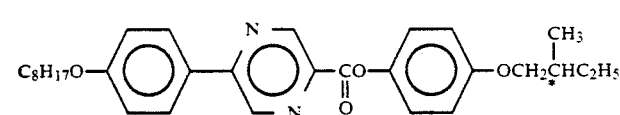
(15)
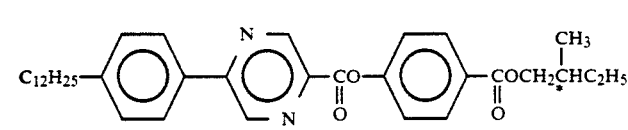
(16)
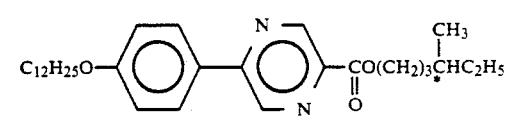
(17)
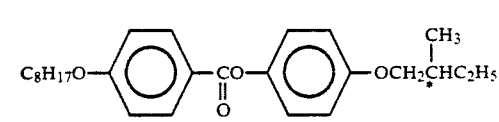
(18)

-continued
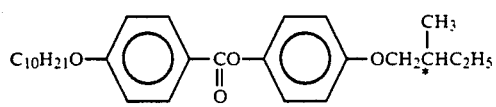 (19)
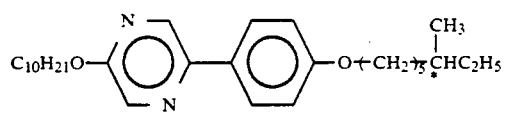 (20)
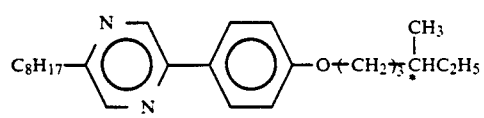 (21)
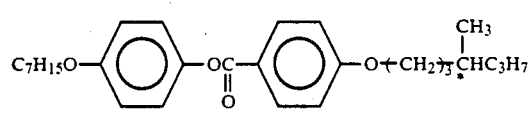 (22)
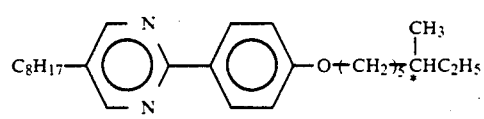 (23)
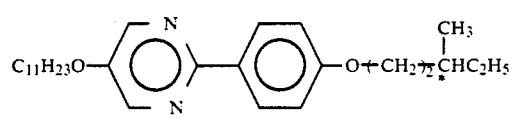 (24)
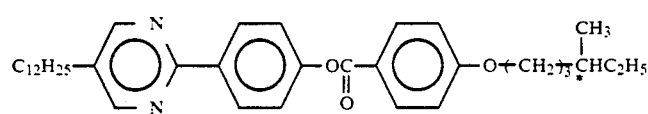 (25)
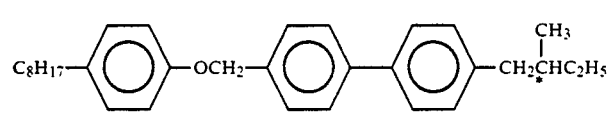 (26)
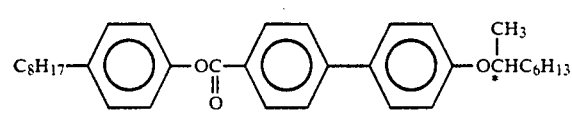 (27)
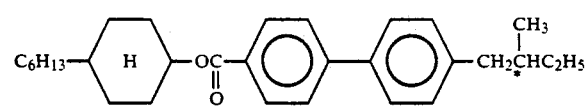 (28)
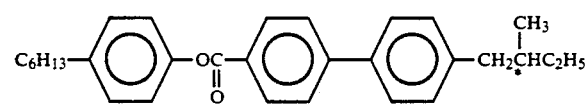 (29)
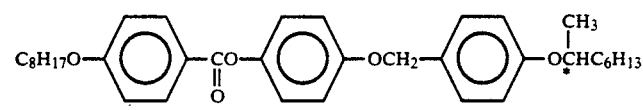 (30)
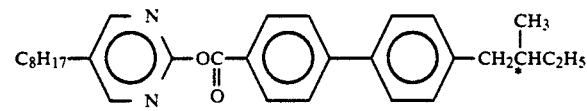 (31)

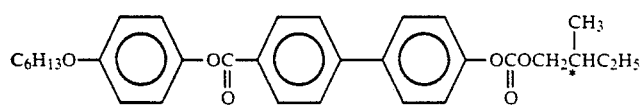 (32)
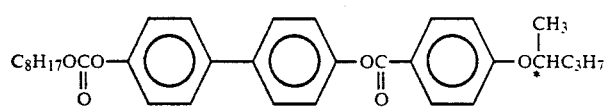 (33)
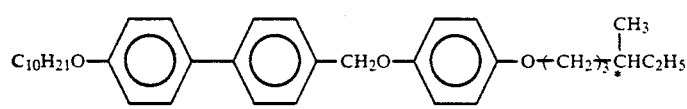 (34)
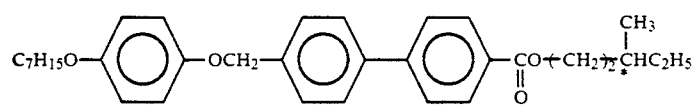 (35)
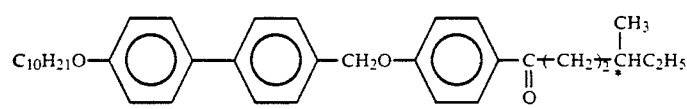 (36)
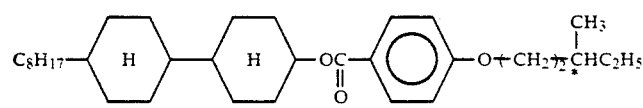 (37)
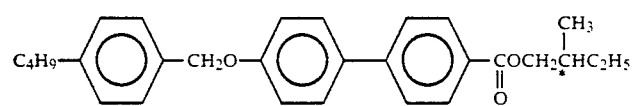 (38)
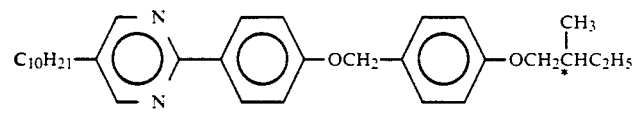 (39)
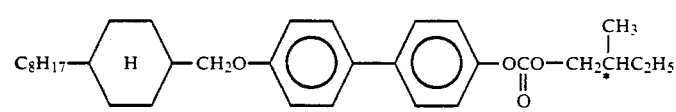 (40)
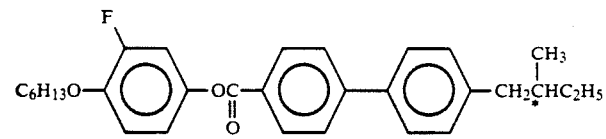 (41)
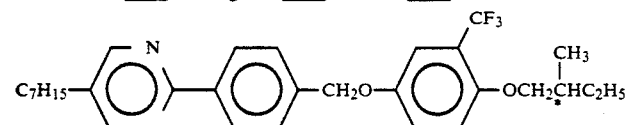 (42)
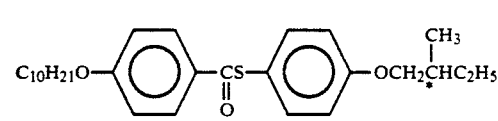 (43)
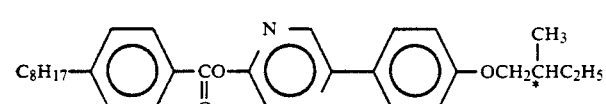 (44)

-continued
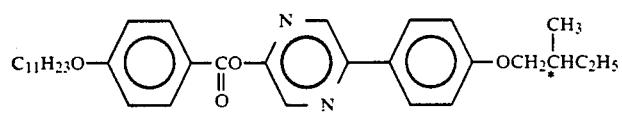 (45)
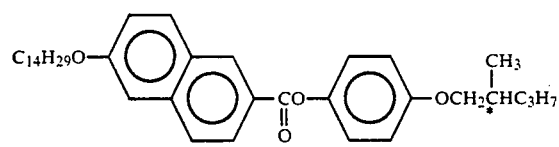 (46)
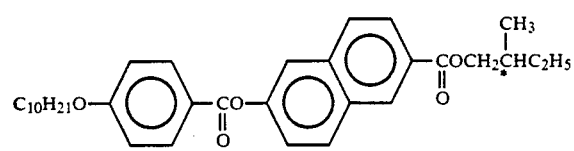 (47)
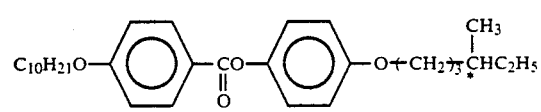 (48)
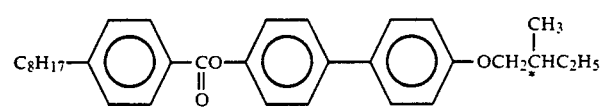 (49)
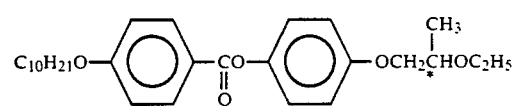 (50)
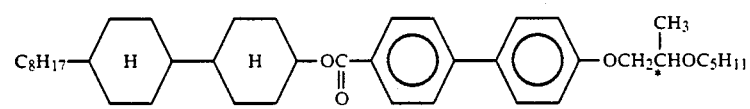 (51)
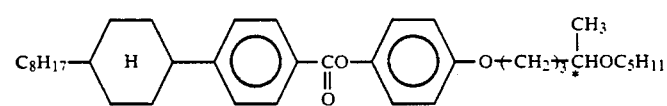 (52)
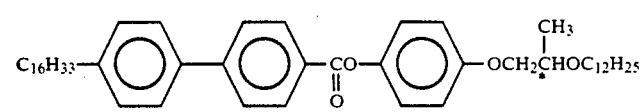 (53)
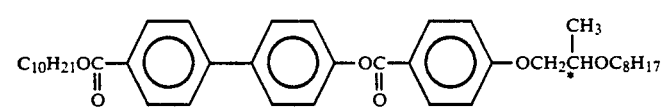 (54)
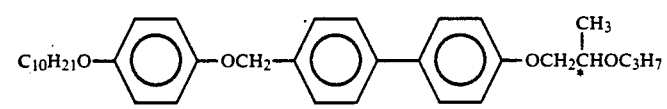 (55)
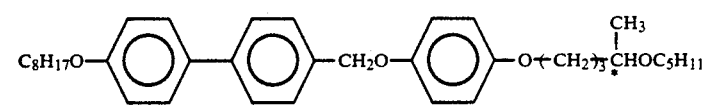 (56)
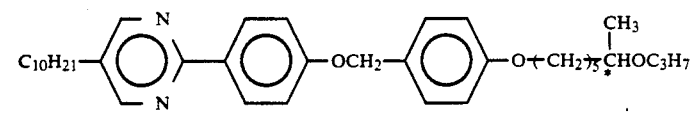 (57)

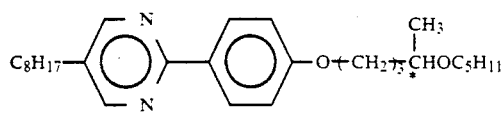 (58)
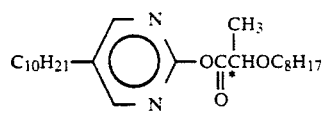 (59)
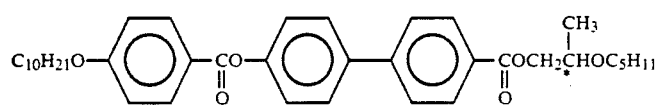 (60)
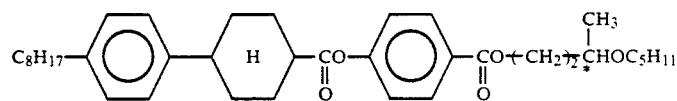 (61)
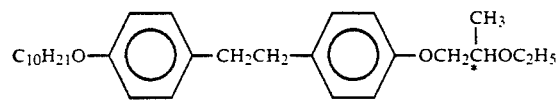 (62)
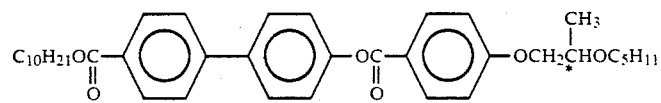 (63)
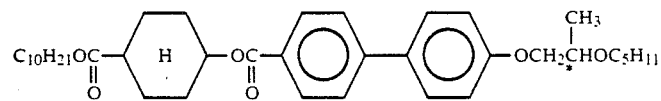 (64)
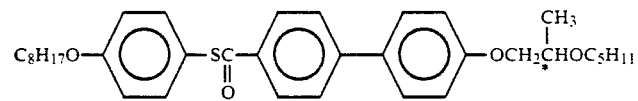 (65)
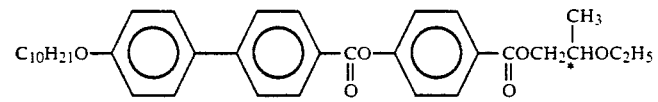 (66)
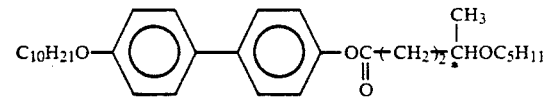 (67)
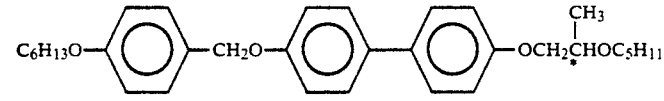 (68)
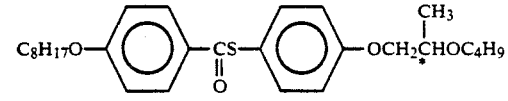 (69)
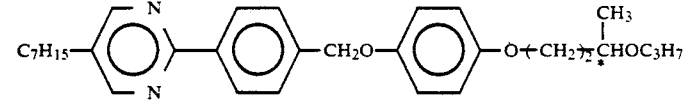 (70)

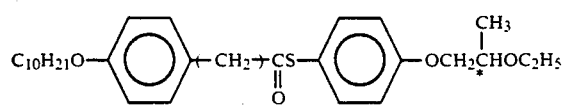 (71)
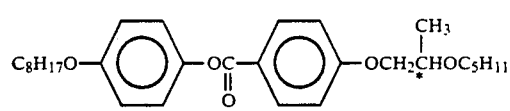 (72)
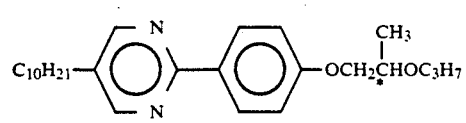 (73)
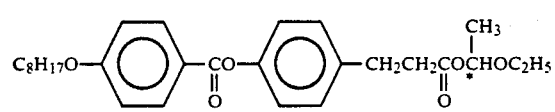 (74)
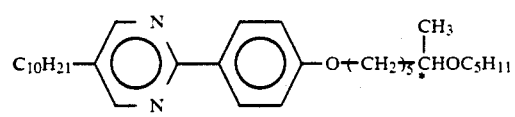 (75)
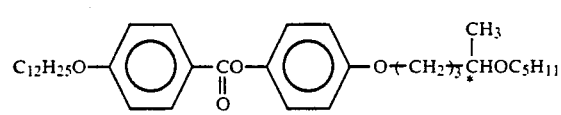 (76)
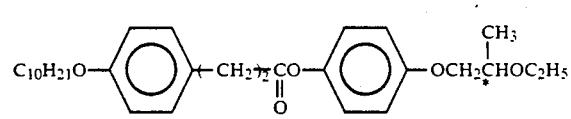 (77)
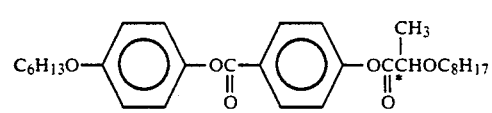 (78)
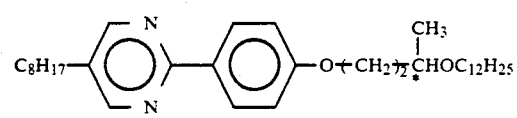 (79)
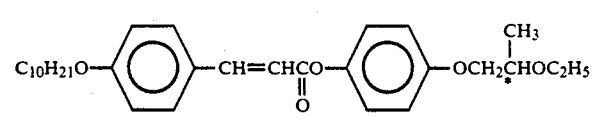 (80)
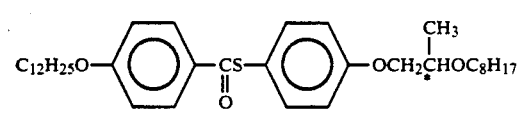 (81)
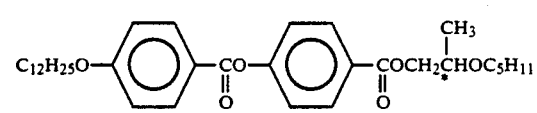 (82)
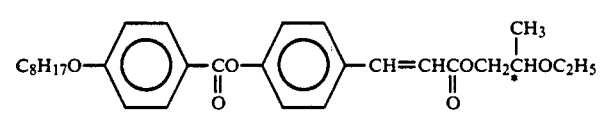 (83)

-continued
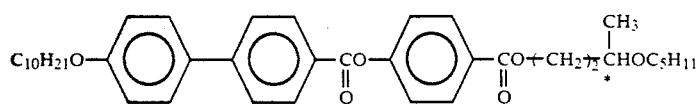 (84)
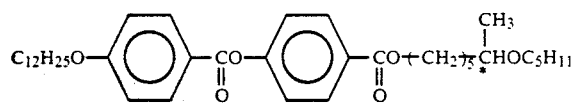 (85)
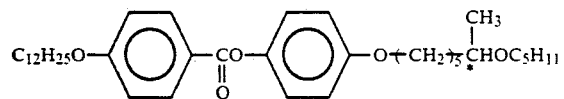 (86)
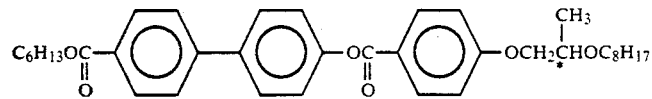 (87)
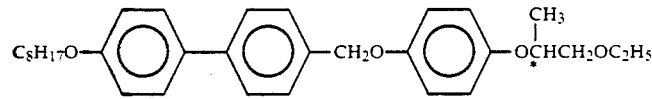 (88)
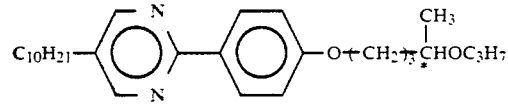 (89)
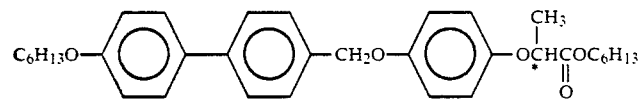 (90)
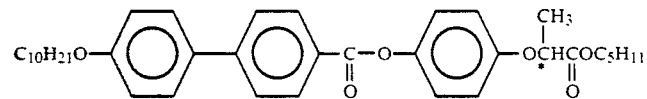 (91)
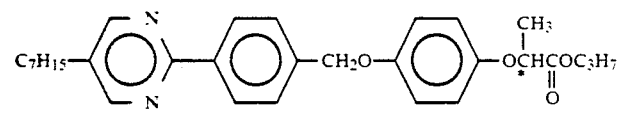 (92)
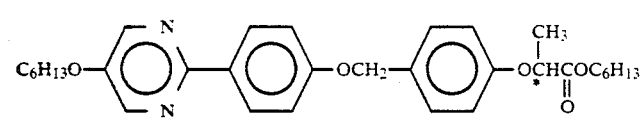 (93)
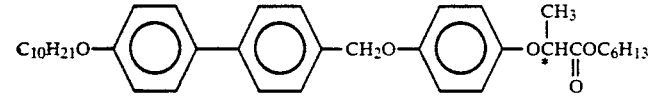 (94)
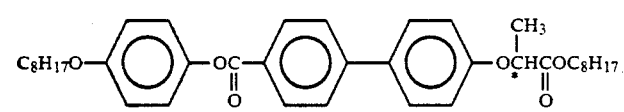 (95)
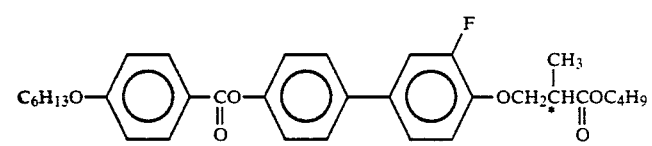 (96)

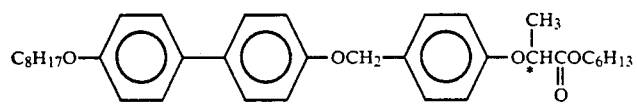 (97)
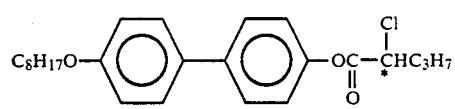 (98)
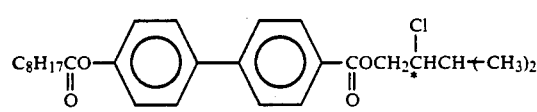 (99)
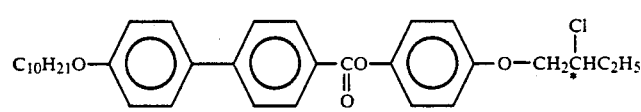 (100)
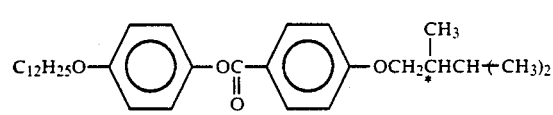 (101)
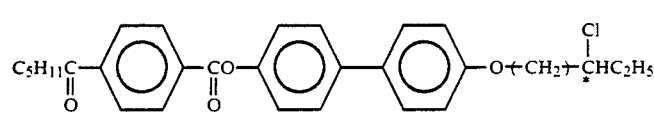 (102)
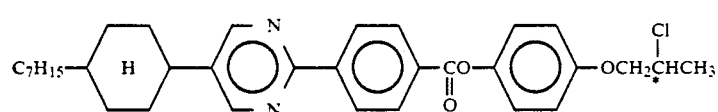 (103)
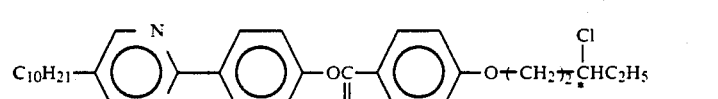 (104)
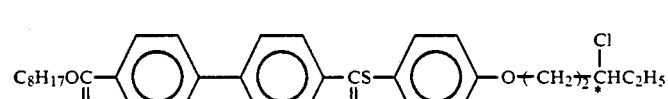 (105)
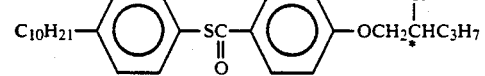 (106)
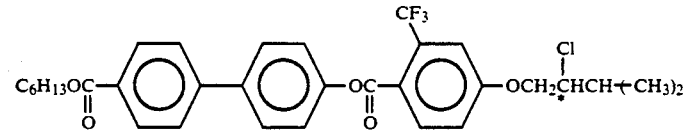 (107)
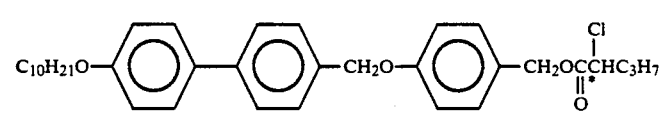 (108)
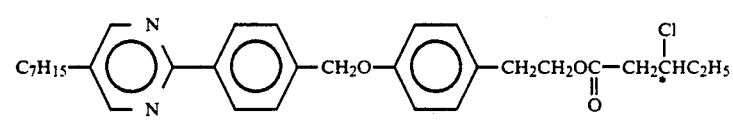 (109)

-continued
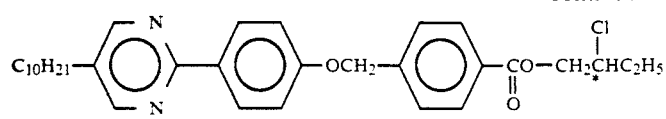 (110)
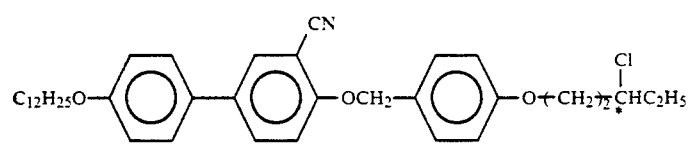 (111)
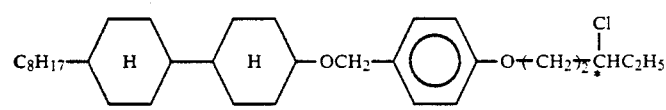 (112)
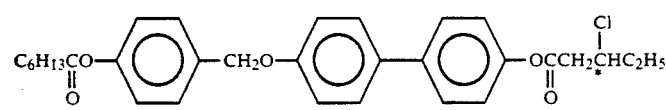 (113)
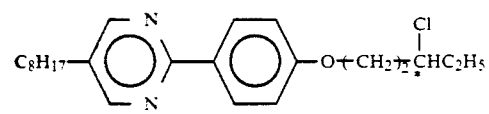 (114)
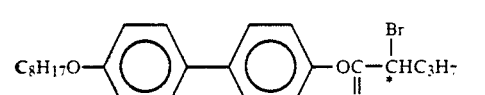 (115)
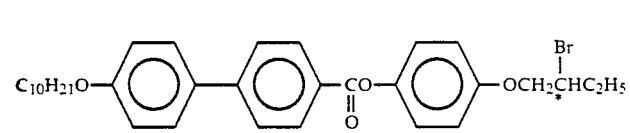 (116)
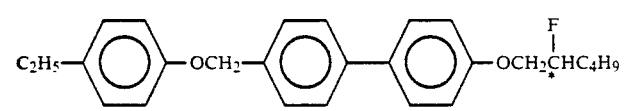 (117)
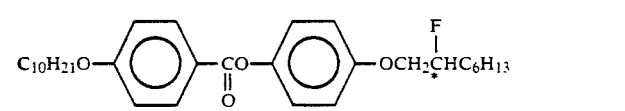 (118)
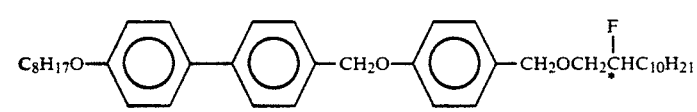 (119)
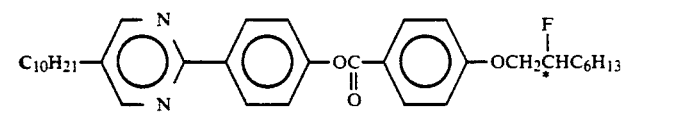 (120)
 (121)
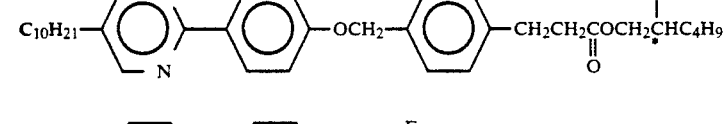
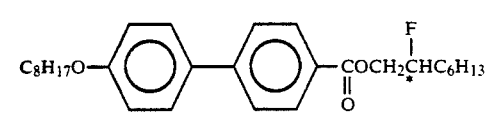 (122)

-continued
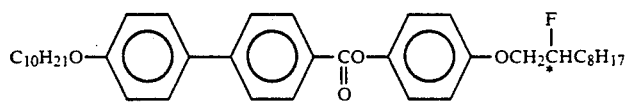 (123)
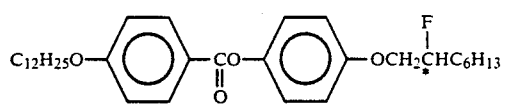 (124)
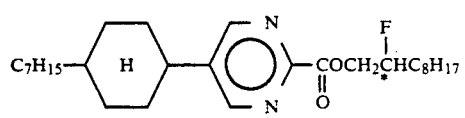 (125)
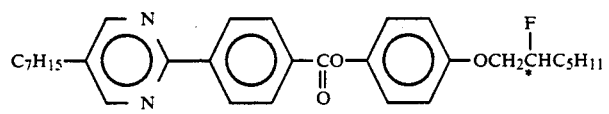 (126)
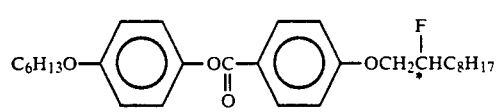 (127)
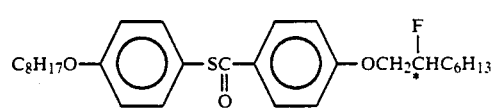 (128)
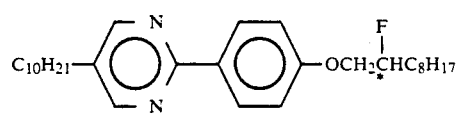 (129)
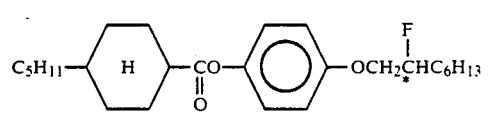 (130)
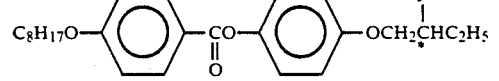 (131)
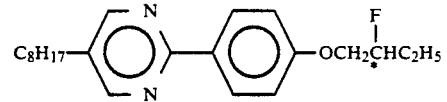 (132)
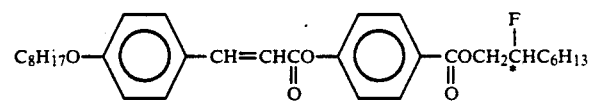 (133)
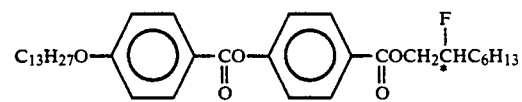 (134)
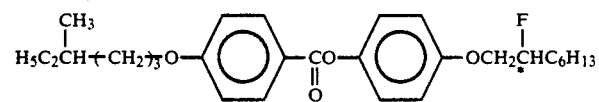 (135)

(136)
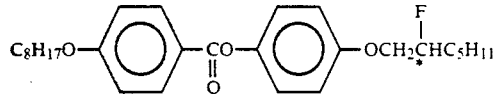
(137)
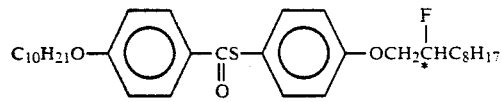
(138)
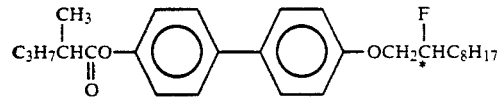
(139)
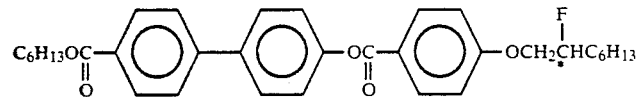
(140)
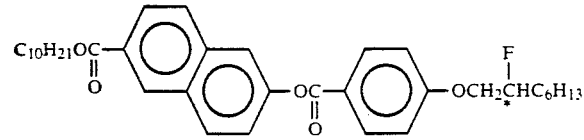
(141)
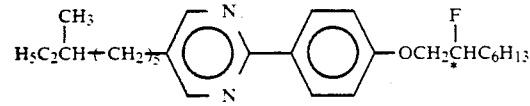
(142)
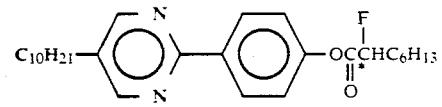
(143)
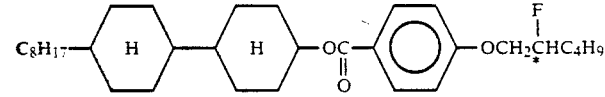
(144)
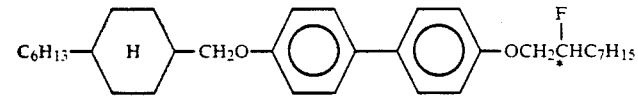
(145)
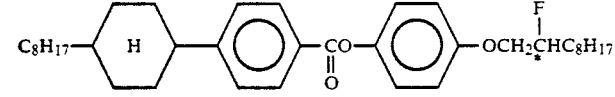
(146)
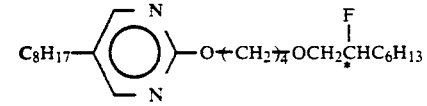
(147)
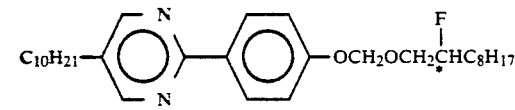
(148)
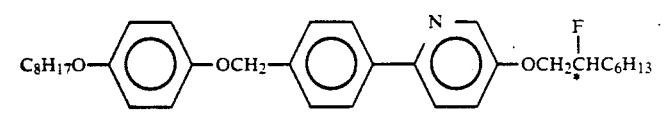

-continued
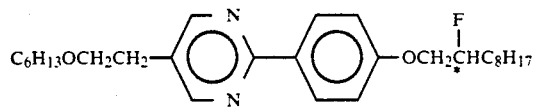 (149)
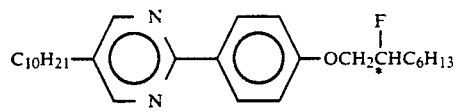 (150)
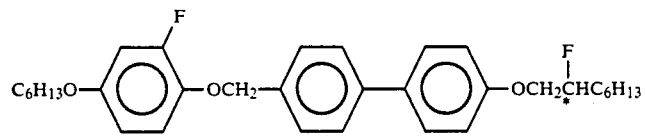 (151)
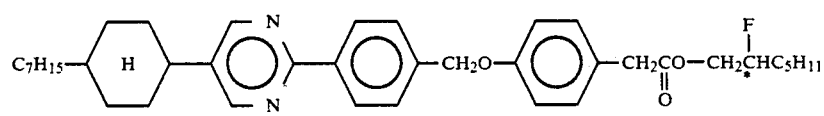 (152)
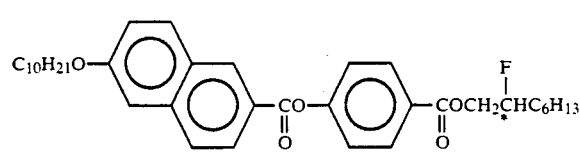 (153)
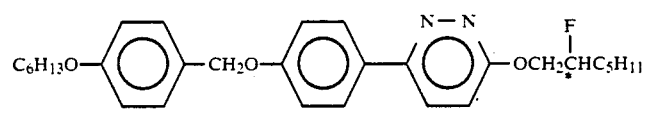 (154)
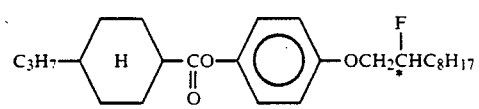 (155)
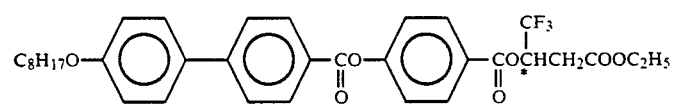 (156)
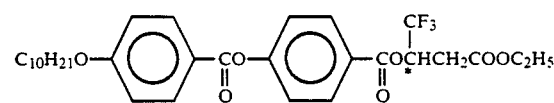 (157)
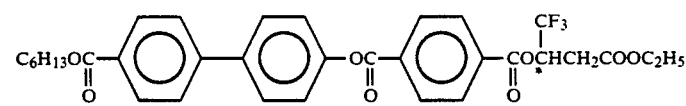 (158)
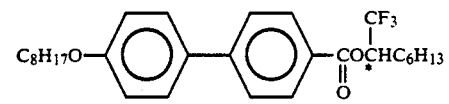 (159)
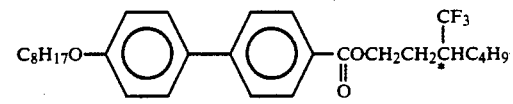 (160)
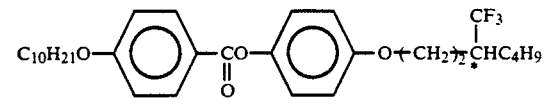 (161)

-continued
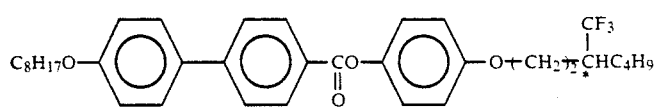 (162)
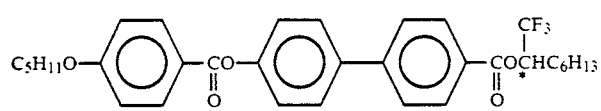 (163)
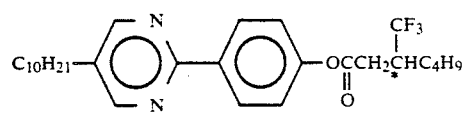 (164)
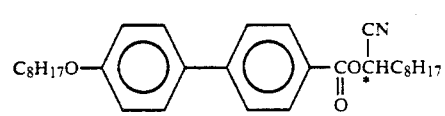 (165)
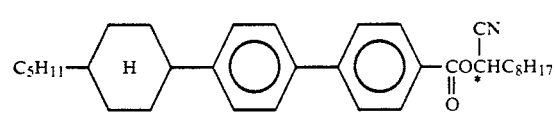 (166)
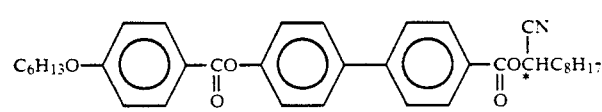 (167)
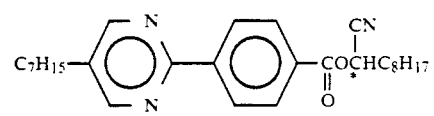 (168)
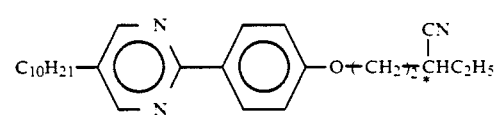 (169)
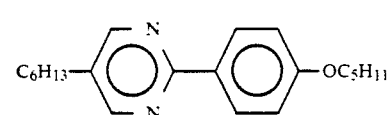 (170)
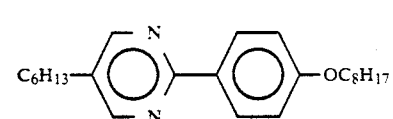 (171)
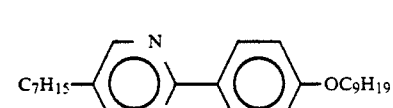 (172)
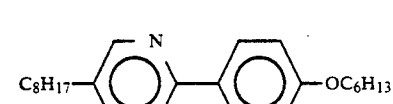 (173)
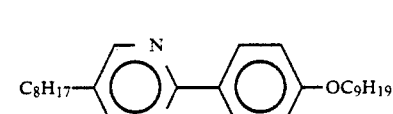 (174)

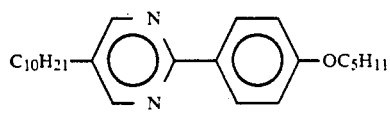 (175)
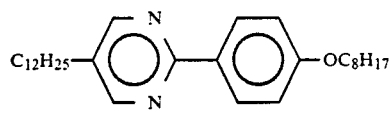 (176)
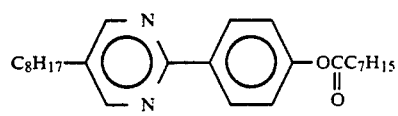 (177)
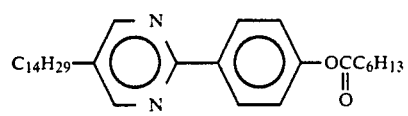 (178)
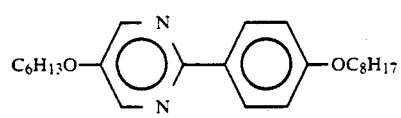 (179)
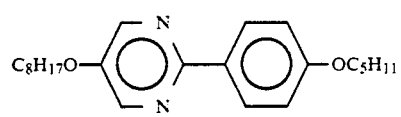 (180)
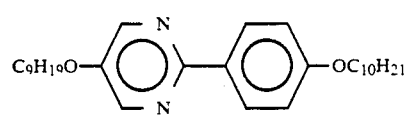 (181)
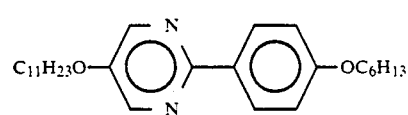 (182)
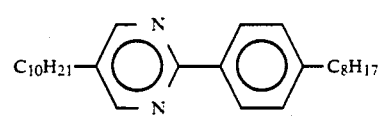 (183)
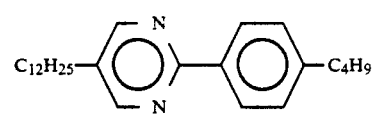 (184)
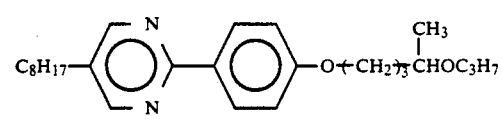 (185)
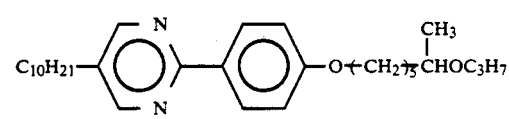 (186)
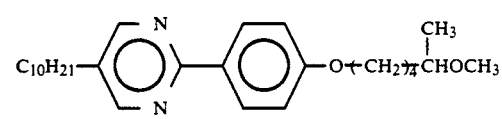 (187)

-continued
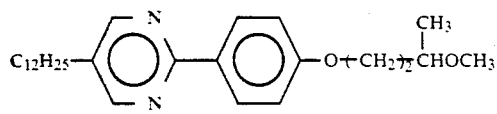 (188)
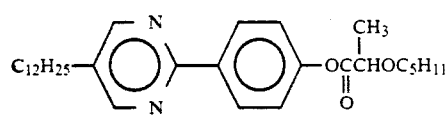 (189)
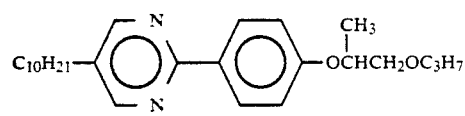 (190)
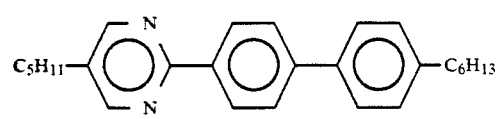 (191)
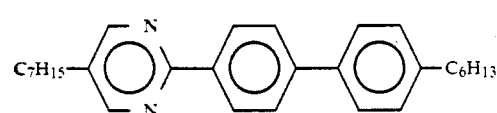 (192)
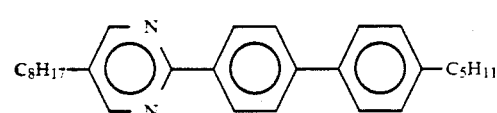 (193)
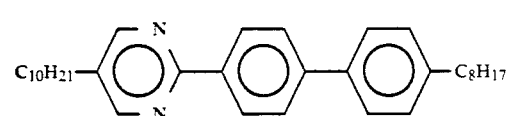 (194)
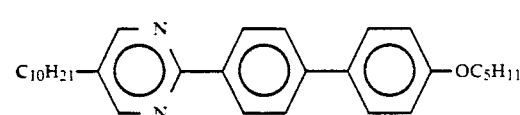 (195)
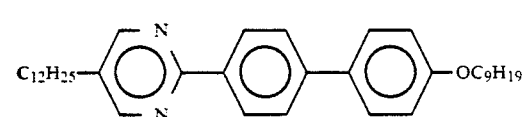 (196)
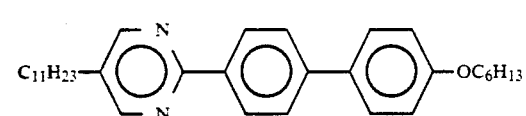 (197)
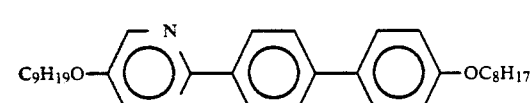 (198)
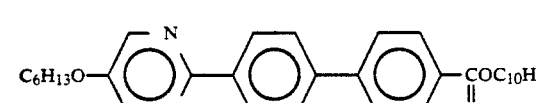 (199)
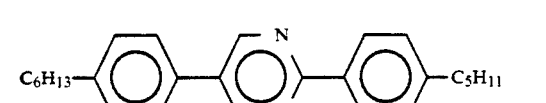 (200)

-continued
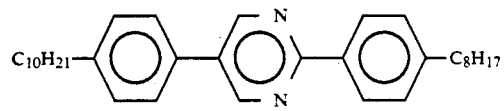 (201)
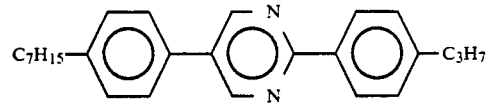 (202)
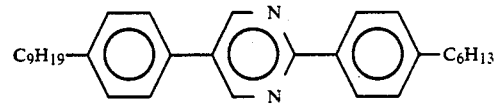 (203)
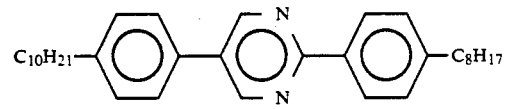 (204)
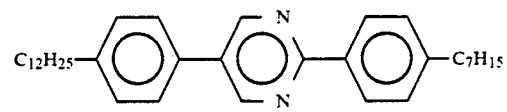 (205)
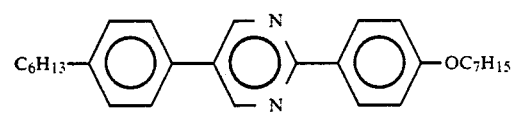 (206)
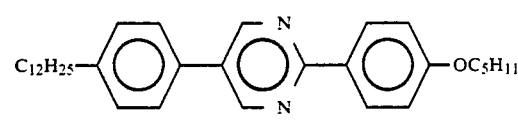 (207)
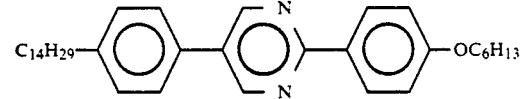 (208)
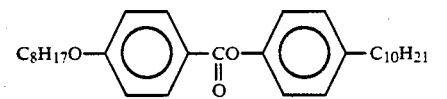 (209)
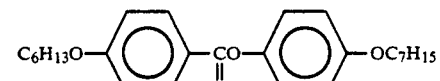 (210)
 (211)
 (212)
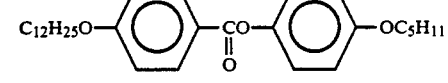 (213)
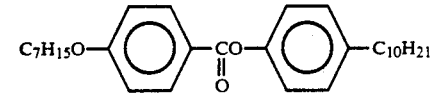

-continued
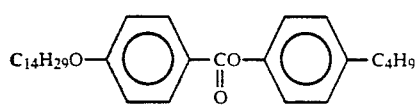 (214)
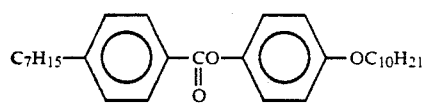 (215)
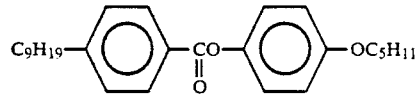 (216)
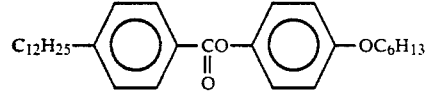 (217)
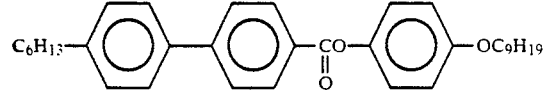 (218)
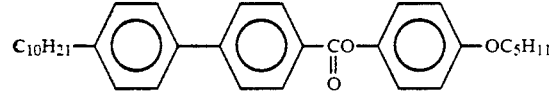 (219)
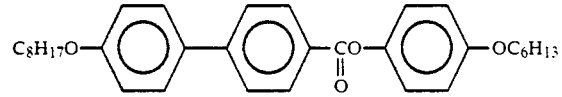 (220)
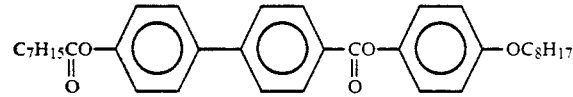 (221)
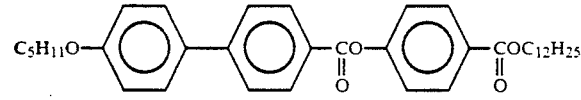 (222)
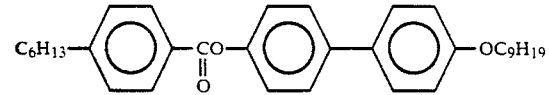 (223)
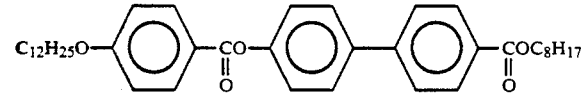 (224)
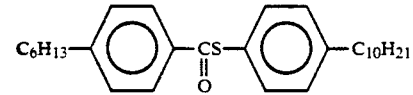 (225)
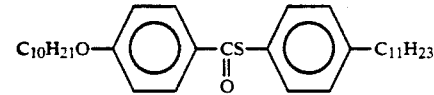 (226)
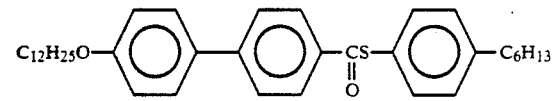 (227)

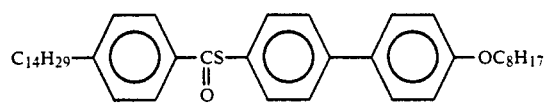 (228)
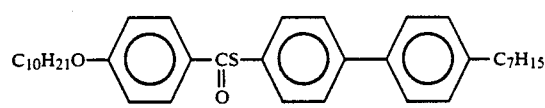 (229)
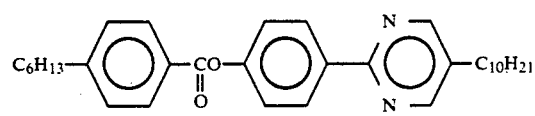 (230)
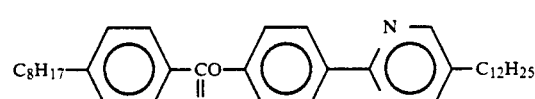 (231)
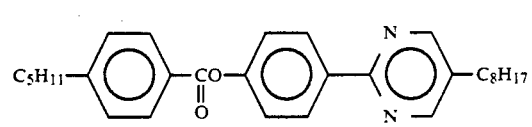 (232)
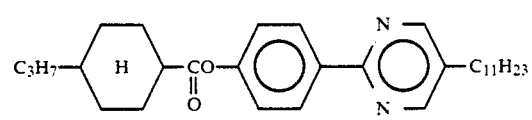 (233)
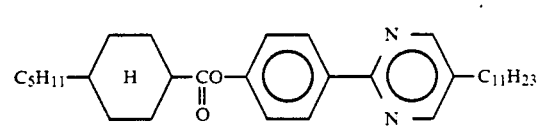 (234)
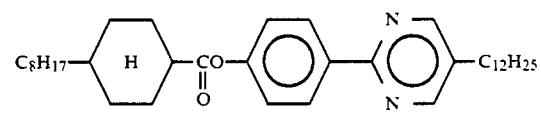 (235)
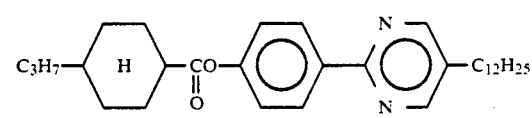 (236)
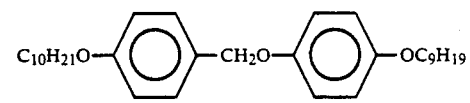 (237)
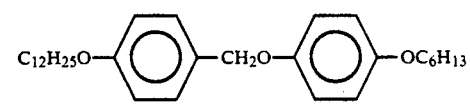 (238)
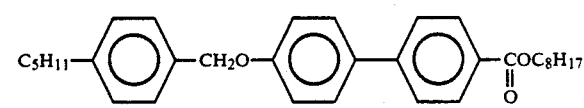 (239)
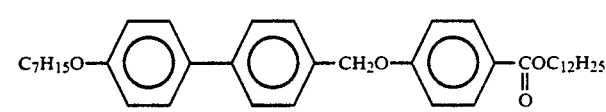 (240)

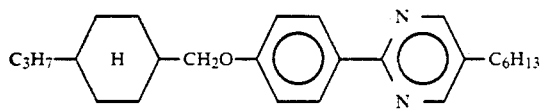 (241)
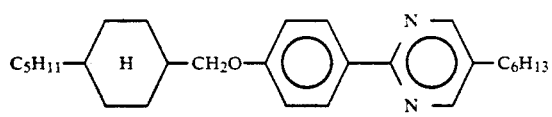 (242)
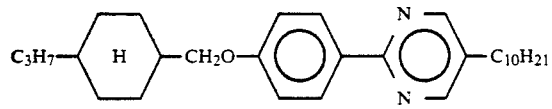 (243)
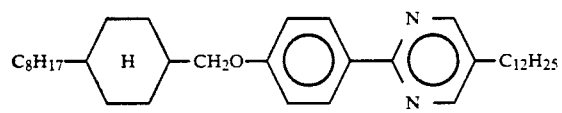 (244)
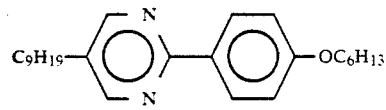 (245)
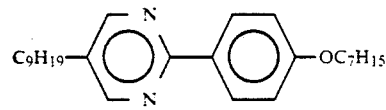 (246)
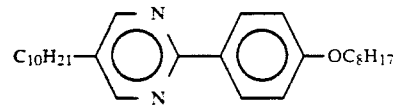 (247)
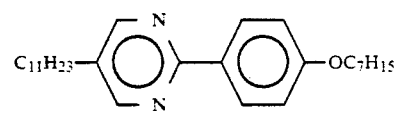 (248)
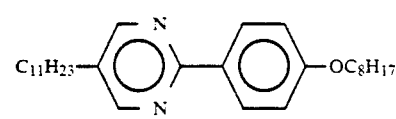 (249)
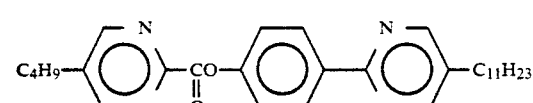 (250)
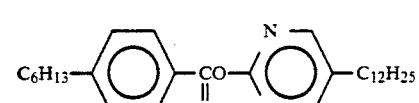 (251)
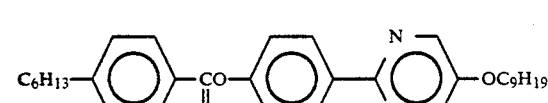 (252)
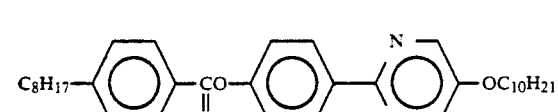 (253)

-continued
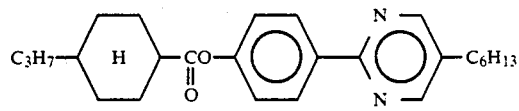 (254)
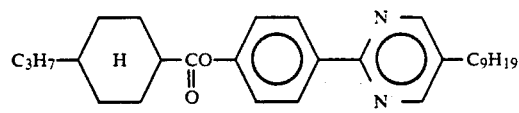 (255)
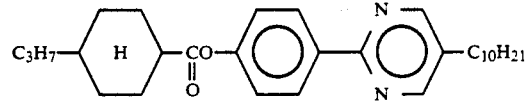 (256)
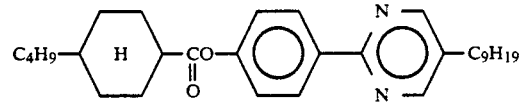 (257)
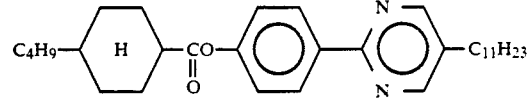 (258)
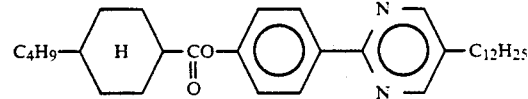 (259)
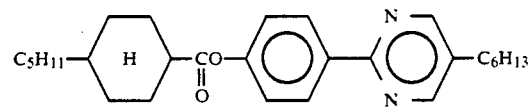 (260)
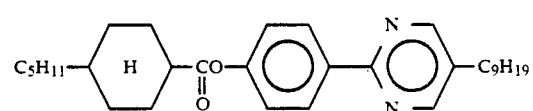 (261)
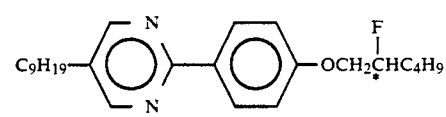 (262)
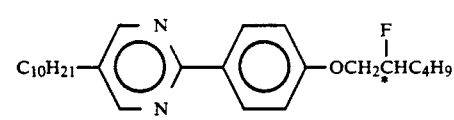 (263)
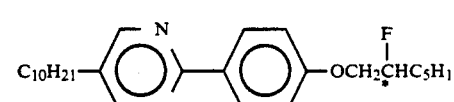 (264)
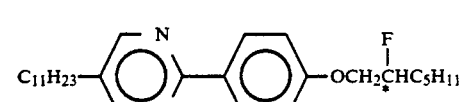 (265)
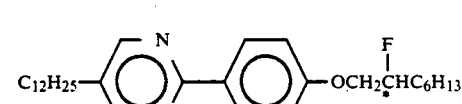 (266)

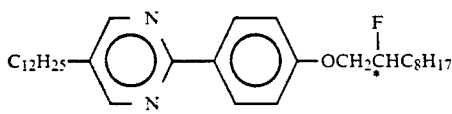

(267)

In formulating the liquid crystal composition according to the present invention, it is desirable to mix 1-500 wt. parts preferably 1-100 wt. parts, of a compound represented by the formula (I) with 100 wt. parts of another mesomorphic compound as mentioned above which can be composed of two or more species.

Further, when two or more species of the compounds represented by the formulas (I) are used, the two or more species of the compound of the formula (I) may be used in a total amount of 1-500 wt. parts, preferably 2-100 wt. parts, per 100 wt. parts of another mesomorphic compound as described above which can be composed of two or more species.

The ferroelectric liquid crystal device according to the present invention may preferably be prepared by heating the liquid crystal composition prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the ferroelectric liquid crystal device prepared as described above for explanation of the structure thereof.

Referring to FIG. 1, the ferroelectric liquid crystal device includes a ferroelectric liquid crystal layer 1 disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a selection of an organic insulating material or a precursor thereof in a concentration of 0.1 to 20 wt. %, preferably 0.2-10 wt. %, by spinner coating, dip coating, screen printing, spray coating or roller coating, followed by curing or hardening under prescribed hardening condition (e.g., by heating). The insulating alignment control layer may have a thickness of ordinarily 30Å-1 micron, preferably 30-3000 Å, further preferably 50-1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a ferroelectric liquid crystal is sealed up to provide a ferroelectric liquid crystal layer 1 in a thickness of generally 0.5 to 20 microns, preferably 1 to 5 microns.

The ferroelectric liquid crystal provided by the composition of the present invention may desirably assume a SmC* phase (chiral smectic C phase) in a wide temperature range including room temperature (particularly, broad in a lower temperature side) and also shows a wide drive voltage margin and drive temperature margin when contained in a device.

Particularly, in order to show a good alignment characteristic to form a uniform monodomain, the ferroelectric liquid crystal may show a phase transition series comprising isotropic phase-Ch phase (cholesteric phase)-SmA phase (smectic A phase)-SmC* phase (chiral smectic C phase) on temperature decrease.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

Figure 2:
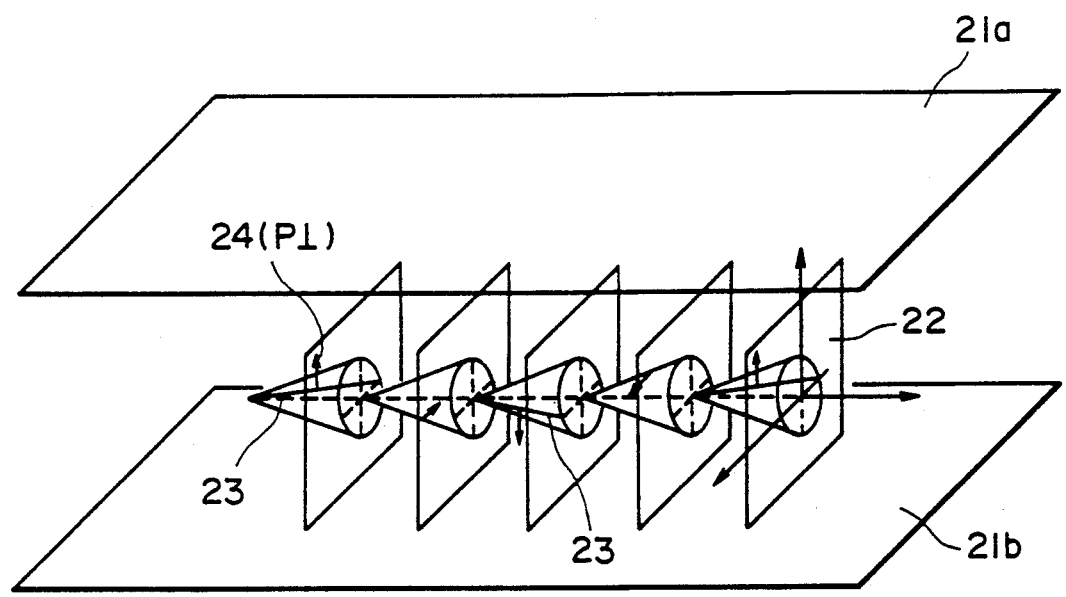
FIGS. 2 and 3 are schematic perspective views of a device cell embodiment for illustrating the operation principle of a ferroelectric liquid crystal device.

FIG. 2 is a schematic illustration of a ferroelectric liquid crystal cell (device) for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment ($P_\perp$) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Figure 3:
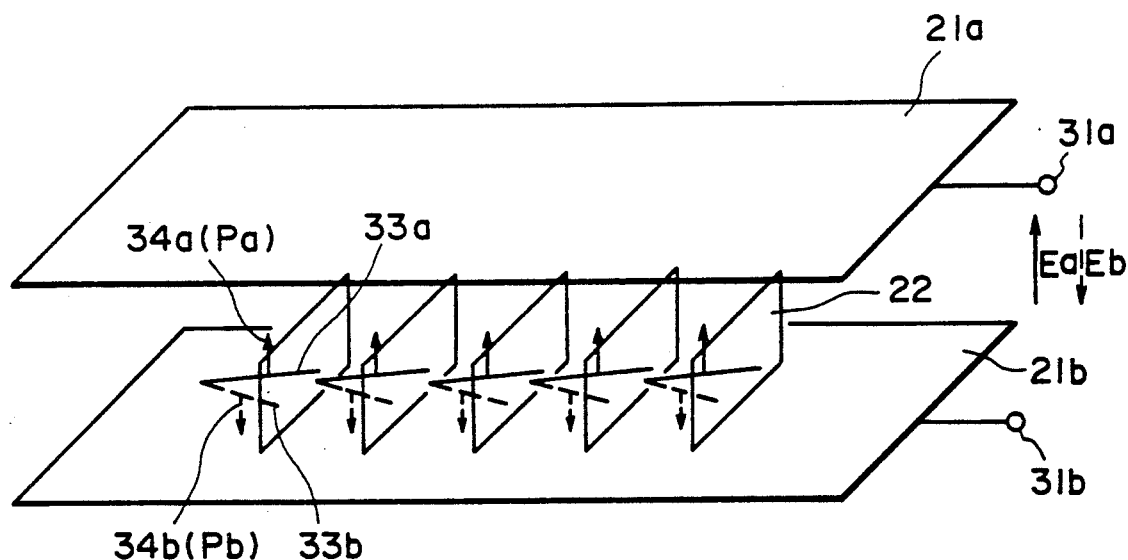

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. The first is that the response speed is quite fast. The second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

When such a ferroelectric liquid crystal device comprising a ferroelectric liquid crystal composition as described above between a pair of electrode plates is constituted as a simple matrix display device, the device may be driven by a driving method as disclosed in Japanese Laid-Open Patent Applications (KOKAI) Nos. 193426/1984, 193427/1984, 156046/1985, 156047/1985, etc.

Hereinbelow, the present invention will be explained more specifically with reference to examples. It is however to be understood that the present invention is not restricted to these examples.

EXAMPLE 1

4-(5-dodecyl-2-pyrimidyl)phenyl 5-hexylthiophene-2-carboxylate (Example Compound No. 1-38 was synthesized through the following steps i)-vi:

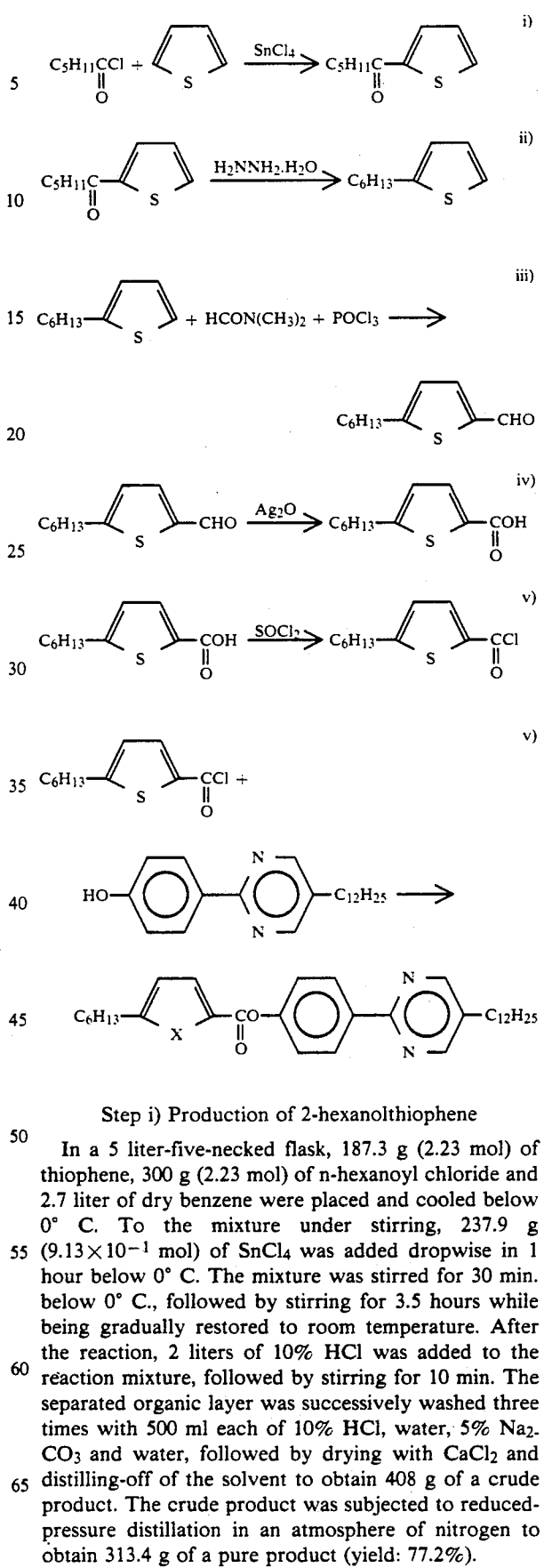

Step i) Production of 2-hexanolthiophene

In a 5 liter-five-necked flask, 187.3 g (2.23 mol) of thiophene, 300 g (2.23 mol) of n-hexanoyl chloride and 2.7 liter of dry benzene were placed and cooled below 0° C. To the mixture under stirring, 237.9 g (9.13×10⁻¹ mol) of SnCl₄ was added dropwise in 1 hour below 0° C. The mixture was stirred for 30 min. below 0° C., followed by stirring for 3.5 hours while being gradually restored to room temperature. After the reaction, 2 liters of 10% HCl was added to the reaction mixture, followed by stirring for 10 min. The separated organic layer was successively washed three times with 500 ml each of 10% HCl, water, 5% Na₂CO₃ and water, followed by drying with CaCl₂ and distilling-off of the solvent to obtain 408 g of a crude product. The crude product was subjected to reduced-pressure distillation in an atmosphere of nitrogen to obtain 313.4 g of a pure product (yield: 77.2%).

Step ii) Production of 2-hexylthiophene

In a 10 liter-five-necked flask, 300 g (1.65 mol) of 2-hexanolthiophene, 582.1 ml of 60% hydrazine hydrate and 5 liters of diethyleneglycol were placed and reacted for 2 hours at 180° C. with distilling-off of excessive water and hydrazine hydrate. The mixture was cooled to 110° C. and 313.7 g of KOH was added thereto, followed by heating again for 2 hours of reaction at 180° C. After the reaction, the reaction mixture was poured into 10 liters of water, extracted two times with 2 liters of isopropyl ether and washed four times with 2 liters of water, followed by drying with CaCl$_2$ and distilling-off of the solvent to obtain 285 g of a crude product. The crude product was subjected to reduced-pressure distillation in an atmosphere of nitrogen to obtain 230 g of a pure product (yield: 83%).

Step iii) Production of 5-hexylthiophene-2-carbaldehyde

In a 3 liter-four-necked flask, 173.7 (2.38 mol) of N,N-dimethylformamide was placed and cooled to 5° C., followed by addition of 201.4 g (1.31 mol) of POCl$_3$ in 15 min below 10° C. under stirring. After stirring for 30 min. below 10° C., 200 g (1.19 mol) of 2-hexylthiophene was added dropwise to the mixture in 10 min. at room temperature, followed by stirring for 1.5 hours and further stirring for 2 hours at 60° C. After the reaction, the reaction mixture was poured into 5 liters of iced water, subjected to 3 times of extraction with 2 liters of chloroform and washed 6 times with 2 liter of water. The organic layer was dried with CaCl$_2$, followed by distilling-off of the solvent and reduced-pressure distillation in an atmosphere of nitrogen to obtain 199.2 g of a product (yield: 85.0%).

Step iv) Production of 5-hexylthiophene-2-carboxylic acid

In a 5 liter-four-necked flask, 90.0 g (4.59×10$^{-1}$ mol) of 5-hexylthiophene-2-carbaldehyde, 540 ml of ethanol and a solution of 171.0 g of AgNO$_3$ in 540 ml of water were placed. A solution of 91.8 g of NaOH in 270 ml of water was added dropwise to the mixture in 30 min. at room temperature, followed by stirring for 1.5 hours. After the reaction, the reaction mixture was subjected to filtration, and the filtrate was acidified with 6N-HCl to precipitate a crystal. The crystal was recovered by filtration to provide a crude product. The product was subjected to recrystallization from 50% hydrous ethanol to obtain 74.5 g of a pure product (yield: 76.6%).

Step v) Production of 5-hexylthiophene-2-carboxylic chloride 10 ml of thionyl chloride was added to 1.0 g (4.72×10$^{-3}$ ml) of 5-hexylthiophene-2-carboxylic acid, followed by stirring for 4 hours under heating at 80° C. and removal of excessive thionyl chloride by reduced-pressure distillation to obtain 5-hexylthiophene-2-carboxylic chloride.

Step vi) Production of 4-(5-dodecyl-2-pyrimidinyl)phenyl 5-hexylthiophene-2-carboxylate 15 ml of pyridine was added to 0.80 g (2.36×10$^{-3}$ mol) of 4-(5-dodecyl-2-pyrimidinyl)phenol, followed by cooling on an iced water bath. To the mixture, 0.54 g (2.36×10$^{-3}$ mol) of 5-hexylthiophene-2-carboxylic chloride was added, followed by stirring for 5 hours at room temperature. After the reaction, the reaction mixture was poured into 100 ml of water and acidified with conc. hydrochloric acid, followed by three times of extraction with 50 ml of isopropyl ether. The organic layer was washed with water repeatedly until the washing liquid reacted neutrality, followed by drying with anhydrous magnesium sulfate and distilling-off of the solvent to obtain a crude product. The crude product was purified by silica gel column chromatography with the use of a hexane/ethyl acetate =10/1 mixture solvent and recrystallized from ethanol to obtain 0.38 g of a pure product (yield: 30.2%).

Phase transition temperature (°C.)

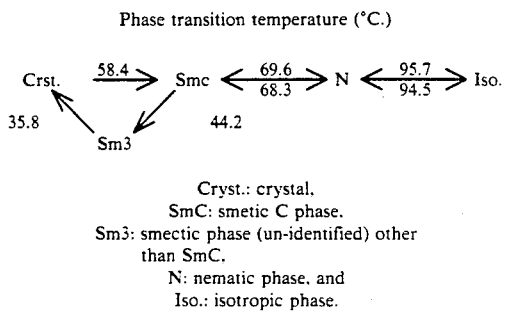

Cryst.: crystal.
SmC: smetic C phase.
Sm3: smectic phase (un-identified) other than SmC.
N: nematic phase. and
Iso.: isotropic phase.

EXAMPLE 2

4-(5-hexyl-2-pyrimidinyl)phenyl 5-hexylthiophene-2-carboxylate (Example Compound No. 1-27) was synthesized in the following manner.

0.36 g of the above compound was prepared in the same manner as in Example 1 except that 4-(5-hexyl-2-pyrimidinyl)phenol was used instead of 4-(5-dodecyl-2-pyrimidinyl)phenol in Step vi) of Example 1 (yield: 34.0%).

Phase transition temperature (°C.)

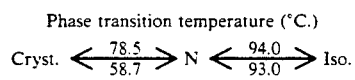

EXAMPLE 3

4-(5-hexyl-2-pyrimidinyl)phenyl 5-dodecylthiophene-2-carboxylate. (Example Compound No. 1-58) was synthesized through the following steps i)–vi:

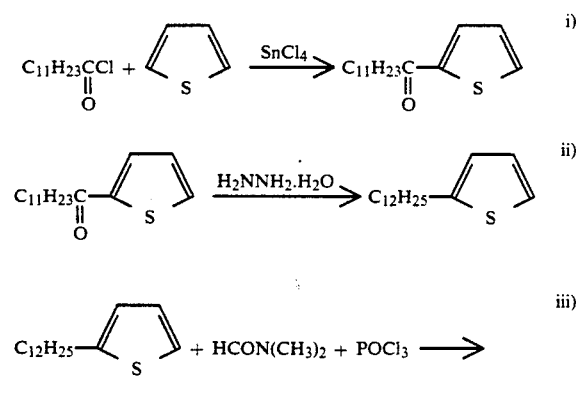

-continued

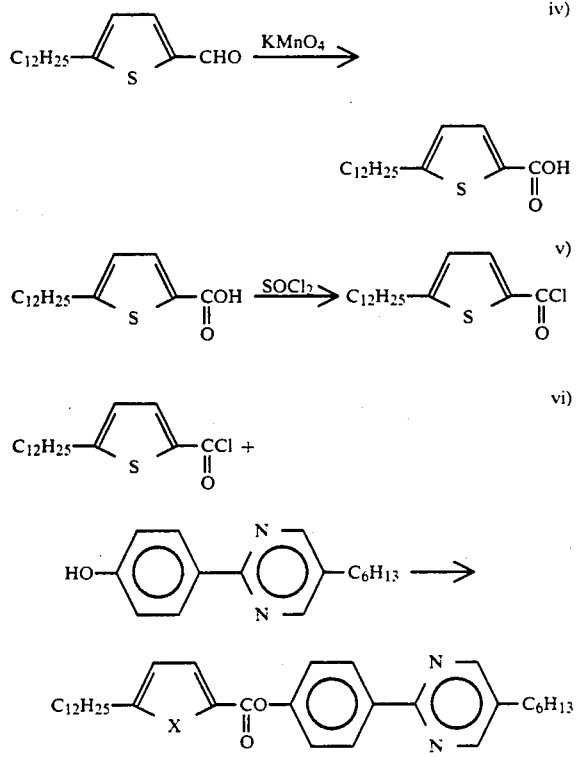

Step i) Production of 2-dodecanoylthiophene

In a 5 liter-five-necked flask, 112.5 g (1.34 mol) of thiophene, 300 g (1.37 mol) of n-dodecanoyl chloride and 2.25 liter of dry benzene were placed and cooled below 0° C. To the mixture under stirring, 148.5 g ($5.70 \times 10^{-1}$ mole) of $SnCl_4$ was added dropwise in 1 hour below 0° C. The mixture was stirred for 30 min. below 0° C., followed by stirring for 4 hours while being gradually restored to room temperature. After the reaction, 2 liter of 10% HCl was added to the reaction mixture, followed by stirring for 10 min. The separated organic layer was successively washed three times with 500 ml each of 10% HCl, water, 5% $Na_2CO_3$ and water, followed by drying with $CaCl_2$ and distilling-off of the solvent to obtain 315 g of a crude product. The crude product was subjected to reduced-pressure distillation under an atmosphere of nitrogen to obtain 270 g of a pure product (yield: 75.7%). b.p.: 146° C./0.65 mmHg

Step ii) Production of 2-dodecylthiophene

In a 5 liter-five-necked flask, 266 g (1.0 mol) of 2-hexanoylthiophene, 392.4 ml of 60% hydrazine hydrate and 3 liter of diethyleneglycol were placed and reacted for 6 hours at 195° C. with distilling-off of excessive water and hydrazine hydrate. The mixture was cooled to 50° C. and 210.6 g of KOH was added thereto, followed by heating again to react for 2.5 hours at 155° C. After the reaction, the reaction mixture was poured into 10 liter of water, extracted two times with 2 liter of isopropyl ether, followed by drying with $CaCl_2$ and distilling-off of the solvent to obtain 229 g of a crude product. The crude product was subjected to reduced-pressure distillation in an atmosphere of nitrogen to obtain 168 g of a pure product (yield: 66.7 b.p.: 121.5° C./0.7 mmHg

Step iii) Production of 5-dodecylthiophene-2-carbaldehyde

In a 1 liter-four-necked flask, 93.7 (1.28 mol) of N,N-dimethylformamide was placed and cooled to 5° C., followed by addition of 107.4 g ($7.00 \times 10^{-1}$ mol) of $POCl_3$ in 15 min. below 10° C. under stirring. After stirring for 30 min. below 10° C., 160 g ($6.35 \times 10^{-1}$ mol) of 2-dodecylthiophene was added dropwise to the mixture in 10 min. at room temperature, followed by stirring for 1.5 hours and further stirring for 2.5 hours at 60° C. After the reaction, the reaction mixture was poured into 2 liters of iced water, subjected to 3 times of extraction with 500 ml of chloroform and washed 6 times with 500 ml of water. The organic layer was dried on $CaCl_2$, followed by distilling-off of the solvent to obtain 237 g of a crude product. The crude product was subjected to reduced-pressure distillation in an atmosphere of nitrogen to obtain 135 g of a product (yield: 75.9%). b.p.: 160° C./0.6 mmHg

Step iv) Production of 5-dodecylthiophene-2-carboxylic acid

In a 2 liter-four-necked flask, 30.0 g ($1.07 \times 10^{-1}$ mol) of 5-dodecylthiophene-2-carbaldehyde, 6.0 g of NaOH, 21.3 g of $KMnO_4$ and 900 ml of water were placed and stirred for 17 hours at room temperature. After the reaction, the reaction mixture was acidified with conc. hydrochloric acid, followed by four times of extraction with 300 ml of ethyl acetate, three times of washing with 500 ml of water, drying with anhydrous magnesium sulfate and distilling-off of the solvent to obtain 29.9 g of a crude product. The crude product was purified by silica gel column chromatography with the use of an hexane/ethyl acetate (=2/1) mixture solvent and recrystallized from ethyl acetate to obtain 12.1 g of a pure product (yield: 38.2%).

Step v) Production of 5-dodecylthiophene-2-carboxylic chloride 4 ml of thionyl chloride was added to 0.57 g ($1.93 \times 10^{-3}$ ml) of 5-dodecylthiophene-2-carboxylic acid, followed by heat-stirring for 4 hours at 70° C. and removal of excessive thionyl chloride by reduced-pressure distillation to obtain 5-dodecylthiophene-2-carboxylic chloride.

Step vi) Production of 4-(5-hexyl-2-pyrimidinyl)phenyl 5-dodecylthiophene-2-carboxylate 15 ml of pyridine was added to 0.49 g ($1.93 \times 10^{-3}$ mol) of 4-(5-hexyl-2-pyrimidinyl)phenol, followed by cooling on an iced water bath. To the mixture, 0.61 g ($1.93 \times 10^{-3}$ mol) of 5-dodecylthiophene-2-carboxylic chloride was added, followed by stirring for 4.5 hours at room temperature. After the reaction, the reaction mixture was poured into 100 ml of water and acidified with conc. hydrochloric acid, followed by three times of extraction with 50 ml of isopropyl ether. The organic layer was washed with water repeatedly until the washing liquid reached neutrality, followed by drying with anhydrous magnesium sulfate and distilling-off of the solvent to obtain a crude product. The crude product was purified by silica gel column chromatography with the use of a hexane/ethyl acetate (=10/1) mixture solvent and recrystallized from an ethanol/ethyl acetate mixture solvent to obtain 0.52 g of a pure product (yield: 50.5%).

Phase transition temperature (°C.)

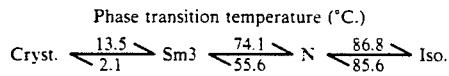

EXAMPLE 4

4-(4'-decylbiphenyl) 5-dodecylthiophene-2-carboxylate (Example Compound No. 1-23) was synthesized in the following manner.

0.44 g of the above compound was prepared in the same manner as in Example 3 except that 4-decyl-4'-hydroxybiphenyl was used instead of 4-(5-hexyl-2-pyrimidinyl)phenol in Step vi) of Example 3 (yield: 43.1%).

Phase transition temperature (°C.)

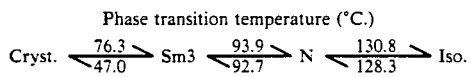

EXAMPLE 5

5-decyl-2-[4-(5-dodecyl-2-thienylcarbonyloxy) phenyl]-1,3,4-thiadiazole (Example Compound No. 1-32) was synthesized in the following manner.

0.60 g of the above compound was prepared in the same manner as in Example 3 except that 5-decyl-2-(4-hydroxyphenyl)-1,3,4-thiadiazole was used instead of 4-(5-hexyl-2-pyrimidinyl)phenol in Step vi) of Example 3 (yield: 60.0%).

Phase transition temperature (°C.)

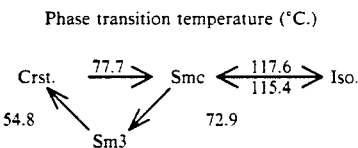

EXAMPLE 6

4-(2'-fluorooctyloxy)phenyl-5-dodecylthiophene-2-carboxylate (Example Compound No. 1-15) was synthesized in the following manner.

0.74 g of the above compound was prepared in the same manner as in Example 3 except that 4-(2'-fluorooctyloxy)phenol was used instead of 4-(5-hexyl-2-pyrimidinyl)phenol in Step vi) of Example 3 (yield: 56.9%).

Phase transition temperature (°C.)

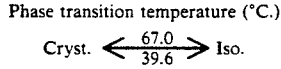

EXAMPLE 7

5-dodecyl-2-(4-octyloxy-β-cyanostyryl) thiophene (Example Compound No. 1-132) was synthesized through the following reaction scheme:

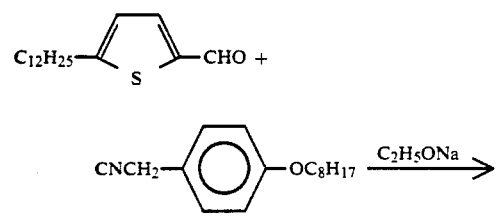

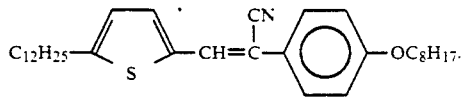

1.0 g ($3.57 \times 10^{-3}$ mol) of 5-dodecylthiophene-2-carbaldehyde obtained through the steps (i)–(iii) in Example 3 and 0.87 g ($3.57 \times 10^{-3}$ mol) of p-octyloxybenzylcyanide were dissolved in 20 ml of ethanol. A solution of 0.01 g metal sodium in 2 ml of ethanol was added to the mixture, which was stirred for 4 hours at room temperature and poured into 200 ml of water. The resultant mixture was acidified with con. hydrochloric acid, followed by three times of extraction with 50 ml of ethyl acetate. The organic layer was washed with water repeatedly until the washing liquid reached neutrality, followed by drying with anhydrous magnesium sulfate, distilling-off of the solvent to obtain a crude product. The crude product was purified by silica gel column chromatography with the use of a hexane/ethyl acetate (=10/1) mixture solvent and recrystallized from hexane to obtain 0.60 g of a pure product (yield: 33.1%).

Phase transition temperature (°C.)

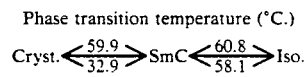

EXAMPLE 8

4-(5-decyloxadiazolyl)phenyl 5-dodecylthiophene-2-carboxylate (Example Compound No. 1-34) was synthesized in the following manner.

0.34 g of the above compound was prepared in the same manner as in Example 3 except that 4-(5-decyloxadiazolyl)phenyl was used instead of 4-(5-hexyl-2-pyrimidinyl)phenol in Step (vi) of Example 3 (yield: 30.2%).

Phase transition temperature (°C.)

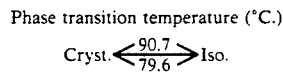

EXAMPLE 9

4-(4'-octylbiphenyl)-5-dodecylthiophene-2-carboxylate (Example Compound No. 1-68) was synthesized in the following manner.

0.45 g of the above compound was prepared in the same manner as in Example 3 except that 4'-octylbiphenyl-4-ol was used instead of 4-(5-hexyl-2-pyrimidinyl)-phenol in Step (vi) of Example 3 (yield: 51.3%).

Phase transition temperature (°C.)

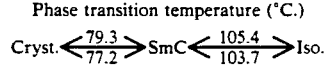

EXAMPLE 10

6-(2'-decyloxycarbonylnaphthalene-5-dodecylthiophene-2-carboxylate (Example Compound No. 1-53) was synthesized in the following manner.

0.60 g of the above compound was prepared in the same manner as in Example 3 except that 2-decyloxycarbonylnaphthalene-6-ol was used instead of 4-(5- hexyl-2-pyrimidinyl)phenol in Step (vi) of Example 3 (yield: 64.9%).

Phase transition temperature (°C.)

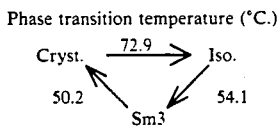

EXAMPLE 11

4'-(4-methylhexyloxy)phenyl-5-dodecylthiophene-2-carboxylate (Example Compound No. 1-12) was synthesized in the following manner.

47 mg of the above compound was prepared in the same manner as in Example 3 except that (4'-4-methylhexyloxy)phenol was used instead of 4-(5-hexyl-2-pyrimidinyl)phenol in Step (vi) of Example 3 (yield: 10.0%).

Phase transition temperature (°C.)

Cryst. $\xrightarrow[22.9]{44.7}$ Iso.

EXAMPLE 12

4-(5-dodecyl-2-pyrimidinyl)phenyl 5-dodecylthiophene-2-carboxylate (Example Compound No. 1-28) was synthesized in the following manner.

0.20 g of the above compound was prepared in the same manner as in Example 3 except that 4-(5-dodecyl-2-pyrimidinyl)phenol was used instead of 4-(5-hexyl-2-pyrimidinyl)phenol in Step (vi) of Example 3 (yield: 43.0%).

Phase transition temperature (°C.)

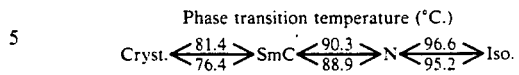

EXAMPLE 13

4-(4'-decylbiphenyl)-5-dodecylthiophene-2-carboxylate (Example Compound No. 1-30) was synthesized through the following manner. 0.70 g of the above compound was prepared in the same manner as in Example 3 except that 4'-decylbiphenyl-4-ol was used instead of 4-(5-hexyl-2-pyrimidinyl)phenol in Step (vi) of Example 3 (yield: 73.0%).

Phase transition temperature (°C.)

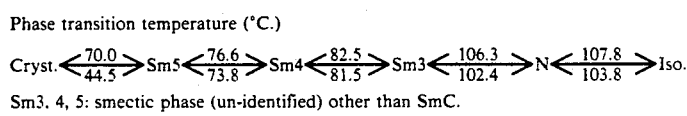

Sm3, 4, 5: smectic phase (un-identified) other than SmC.

EXAMPLE 14

A liquid crystal composition A was prepared by mixing the following compounds in respectively indicated proportions.

| Ex. Comp. No. | Structural formula | wt. parts |
|---|---|---|
| 18 | C$_8$H$_{17}$O—⟨◯⟩—CO—⟨◯⟩—OCH$_2$*CHC$_2$H$_5$ (CH$_3$) ‖O | 56 |
| 8 | C$_8$H$_{17}$O—⟨◯⟩—OC—⟨◯⟩—⟨◯⟩—CH$_2$*CHC$_2$H$_5$ (CH$_3$) ‖O | 14 |
| 124 | C$_{12}$H$_{25}$O—⟨◯⟩—CO—⟨◯⟩—OCH$_2$*CHC$_6$H$_{13}$ (F) ‖O | 7.5 |
| 136 | C$_8$H$_{17}$O—⟨◯⟩—CO—⟨◯⟩—OCH$_2$*CHC$_5$H$_{11}$ (F) ‖O | 22.5 |

The liquid crystal composition A showed the following phase transition series (the numerals denote phase transition temperatures (°C.)). The same as in the Examples appearing hereinafter).

Cryst. $\xrightarrow[21.9]{23.6}$ SmC* $\xrightarrow[48.0]{48.7}$ SmA $\xrightarrow[68.0]{68.7}$ Ch. $\xrightarrow[77.8]{78.4}$ Iso.

The liquid crystal composition A was further mixed with Example Compound No. 1-38 explained in the formerly described Example 1 in the proportions indicated below to provide a liquid crystal composition B.

| Ex. Comp. No. | Structural formula | wt. parts |
|---|---|---|
| 1-38 | 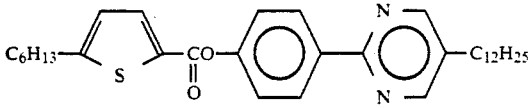 | 10 |
| | Composition A | 90 |

The liquid crystal composition B showed the following phase transition series.

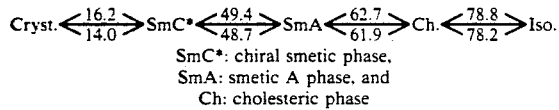

SmC*: chiral smetic phase,
SmA: smetic A phase, and
Ch: cholesteric phase

As is understood from the comparison between the liquid crystal compositions A and B, the liquid crystal composition B containing the compound of Example Compound No. 1-38 according to the present invention showed a wide SmC* temperature range which was particularly enlarged in the lower temperature side. Further, the liquid crystal B was effective in enlargement of the cholesteric temperature range.

EXAMPLE 15

Two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition B prepared in Example 14 was heated into an isotropic liquid, and injected into the above prepared cell under vacuum and, after sealing, was gradually cooled at a rate of 20° C./hour to 25° C. to prepare a ferroelectric liquid crystal device.

The ferroelectric liquid crystal device was subjected to measurement of a spontaneous polarization Ps and an optical response time (time from voltage application until the transmittance change reaches 90% of the maximum under the application of a peak-to-peak voltage Vpp of 20 V in combination with right-angle cross-nicol polarizers).

| | 25° C. | 35° C. | 45° C. |
|---|---|---|---|
| Response time (μsec) | 332 | 169 | 87 |
| Ps (nC/cm²) | 31.1 | 21.7 | 10.2 |

Further, the device was driven at 25° C. to provide a contrast of 14.2 and a clear switching action was observed.

COMPARATIVE EXAMPLE 15

A ferroelectric liquid crystal device was prepared in the same manner as in Example 15 except that the liquid crystal composition A prepared in Example 14 was injected into a cell. The measured values of Ps and the response time of the device were as follows.

| | 25° C. | 35° C. | 45° C. |
|---|---|---|---|
| Response time (μsec) | 430 | 150 | 60 |
| Ps (nC/cm²) | 36.5 | 26.2 | 13.3 |

As is understood from the comparison between Example 15 and Comparative Example 15, a ferroelectric liquid crystal device using the liquid crystal composition B containing the mesomorphic compound according to the present invention showed a longer response time at high temperature and a shorter response time at low temperature. The ratio of the response time at 25° C. to that at 45° C. was 7.3 to 1 for the device using the liquid crystal composition A and 3.8 to 1 for the device using the liquid crystal composition B, i.e., the response time ratio of the latter to the former was about 1–2, so that the liquid crystal device according to the present invention provided a remarkably improved temperature-dependence of the response speed (ratio of response time (25° C./45° C.)).

EXAMPLE 16

A liquid crystal composition C was prepared in the same manner as in Example 14 except that Example Compound No. 1-27 was used instead of Example Compound No. 1-38.

The liquid crystal composition C showed the following phase transition series.

A ferroelectric liquid crystal device was prepared in the same manner as in Example 15 except for using the liquid crystal composition C. In the ferroelectric liquid crystal device, a monodomain with a good and uniform alignment characteristic was observed. The ferroelectric liquid crystal device was subjected to measurement of response time and spontaneous polarization Ps in the same manner as in Example 15, whereby the following results were obtained.

|  | 25° C. | 35° C. | 45° C. |
|---|---|---|---|
| Response time (μsec) | 406 | 211 | 127 |
| Ps (nC/cm²) | 33.3 | 24.4 | 12.2 |

EXAMPLE 17

A liquid crystal composition C was prepared in the same manner as in Example 14 except that Example Compound No. 1-58 was used instead of Example Compound No. 1-38.

The liquid crystal composition D showed the following phase transition series.

$$\text{Cryst.} \underset{14.1}{\overset{16.3}{\rightleftarrows}} \text{SmC*} \underset{47.5}{\overset{48.2}{\rightleftarrows}} \text{SmA} \underset{59.9}{\overset{60.8}{\rightleftarrows}} \text{Ch.} \underset{77.6}{\overset{78.3}{\rightleftarrows}} \text{Iso.}$$

A ferroelectric liquid crystal device was prepared in the same manner as in Example 15 except for using the liquid crystal composition D. In the ferroelectric liquid crystal device, a monodomain with a good and uniform alignment characteristic was observed. The ferroelectric liquid crystal device was subjected to measurement of response time and spontaneous polarization Ps in the same manner as in Example 15, whereby the following results were obtained.

|  | 25° C. | 35° C. | 45° C. |
|---|---|---|---|
| Response time (μsec) | 339 | 168 | 88 |
| Ps (nC/cm²) | 30.7 | 20.8 | 7.91 |

EXAMPLES 18–23

Liquid crystal compositions E to J were prepared by replacing the Example Compounds and the liquid crystal compositions used in Example 14 with Example Compounds and liquid crystal compositions shown in the following Table 1. Ferroelectric liquid crystal devices were prepared in the same manner as in Example 15 by respectively using these compositions instead of the composition B, and subjected to measurement of optical response time and observation of switching states. In the devices, a monodomain with a good and uniform alignment characteristic was observed. The results of the measurement are shown in the following Table 1.

TABLE 1

| Ex. No. (Comp. Name) | Example Compound No. or liquid crystal composition name (weight parts) | | | | Response time (μsec) | | |
|---|---|---|---|---|---|---|---|
|  |  |  |  |  | 25° C. | 35° C. | 45° C. |
| 18 (E) | 1-23 (5) | 1-37 (5) |  | A (90) | 329 | 158 | 72 |
| 19 (F) | 1-21 (5) | 1-32 (3) | 1-55 (2) | A (90) | 287 | 118 | 56 |
| 20 (G) | 1-19 (7) | 1-59 (5) |  | A (88) | 232 | 108 | 47 |
| 21 (H) | 1-60 (8) | 1-98 (4) |  | A (88) | 334 | 142 | 78 |
| 22 (I) | 1-125 (5) | 1-104 (3) |  | A (92) | 325 | 130 | 67 |
| 23 (J) | 1-27 (6) | 1-137 (3) |  | A (91) | 212 | 104 | 45 |

As is apparent from the results shown in the above Table 1, the ferroelectric liquid crystal devices containing the liquid crystal compositions E to J provided a decreased temperature dependence of the response speed.

EXAMPLE 24

A liquid crystal composition K was prepared by mixing the following compounds in respectively indicated proportions.

| Ex. Comp. No. | Structural formula | wt. parts |
|---|---|---|
| 20 |  $C_{10}H_{21}O-\langle N=N \rangle-\langle \rangle-O+CH_2\}_3\overset{CH_3}{\underset{*}{C}H}C_2H_5$ | 15 |
| 21 | 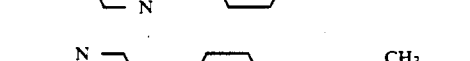 $C_8H_{17}-\langle N=N \rangle-\langle \rangle-O+CH_2\}_3\overset{CH_3}{\underset{*}{C}H}C_2H_5$ | 15 |
| 58 |  $C_8H_{17}-\langle N=N \rangle-\langle \rangle-O+CH_2\}_3\overset{CH_3}{\underset{*}{C}H}OC_5H_{11}$ | 10 |
| 89 |  $C_{10}H_{21}-\langle N=N \rangle-\langle \rangle-O+CH_2\}_3\overset{CH_3}{\underset{*}{C}H}OC_3H_7$ | 20 |
| 120 |  $C_{10}H_{21}-\langle N=N \rangle-\langle \rangle-OC(O)-\langle \rangle-OCH_2\overset{F}{\underset{*}{C}H}C_6H_{13}$ | 13 |

| Ex. Comp. No. | Structural formula | wt. parts |
|---|---|---|
| 129 | C₁₀H₂₁–[pyrazine]–[phenyl]–OCH₂C*HC₈H₁₇ (F substituent) | 7 |
| 236 | C₃H₇–[cyclohexyl(H)]–CO-O–[phenyl]–[pyrimidine]–C₁₂H₂₅ | 15 |
| 242 | C₅H₁₁–[cyclohexyl(H)]–CH₂O–[phenyl]–[pyrimidine]–C₆H₁₃ | 5 |

The liquid crystal composition K was further mixed with the following compounds in respectively indicated proportions to provide a liquid crystal composition L.

| Ex. Comp. No. | Structural formula | wt. parts |
|---|---|---|
| I-27 | n-C₆H₁₃–[thiophene]–CO-O–[phenyl]–[pyrimidine]–C₆H₁₃-n | 4 |
| I-59 | n-C₃H₇–[thiophene]–CO-O–[phenyl]–[pyrimidine]–OC₁₂H₂₅-n | 4 |
| I-33 | n-C₇H₁₅CO–[thiophene]–CO-O–[phenyl]–[thiadiazole]–C₅H₁₁-n | 6 |
| Composition K | | 86 |

A ferroelectric liquid crystal device was prepared in the same manner as in Example 15 except for using the composition L. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

|  | 15° C. | 25° C. | 35° C. |
|---|---|---|---|
| Response time (μsec) | 165 | 130 | 100 |

Further, the device was driven at 25° C. to provide a contrast of 19, a clear switching action was observed, and good bistability was shown after the termination of the voltage application.

COMPARATIVE EXAMPLE 24

A ferroelectric liquid crystal device was prepared in the same manner as in Example 15 except that the liquid crystal composition K prepared in Example 24 was injected into a cell. The measured values of the response time of the device were as follows.

|  | 15° C. | 25° C. | 35° C. |
|---|---|---|---|
| Response time (μsec) | 155 | 100 | 80 |

EXAMPLE 25

A liquid crystal composition M was prepared by mixing the following Example Compounds in the respectively indicated proportions with the liquid crystal composition K prepared in Example 24.

| Ex. Comp. No. | Structural formula | wt. parts |
|---|---|---|
| I-26 |  | 6 |

-continued

| Ex. Comp. No. | Structural formula | wt. parts |
|---|---|---|
| 1-89 | $C_2H_5\overset{*}{C}H(CH_3)(CH_2)_3$—[thiophene]—CH=CH—CH$_2$O—[phenyl]—[pyrimidine]—$C_{10}H_{21}$-n | 6 |
| 1-85 | n-$C_5H_{11}$—[thiophene]—CH=CH—CH$_2$O—[phenyl]—[phenyl]—$C_{12}H_{25}$-n | 4 |
| Composition K | | 84 |

A ferroelectric liquid crystal device was prepared in the same manner as in Example 15 except for using the composition M. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

|  | 15° C. | 25° C. | 35° C. |
|---|---|---|---|
| Response time (μsec) | 160 | 130 | 95 |

Further, the device was driven at 25° C. to provide a contrast of 18, a clear switching action was observed, and good bistability was shown after the termination of the voltage application.

EXAMPLE 26

A liquid crystal composition N was prepared by mixing the following Example Compounds in the respectively indicated proportions with the liquid crystal composition K prepared in Example 24.

A ferroelectric liquid crystal device was prepared in the same manner as in Example 15 except for using the composition N. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

|  | 15° C. | 25° C. | 35° C. |
|---|---|---|---|
| Response time (μsec) | 145 | 105 | 85 |

Further, the device was driven at 25° C. to provide a contrast of 18, a clear switching action was observed, and good bistability was shown after the termination of the voltage application.

EXAMPLE 27

A liquid crystal composition O was prepared by mixing the following compounds in respectively indicated proportions.

| Ex. Comp. No. | Structural formula | wt. parts |
|---|---|---|
| 1-11 | n-$C_6H_{13}$C(=O)—[thiophene]—CH=CH—CO—[phenyl]—O$C_6H_{13}$-n | 4 |
| 1-38 | n-$C_6H_{13}$—[thiophene]—CH=CH—CO—[phenyl]—[pyrimidine]—$C_{12}H_{25}$-n | 8 |
| 1-131 | n-$C_8H_{17}$—[thiophene]—CH=CH—CH=C(CN)—[phenyl]—$C_{10}H_{21}$-n | 3 |
| Composition K | | 85 |

| Ex. Comp. No. | Structural formula | wt. parts |
|---|---|---|
| 18 | $C_8H_{17}$O—[phenyl]—CO—[phenyl]—OCH$_2\overset{*}{C}H(CH_3)C_2H_5$ | 64 |

-continued

| Ex. Comp. No. | Structural formula | wt. parts |
|---|---|---|
| 8 | C$_8$H$_{17}$O–⟨⟩–OC(=O)–⟨⟩–⟨⟩–CH$_2$C*H(CH$_3$)C$_2$H$_5$ | 16 |
| 9 | C$_8$H$_{17}$O–⟨⟩–C(=O)S–⟨⟩–CH$_2$C*H(CH$_3$)C$_2$H$_5$ | 22.5 |
| 43 | C$_{10}$H$_{21}$O–⟨⟩–C(=O)S–⟨⟩–OCH$_2$C*H(CH$_3$)C$_2$H$_5$ | 22.5 |
| 63 | C$_{10}$H$_{21}$OC(=O)–⟨⟩–⟨⟩–OC(=O)–⟨⟩–OCH$_2$C*H(CH$_3$)OC$_5$H$_{11}$ | 15 |
| 87 | C$_6$H$_{13}$OC(=O)–⟨⟩–⟨⟩–OC(=O)–⟨⟩–OCH$_2$C*H(CH$_3$)OC$_8$H$_{17}$ | 15 |
| 124 | C$_{12}$H$_{25}$O–⟨⟩–C(=O)O–⟨⟩–OCH$_2$C*H(F)C$_6$H$_{13}$ | 6.75 |
| 136 | C$_8$H$_{17}$O–⟨⟩–C(=O)O–⟨⟩–OCH$_2$C*H(F)C$_5$H$_{11}$ | 18.75 |
| 236 | C$_3$H$_7$–⟨H⟩–C(=O)O–⟨⟩–⟨pyrimidine⟩–C$_{12}$H$_{25}$ | 20 |
| 23 | C$_8$H$_{17}$–⟨pyrimidine⟩–⟨⟩–O(CH$_2$)$_3$C*H(CH$_3$)C$_2$H$_5$ | 10 |
| 24 | C$_{11}$H$_{23}$O–⟨pyrimidine⟩–⟨⟩–O(CH$_2$)$_2$C*H(CH$_3$)C$_2$H$_5$ | 10 |

The liquid crystal composition O was further mixed with the following compounds in respectively indicated proportions to provide a liquid crystal composition P.

| Ex. Comp. No. | Structural formula | wt. parts |
|---|---|---|
| 1-27 | n-C$_6$H$_{13}$–⟨thiophene-S⟩–C(=O)O–⟨⟩–⟨pyrimidine⟩–C$_6$H$_{13}$-n | 8 |

| Ex. Comp. No. | Structural formula | wt. parts |
|---|---|---|
| 1-59 | n-C$_3$H$_7$—[thiophene]—CO-O—[phenyl]—[pyrimidine N,N]—OC$_{12}$H$_{25}$-n | 5 |
| 1-33 | n-C$_7$H$_{15}$C(=O)—[thiophene]—CO-O—[phenyl]—[thiadiazole N—N, S]—C$_5$H$_{11}$-n | 3 |
| Composition O | | 84 |

A ferroelectric liquid crystal device was prepared in the same manner as in Example 15 except for using the composition P. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

| | 10° C. | 25° C. | 35° C. |
|---|---|---|---|
| Response time (μsec) | 700 | 350 | 245 |

Further, the device was driven at 25° C. to provide a contrast of 17, a clear switching action was observed, and good bistability was shown after the termination of the voltage application.

COMPARATIVE EXAMPLE 27

A ferroelectric liquid crystal device was prepared in the same manner as in Example 15 except that the liquid crystal composition O prepared in Example 27 was injected into a cell. The measured value of the response time of the device were as follows.

| | 10° C. | 25° C. | 35° C. |
|---|---|---|---|
| Response time (μsec) | 635 | 270 | 195 |

EXAMPLE 28

A liquid crystal composition Q was prepared by mixing the following Example Compounds in the respectively indicated proportions with the liquid crystal composition O prepared in Example 27.

| Ex. Comp. No. | Structural formula | wt. parts |
|---|---|---|
| 1-57 | n-C$_8$H$_{17}$—[thiophene]—CO-O—[naphthyl]—OC$_6$H$_{13}$-n | 4 |
| 1-98 | n-C$_5$H$_{11}$—[thiophene]—CH$_2$O—[phenyl]—[pyrimidine N,N]—C$_6$H$_{13}$-n | 6 |
| Composition O | | 90 |

A ferroelectric liquid crystal device was prepared in the same manner as in Example 15 except for using the composition Q. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

| | 10° C. | 25° C. | 35° C. |
|---|---|---|---|
| Response time (μsec) | 680 | 345 | 235 |

Further, the device was driven at 25° C. to provide a contrast of 17, a clear switching action was observed, and good bistability was shown after the termination of the voltage application.

EXAMPLE 29

A liquid crystal composition R was prepared by mixing the following Example Compounds in the respectively indicated proportions with the liquid crystal composition O prepared in Example 27.

| Ex. Comp. No. | Structural formula | wt. parts |
|---|---|---|
| 1-3 | n-$C_{12}H_{25}C$—[thiophene]—CO—O—[phenyl]—$C_3H_7$-n | 7 |
| 1-137 | n-$C_5H_{11}$—[thiophene]—CH=C(CN)—[phenyl]—[phenyl]—$OC_{10}H_{21}$-n | 5 |
| Composition O | | 88 |

A ferroelectric liquid crystal device was prepared in the same manner as in Example 15 except for using the composition R. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

| | 10° C. | 25° C. | 35° C. |
|---|---|---|---|
| Response time (μsec) | 585 | 295 | 200 |

Further, the device was driven at 25° C. to provide a contrast of 16, a clear switching action was observed, and good bistability was shown after the termination of the voltage application.

EXAMPLE 30

A blank cell was prepared in the same manner as in Example 15 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition B prepared in Example 14. The liquid crystal device was subjected to measurement of optical response time in the same manner as in Example 15 The results are shown below.

| | 25° C. | 35° C. | 45° C. |
|---|---|---|---|
| Response time (μsec) | 325 | 165 | 81 |

Further, the device was driven at 25° C. to provide a contrast of 19.

EXAMPLE 31

A blank cell was prepared in the same manner as in Example 15 except for omitting the SiO2 layer to form an alignment control layer composed of the polyimide resin layer alone on each electrode plate. A ferroelectric liquid crystal device was prepared by filling the blank cell with the liquid crystal composition B prepared in Example 14. The liquid crystal device was subjected to measurement of optical response time in the same manner as in Example 15. The results are shown below.

| | 25° C. | 35° C. | 45° C. |
|---|---|---|---|
| Response time (μsec) | 315 | 158 | 82 |

As is apparent from the above Examples 30 and 31, also in the cases of different device structures, the devices containing the ferroelectric liquid crystal composition B according to the present invention respectively provided a remarkably improved operation characteristic at a lower temperature and also a decreased temperature-dependence of the response speed.

EXAMPLE 32

4-(5-nonyloxy-2-pyrimidinyl)phenyl 5-hexylthiophene-2-carboxylate (Example Compound No. 1-183) was synthesized in the following manner.

0.85 g of the above compound was prepared in the same manner as in Example 1 except that 4-(5-nonyloxy-2-pyrimidinyl)phenol was used instead of 4-(5-dodecyl-2-pyrimidinyl)phenol in Step (vi) of Example 1 (yield: 71.7%).

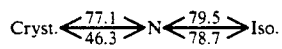

EXAMPLE 33

A liquid crystal composition S was prepared by mixing the following compounds in respectively indicated proportions.

| Ex. Comp. No. | Structural formula | wt. parts |
|---|---|---|
| 173 | $C_6H_{13}O$—[phenyl]—[pyrimidine N,N]—$C_8H_{17}$ | 51.57 |

| Ex. Comp. No. | Structural formula | wt. parts |
|---|---|---|
| 174 | C₉H₁₉O—⟨⟩—⟨N,N⟩—C₈H₁₇ | 25.79 |
| 247 | C₈H₁₇O—⟨⟩—⟨N,N⟩—C₁₀H₂₁ | 12.89 |
| 233 | C₃H₇—⟨H⟩—CO(=O)O—⟨⟩—⟨N,N⟩—C₁₁H₂₃ | 1.19 |
| 258 | C₄H₉—⟨H⟩—CO(=O)O—⟨⟩—⟨N,N⟩—C₁₁H₂₃ | 1.19 |
| 234 | C₅H₁₁—⟨H⟩—CO(=O)O—⟨⟩—⟨N,N⟩—C₁₁H₂₃ | 2.37 |
| 266 | C₁₂H₂₅—⟨N,N⟩—⟨⟩—OCH₂C*HFC₆H₁₃ | 2.50 |
| 150 | C₁₀H₂₁—⟨N,N⟩—⟨⟩—OCH₂C*HFC₆H₁₃ | 2.50 |

The liquid crystal composition S was further mixed with the following compound in respectively indicated proportions to provide a liquid crystal composition T.

| Ex. Comp. No. | Structural formula | wt. parts |
|---|---|---|
| 1-183 | n-C₆H₁₃—⟨S⟩—CH=CH—CO(=O)O—⟨⟩—⟨N,N⟩—C₉H₁₉-n | 10 |
| | Composition S | 90 |

A ferroelectric liquid crystal device was prepared in the same manner as in Example 15 except for using the composition T. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

|  | 10° C. | 30° C. | 40° C. |
|---|---|---|---|
| Response time (μsec) | 670 | 310 | 225 |

COMPARATIVE EXAMPLE 33

A liquid crystal composition U was prepared in the same manner as in Example 33 except for using the following compound (Example Compound No. 252) instead of the above compound (Example Compound No. 1-183).

| Ex. Comp. No. | Structural formula | wt. parts |
|---|---|---|
| 252 |  | 10 |
| | Composition S | 90 |

A ferroelectric liquid crystal device was prepared in the same manner as in Example 15 except for using the tively indicated proportions with the liquid crystal composition S prepared in Example 33.

| Ex. Comp. No. | Structural formula | wt. parts |
|---|---|---|
| 1-149 | | 4 |
| 1-162 | | 6 |
| 1-174 | | 2 |
| | Composition S | 88 | composition U. The ferroelectric liquid crystal device was subjected to measurement of response time in the same manner as in Example 15, whereby the following results were obtained.

| | 10° C. | 30° C. | 40° C. |
|---|---|---|---|
| Response time (μsec) | 735 | 330 | 235 |

As is understood from the comparison between Example 33 and Comparative Example 33, a ferroelectric liquid crystal device using the liquid crystal composition T containing the compound having thiophene ring according to the present invention compared with that using the liquid crystal composition U containing the conventional alkylbenzoic ester-type compound showed a particularly improved response time at low temperature and a decreased temperature-dependence of the response speed (ratio of response time (10° C./40° C.)).

EXAMPLE 34

A liquid crystal composition V was prepared by mixing the following Example Compounds in the respec- A ferroelectric liquid crystal device was prepared in the same manner as in Example 15 except for using the composition V. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

| | 10° C. | 30° C. | 40° C. |
|---|---|---|---|
| Response time (μsec) | 610 | 290 | 210 |

Further, when the device was driven, a clear switching action was observed, and good bistability was shown after the termination of the voltage application.

EXAMPLE 35

A liquid crystal composition W was prepared by mixing the following Example Compounds in the respectively indicated proportions with the liquid crystal composition S prepared in Example 33.

| Ex. Comp. No. | Structural formula | wt. parts |
|---|---|---|
| 1-22 | | 3 |

-continued

| Ex. Comp. No. | Structural formula | wt. parts |
|---|---|---|
| 1-147 | n-$C_3H_7$—[thiophene]—CO-O—[phenyl]—[pyrazine]—$C_9H_{19}$-n | 5 |
| 1-180 | n-$C_4H_9$—[thiophene]—CO-O—[phenyl]—[pyrazine]—$OC_{11}H_{23}$-n | 2 |
| Composition S | | 90 |

A ferroelectric liquid crystal device was prepared in the same manner as in Example 15 except for using the composition W. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

|  | 10° C. | 30° C. | 40° C. |
|---|---|---|---|
| Response time (μsec) | 630 | 290 | 220 |

Further, when the device was driven, a clear switching action was observed, and good bistability was shown after the termination of the voltage application.

EXAMPLE 36

A liquid crystal composition X was prepared by mixing the following Example Compounds in the respectively indicated proportions with the liquid crystal composition S prepared in Example 33.

A ferroelectric liquid crystal device was prepared in the same manner as in Example 15 except for using the composition X. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

|  | 10° C. | 30° C. | 40° C. |
|---|---|---|---|
| Response time (μsec) | 570 | 260 | 195 |

Further, when the device was driven, a clear switching action was observed, and good bistability was shown after the termination of the voltage application.

EXAMPLE 37

A liquid crystal composition Y was prepared by mixing the following Example Compounds in the respectively indicated proportions with the liquid crystal composition S prepared in Example 33.

| Ex. Comp. No. | Structural formula | wt. parts |
|---|---|---|
| 1-5 | n-$C_3H_7$—[thiophene]—CO-O—[phenyl]—$OCC_{12}H_{25}$-n | 2 |
| 1-153 | n-$C_4H_9$—[thiophene]—CO-O—[phenyl]—[pyrazine]—$C_{12}H_{25}$-n | 4 |
| 1-158 | n-$C_6H_{13}$—[thiophene]—CO-O—[phenyl]—[pyrazine]—$C_{10}H_{21}$-n | 4 |
| Composition S | | 90 |

| Ex. Comp. No. | Structural formula | wt. parts |
|---|---|---|
| 1-9 | n-$C_3H_7$—[thiophene]—CO-O—[phenyl]—$OCOC_8H_{17}$-n | 2 |

| Ex. Comp. No. | Structural formula | wt. parts |
|---|---|---|
| 1-57 | 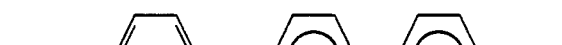 | 4 |
| 1-152 | | 5 |
| 1-166 | | 5 |
| | Composition S | 84 |

A ferroelectric liquid crystal device was prepared in the same manner as in Example 15 except for using the composition Y. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

| | 10° C. | 30° C. | 40° C. |
|---|---|---|---|
| Response time (μsec) | 555 | 250 | 185 |

Further, when the device was driven, a clear switching action was observed, and good bistability was shown after the termination of the voltage application.

EXAMPLE 38

A liquid crystal composition Z was prepared by mixing the following Example Compounds in the respectively indicated proportions with the liquid crystal composition S prepared in Example 33.

| Ex. Comp. No. | Structural formula | wt. parts |
|---|---|---|
| 1-21 |  | 4 |
| 1-58 | | 6 |
| 1-188 | | 4 |
| | Composition S | 86 |

A ferroelectric liquid crystal device was prepared in the same manner as in Example 15 except for using the composition Z. In the ferroelectric liquid crystal device, a monodomain with a good and uniform alignment characteristic was observed. The ferroelectric liquid crystal device was subjected to measurement of response time and observation of a switching state, etc. in the same manner as in Example 15, whereby the following results were obtained.

| | 10° C. | 30° C. | 40° C. |
|---|---|---|---|
| Response time (μsec) | 640 | 310 | 225 |

Further, when the device was driven, a clear switching action was observed, and good bistability was shown after the termination of the voltage application.

EFFECT OF THE INVENTION

As described above, according to the present invention, there are provided a ferroelectric liquid crystal composition and a ferroelectric liquid crystal device containing the composition, which shows a good switching characteristic, an improved low-temperature operation characteristic and a decreased temperature-dependence of response speed.

What is claimed is:

1. A mesomorphic compound represented by the following formula (I):

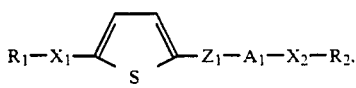 (I)

wherein $R_1$ and $R_2$ respectively denote a linear or branched alkyl group having 1-18 carbon atoms which are unsubstituted or substituted with fluorine or alkoxy group; $X_1$ denotes any one of a single bond, —O—,

$X_2$ denotes any one of a single bond, —O—,

$Z_1$ denotes any one of

—CH$_2$O— and —CH=C(CN)—; and $A_1$ denotes —A$_2$— or —A$_2$—A$_3$— wherein $A_2$ and $A_3$ respectively denote any one of

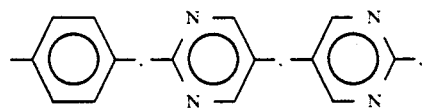

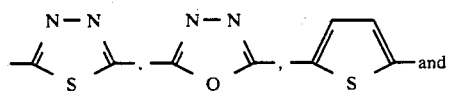

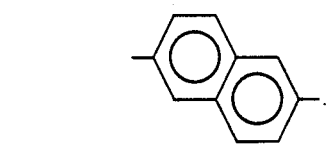

2. A mesomorphic compound according to claim 1, which is represented by any one of the following formula (1-1) to (1-190):

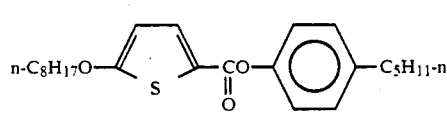 (1-1)

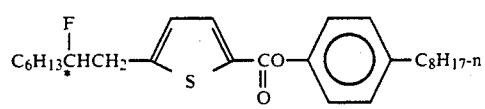 (1-2)

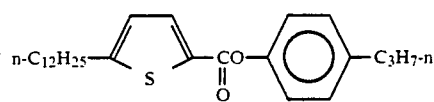 (1-3)

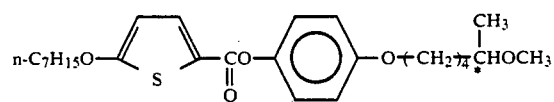 (1-4)

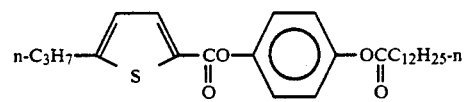 (1-5)

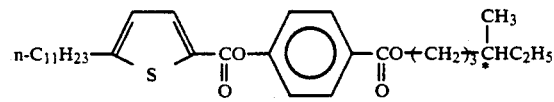 (1-6)

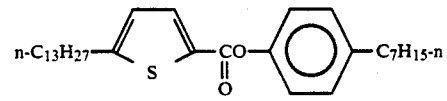 (1-7)

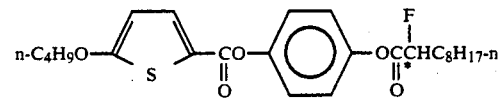 (1-8)

-continued
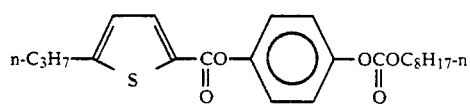 (1-9)
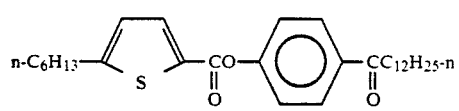 (1-10)
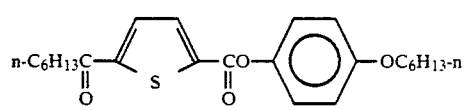 (1-11)
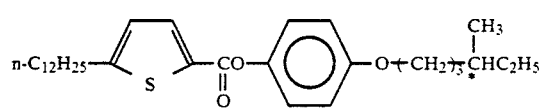 (1-12)
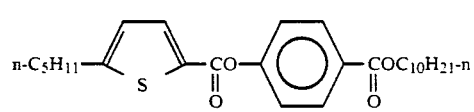 (1-13)
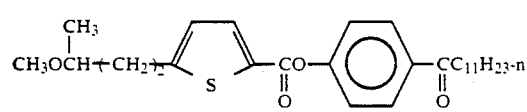 (1-14)
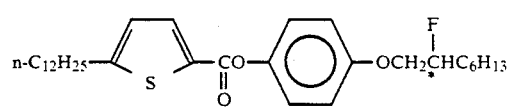 (1-15)
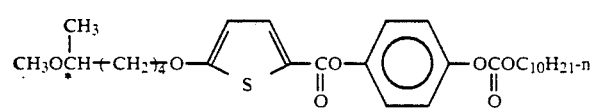 (1-16)
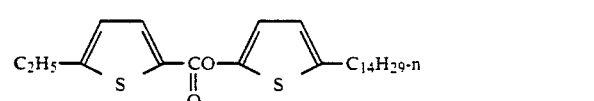 (1-17)
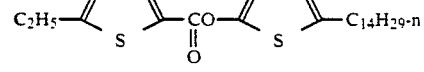 (1-18)
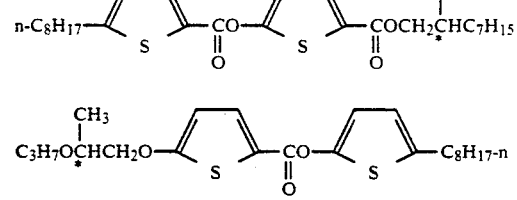 (1-19)
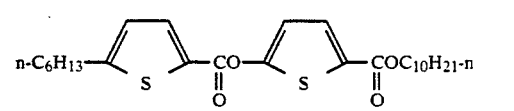 (1-20)
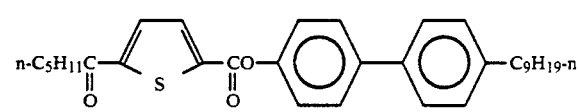 (1-21)
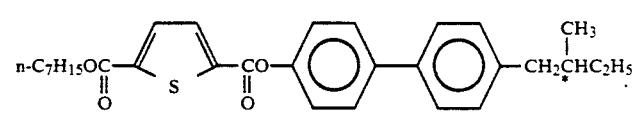 (1-22)

-continued
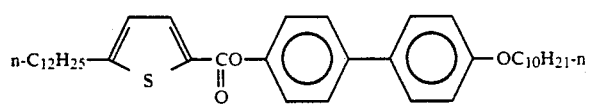 (1-23)
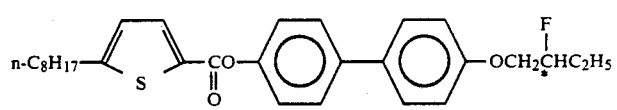 (1-24)
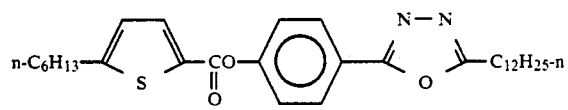 (1-25)
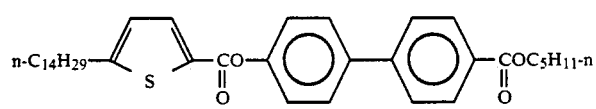 (1-26)
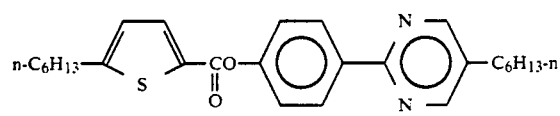 (1-27)
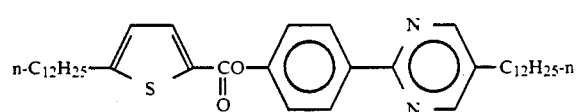 (1-28)
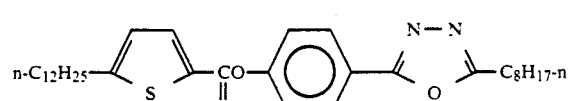 (1-29)
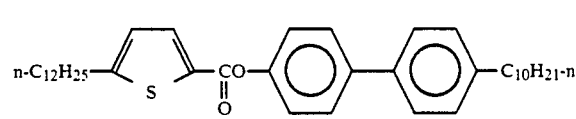 (1-30)
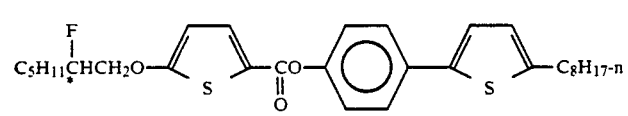 (1-31)
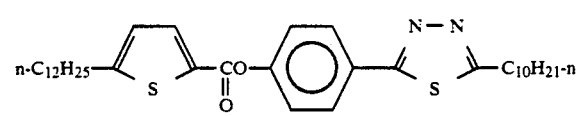 (1-32)
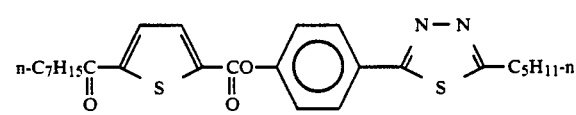 (1-33)
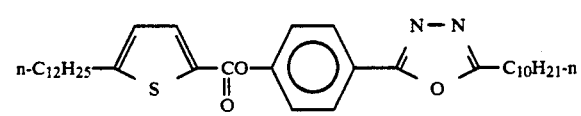 (1-34)
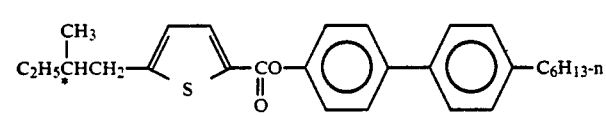 (1-35)

-continued
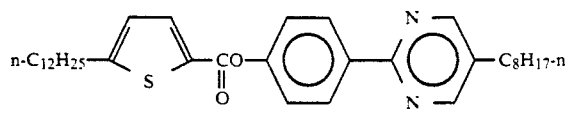
(1-36)
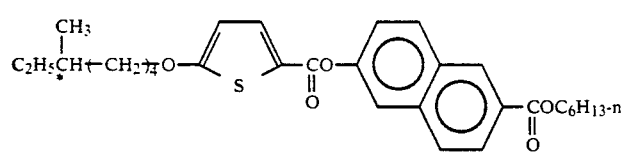
(1-37)
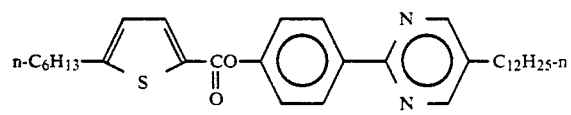
(1-38)
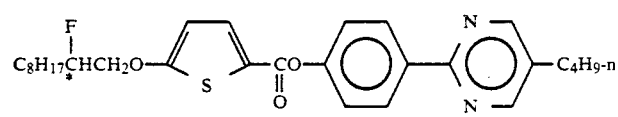
(1-39)
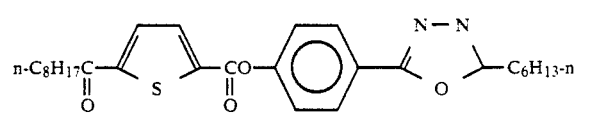
(1-40)
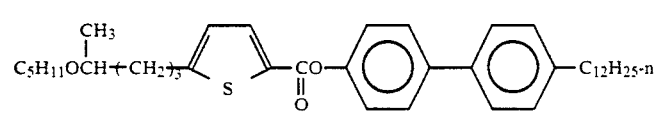
(1-41)
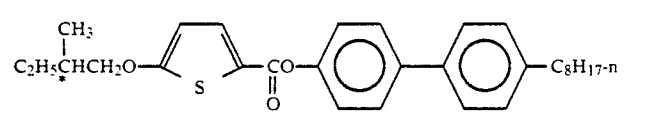
(1-42)
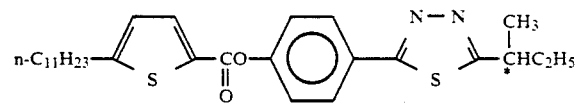
(1-43)
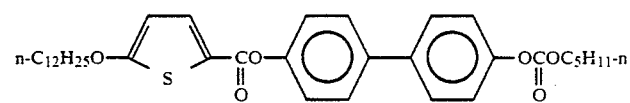
(1-44)
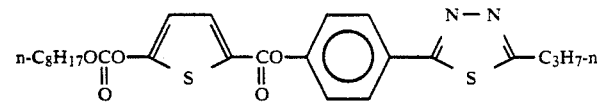
(1-45)
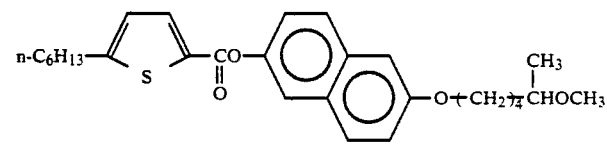
(1-46)
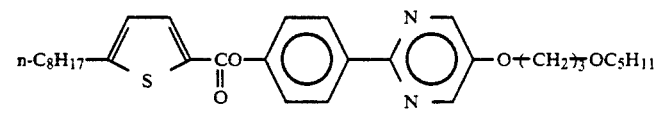
(1-47)
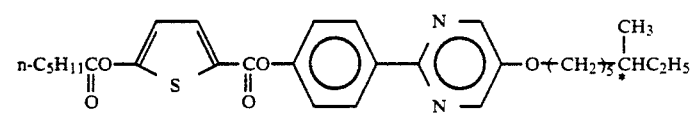
(1-48)

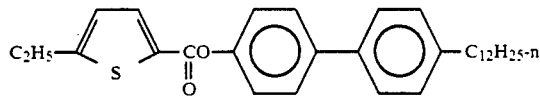 (1-49)
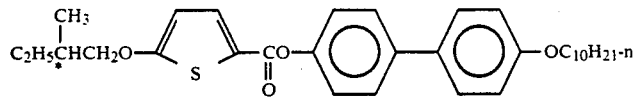 (1-50)
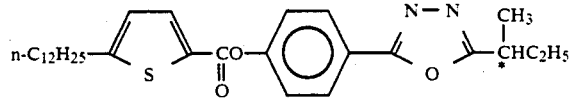 (1-51)
 (1-52)
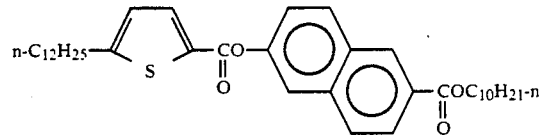 (1-53)
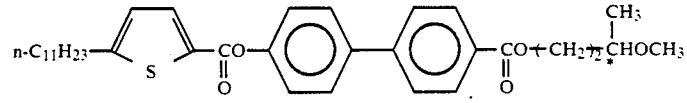 (1-54)
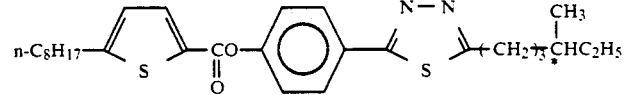 (1-55)
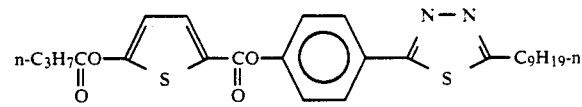 (1-56)
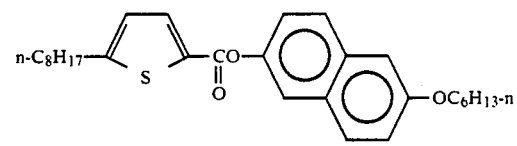 (1-57)
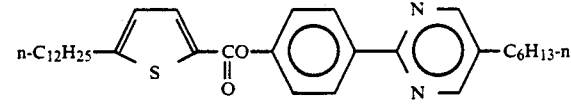 (1-58)
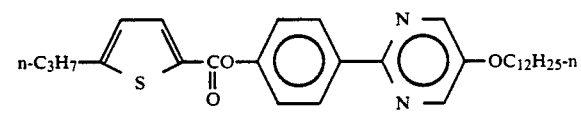 (1-59)
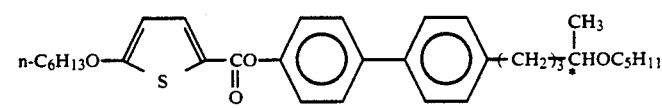 (1-60)
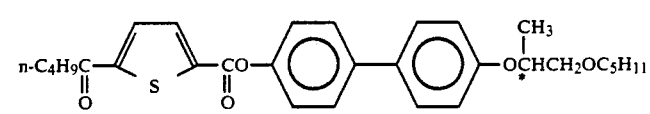 (1-61)

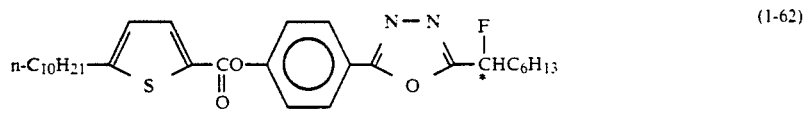 (1-62)
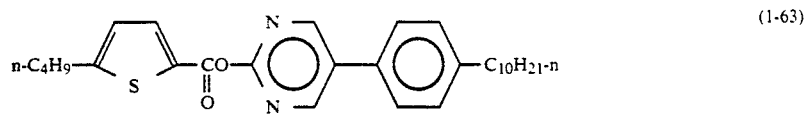 (1-63)
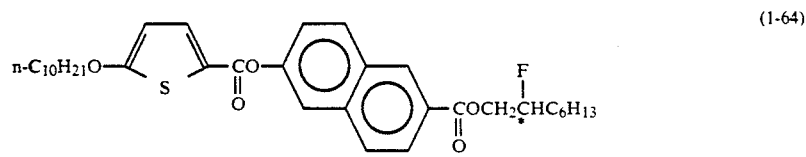 (1-64)
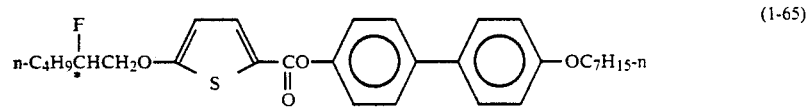 (1-65)
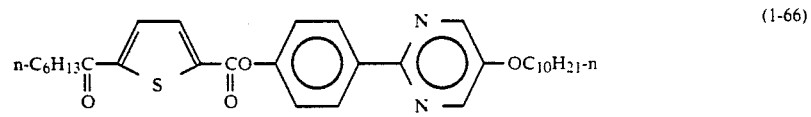 (1-66)
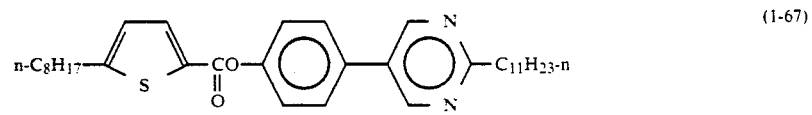 (1-67)
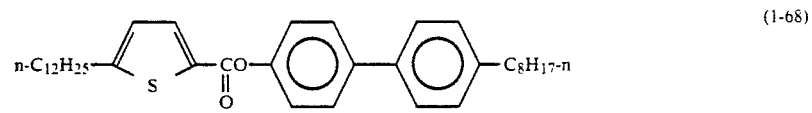 (1-68)
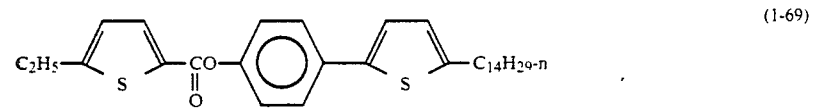 (1-69)
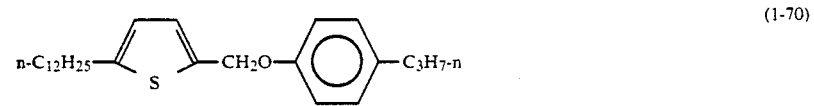 (1-70)
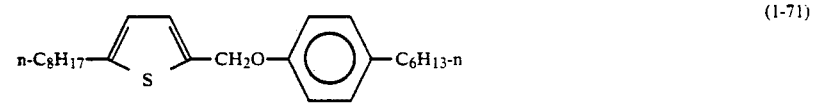 (1-71)
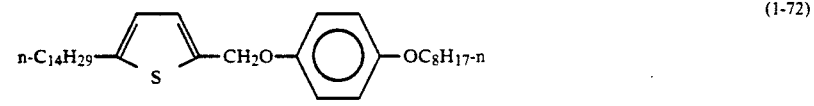 (1-72)
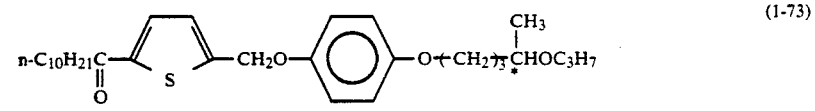 (1-73)
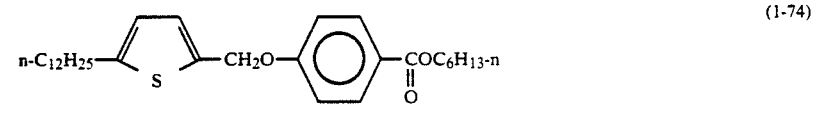 (1-74)

-continued
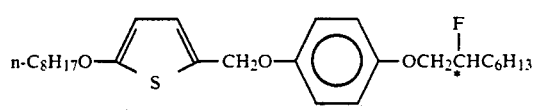 (1-75)
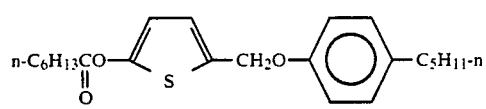 (1-76)
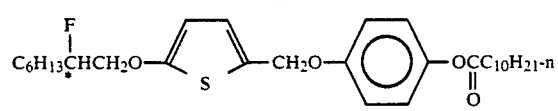 (1-77)
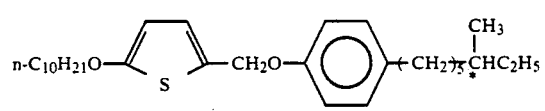 (1-78)
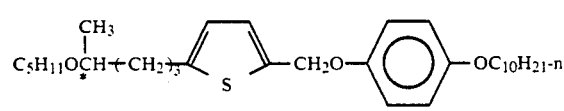 (1-79)
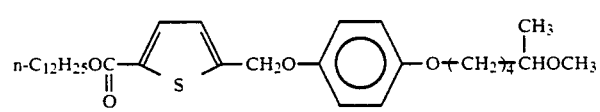 (1-80)
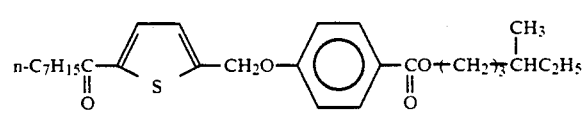 (1-81)
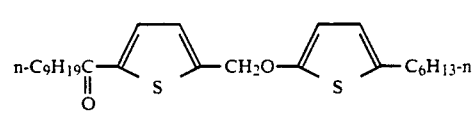 (1-82)
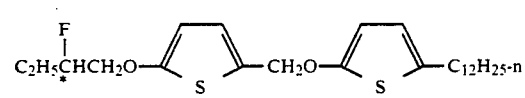 (1-83)
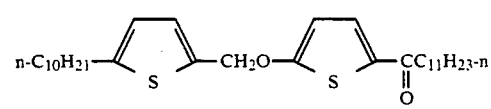 (1-84)
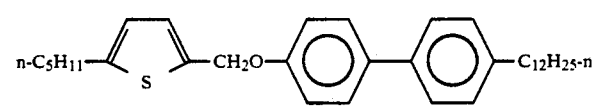 (1-85)
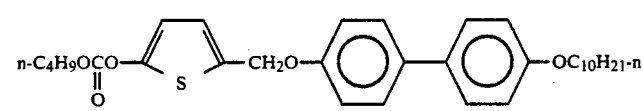 (1-86)
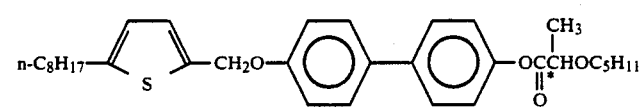 (1-87)
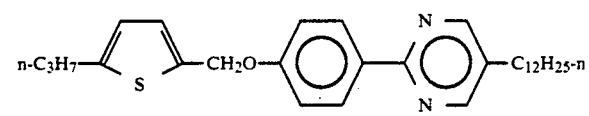 (1-88)

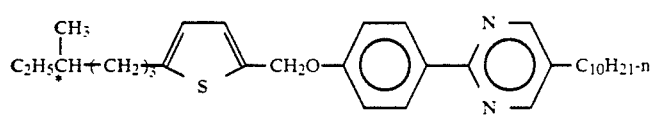 (1-89)
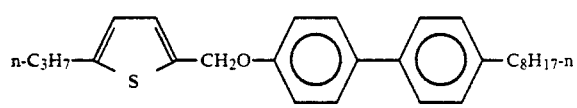 (1-90)
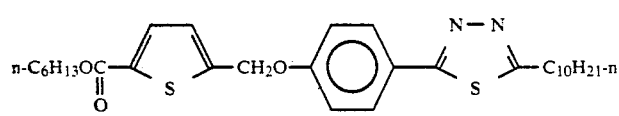 (1-91)
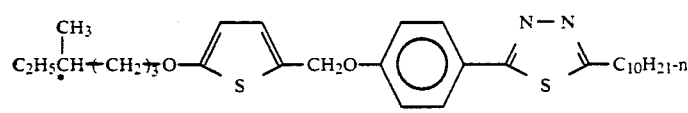 (1-92)
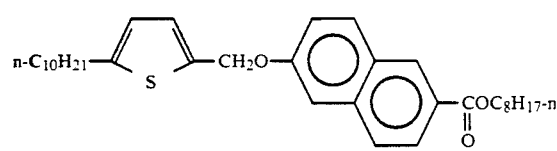 (1-93)
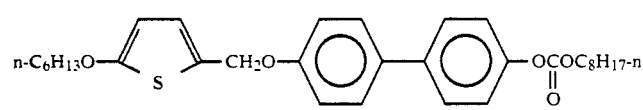 (1-94)
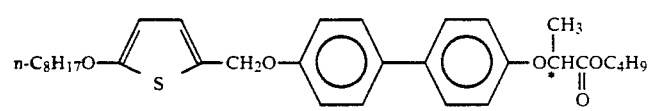 (1-95)
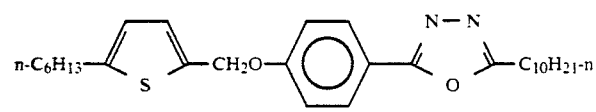 (1-96)
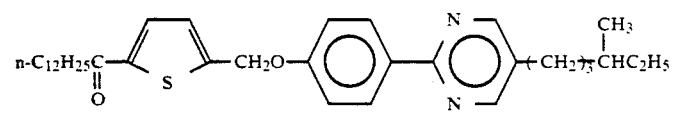 (1-97)
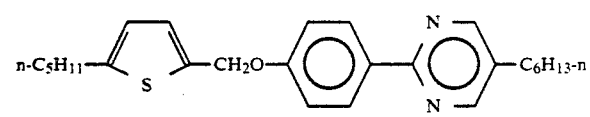 (1-98)
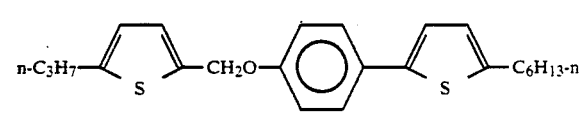 (1-99)
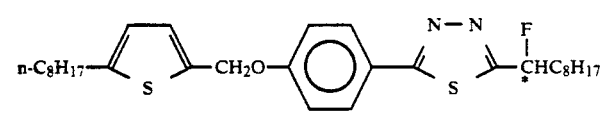 (1-100)
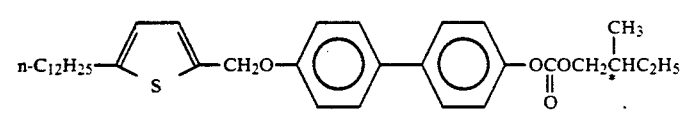 (1-101)

-continued
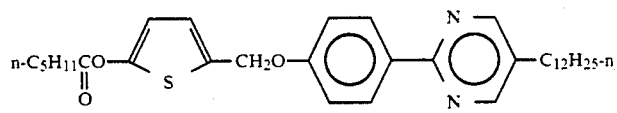
(1-102)
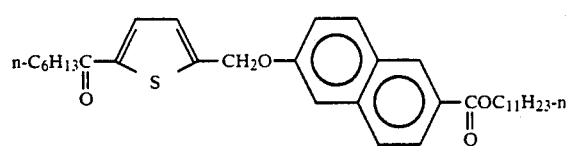
(1-103)
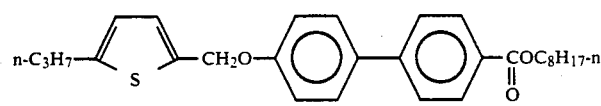
(1-104)
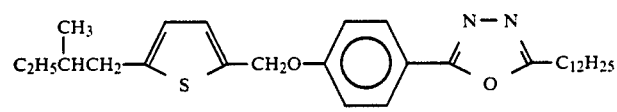
(1-105)
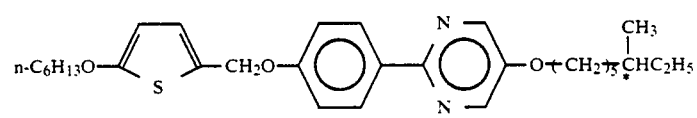
(1-106)
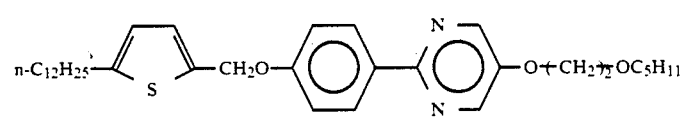
(1-107)
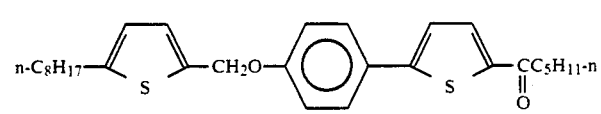
(1-108)
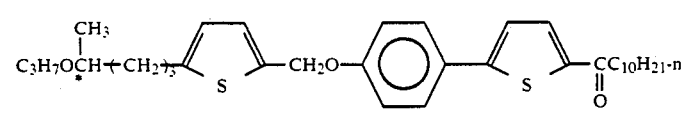
(1-109)
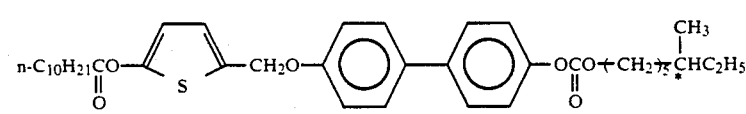
(1-110)
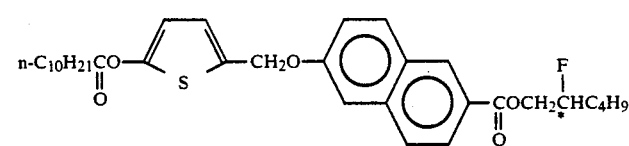
(1-111)
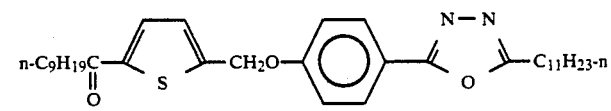
(1-112)
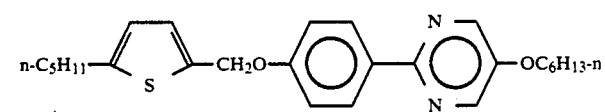
(1-113)
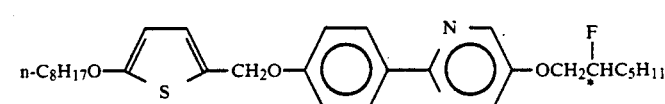
(1-114)

-continued
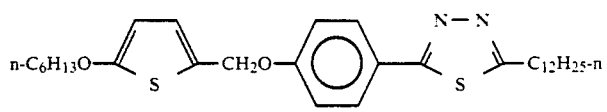 (1-115)
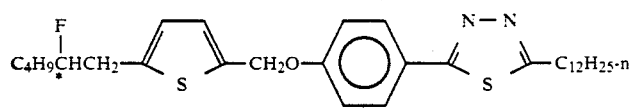 (1-116)
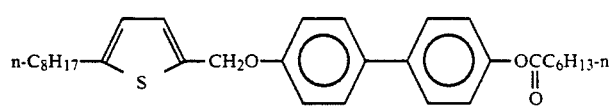 (1-117)
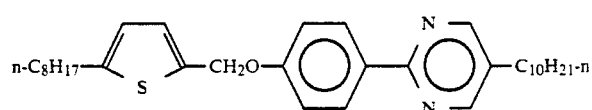 (1-118)
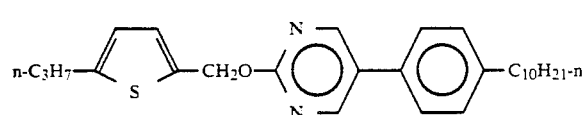 (1-119)
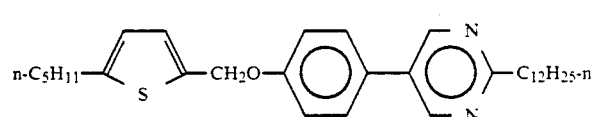 (1-120)
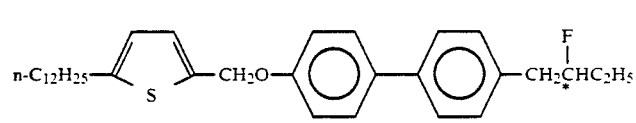 (1-121)
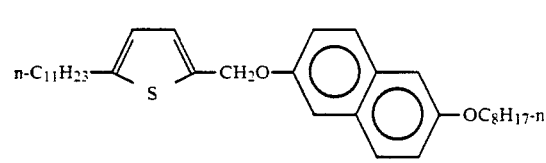 (1-122)
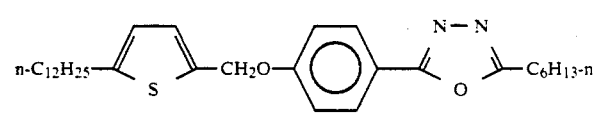 (1-123)
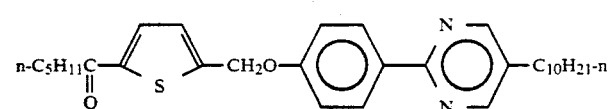 (1-124)
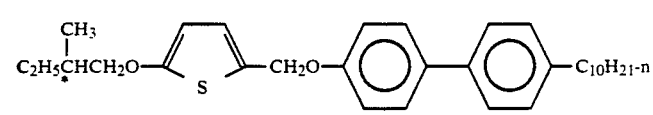 (1-125)
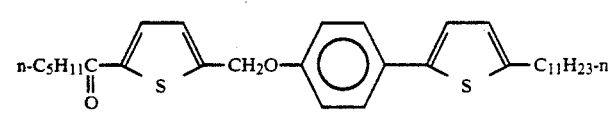 (1-126)
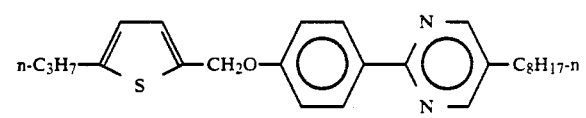 (1-127)

-continued
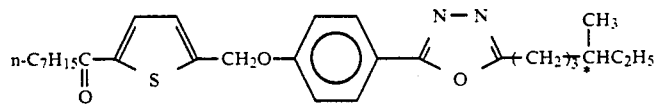 (1-128)
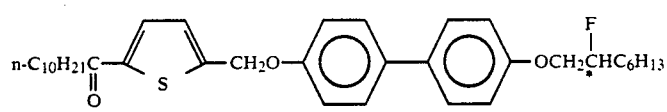 (1-129)
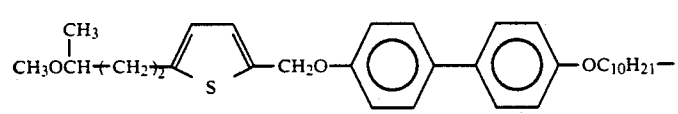 (1-130)
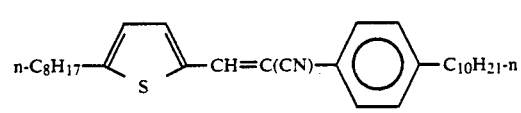 (1-131)
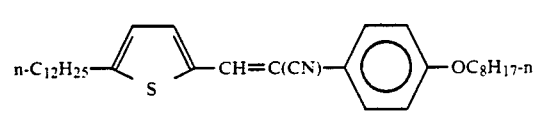 (1-132)
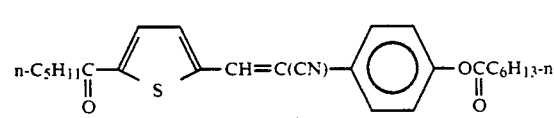 (1-133)
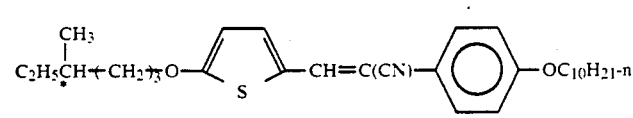 (1-134)
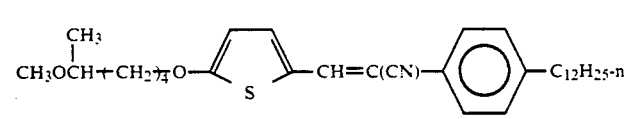 (1-135)
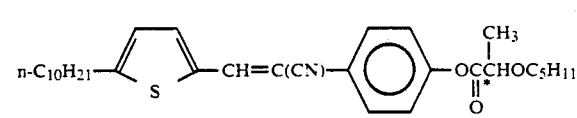 (1-136)
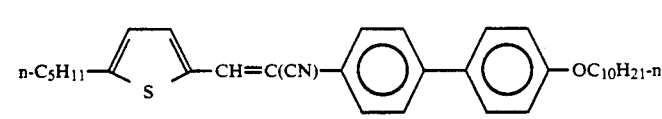 (1-137)
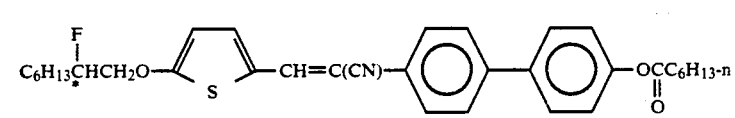 (1-138)
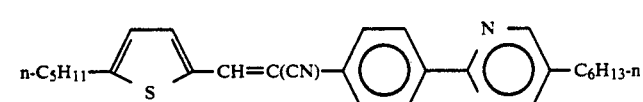 (1-139)
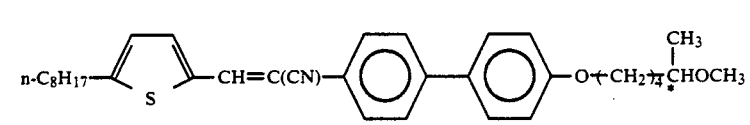 (1-140)

-continued
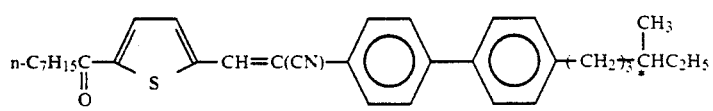 (1-141)
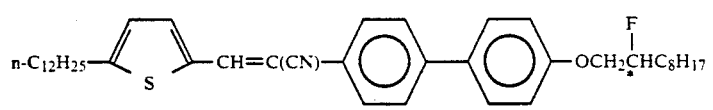 (1-142)
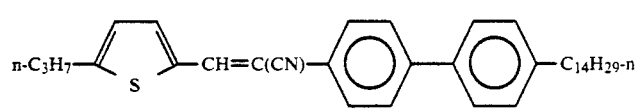 (1-143)
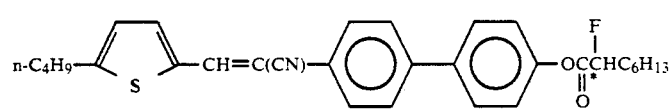 (1-144)
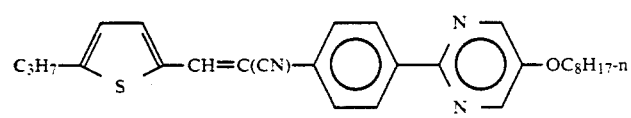 (1-145)
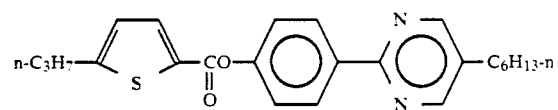 (1-146)
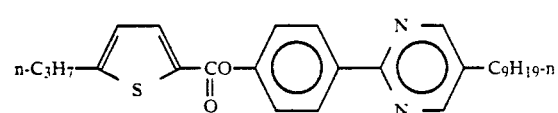 (1-147)
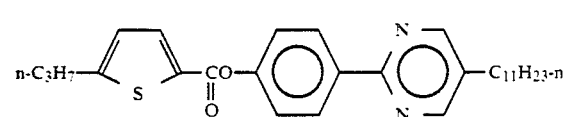 (1-148)
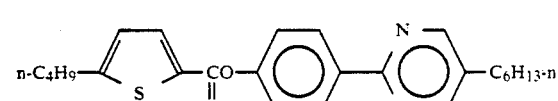 (1-149)
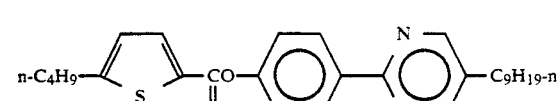 (1-150)
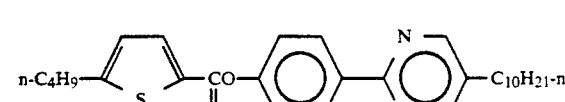 (1-151)
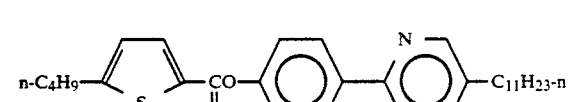 (1-152)
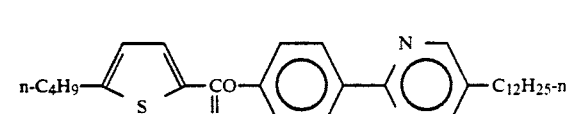 (1-153)

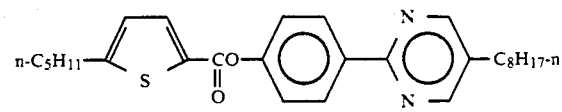 (1-154)
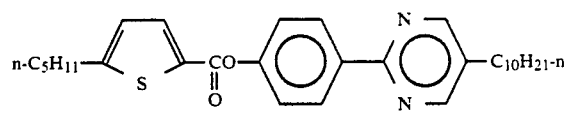 (1-155)
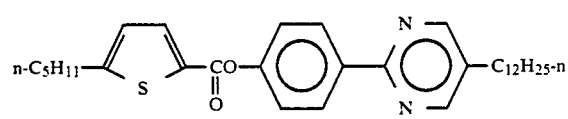 (1-156)
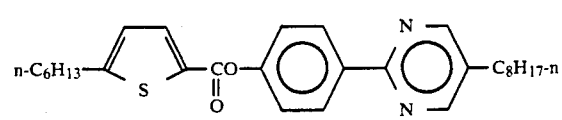 (1-157)
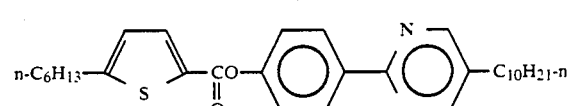 (1-158)
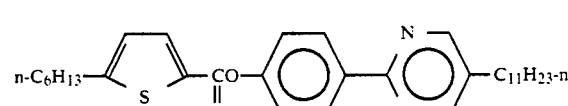 (1-159)
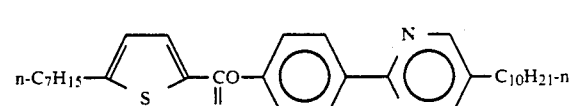 (1-160)
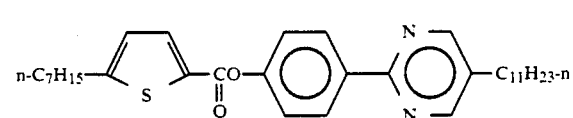 (1-161)
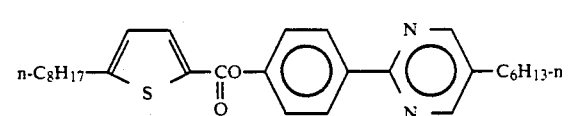 (1-162)
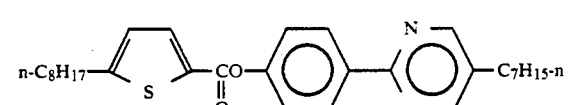 (1-163)
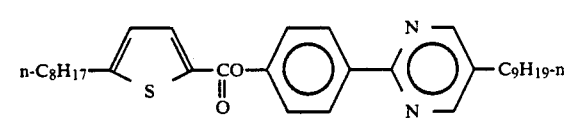 (1-164)
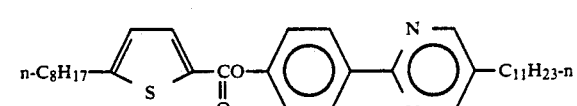 (1-165)
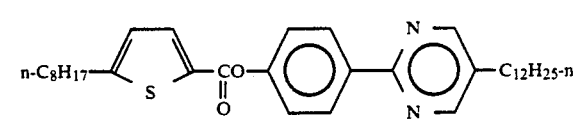 (1-166)

-continued
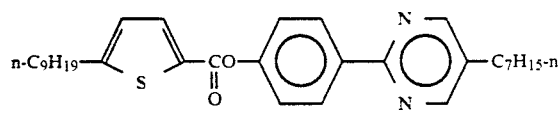 (1-167)
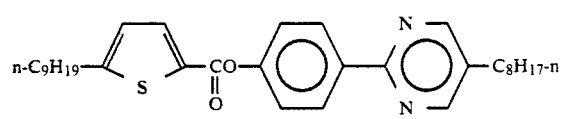 (1-168)
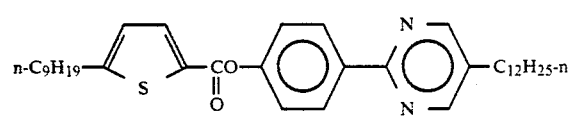 (1-169)
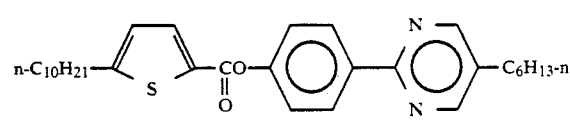 (1-170)
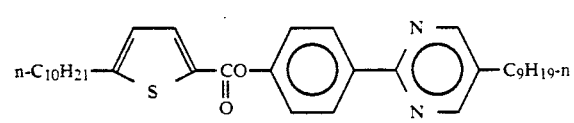 (1-171)
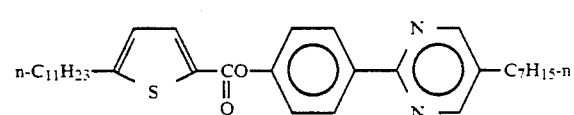 (1-172)
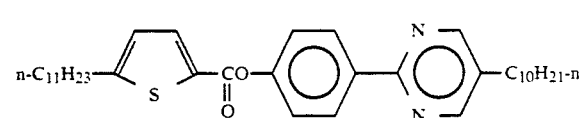 (1-173)
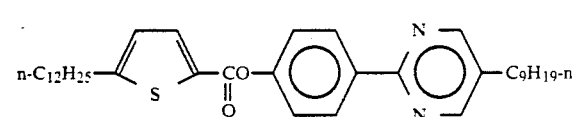 (1-174)
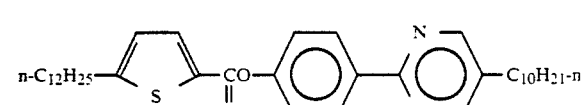 (1-175)
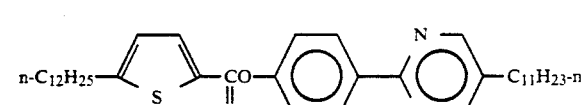 (1-176)
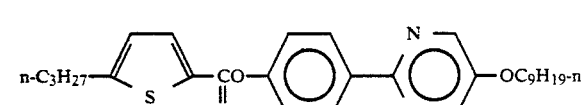 (1-177)
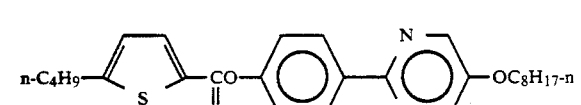 (1-178)
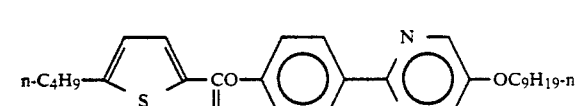 (1-179)

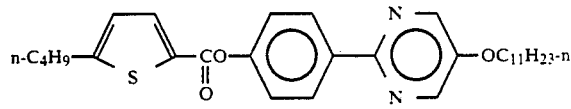
(1-180)

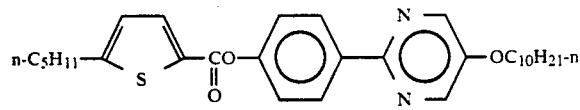
(1-181)

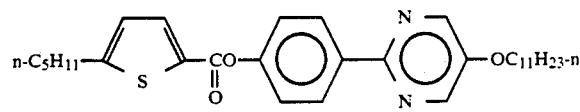
(1-182)

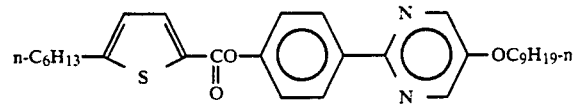
(1-183)

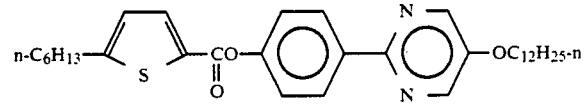
(1-184)

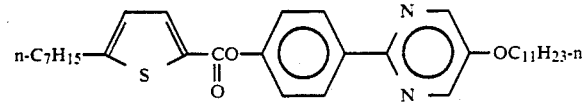
(1-185)

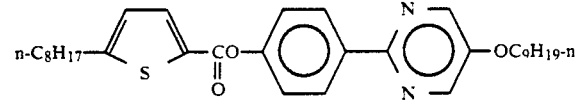
(1-186)

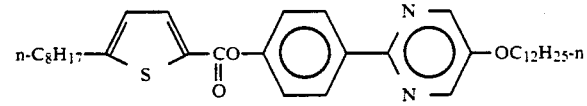
(1-187)

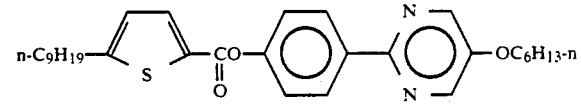
(1-188)

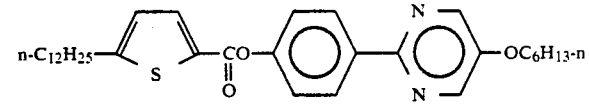
(1-189)

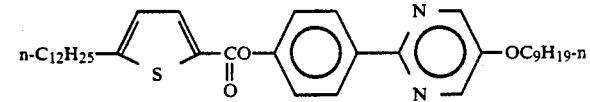
(1-190)

3. A liquid crystal composition comprising at least two mesomorphic compounds, at least one which is a mesomorphic compound according to claim 1.

4. A liquid crystal composition according to claim 3, which comprises 1-500 wt. parts of a mesomorphic compound according to claim 1 per 100 wt. parts of the remaining mesomorphic compound.

5. A liquid crystal device, comprising a pair of electrode plates and a liquid crystal composition according to claim 3 disposed between the electrode plates.

6. A liquid crystal composition according to claim 3, wherein said liquid crystal composition has a chiral smectic phase.

7. A liquid crystal devide according to claim 5, wherein the liquid crystal composition comprises 1-500 wt. parts of a mesomorphic compound according to claim 1 per 100 wt. parts of the remaining mesomorphic compound.

8. A liquid crystal device according to claim 5, wherein the liquid crystal composition has a chiral smectic phase.

* * * * *

UNITED STATES PATENT AND TRADEMARK OFFICE
CERTIFICATE OF CORRECTION

PATENT NO. : 5,116,530

DATED : May 26, 1992

INVENTOR(S) : TAKESHI TOGANO ET AL.

Page 1 of 5

It is certified that error appears in the above-identified patent and that said Letters Patent is hereby corrected as shown below:

Title page

AT [56] REFERENCES CITED

Foreign Patent Documents, insert
--62-273974  11/28/87  Japan
  2229179  09/19/90  United Kingdom--.

Other Publications, insert
--Chemical Abstracts, Vol. 109:83958m (1988), p. 733.
Chemical Abstracts, Vol. 111:15651x (1989), p. 583.
Zeitung fur Naturforschung (The Newspaper for Natural Science), Vol. 38B, No. 12 (1983) p. 1669-1677.--.
"Halfrich," should read --Helfrich,--.

COLUMN 2

Line 1, "is" should read --are--.
Line 7, "has" should read --have--.

COLUMN 11

Form 1-8, "$H_{17}$-n" should read --$H_{17}$--.

COLUMN 18

Form 1-52, "n-$C_{10}H_{21}$" should read --n-$C_{10}H_{21}\overset{\underset{\parallel}{O}}{C}$--.

COLUMN 19

Form 1-65, "n-$C_4$" should read --$C_4$--.

UNITED STATES PATENT AND TRADEMARK OFFICE
CERTIFICATE OF CORRECTION

PATENT NO. : 5,116,530

DATED : May 26, 1992

INVENTOR(S) : TAKESHI TOGANO ET AL.

It is certified that error appears in the above-identified patent and that said Letters Patent is hereby corrected as shown below:

COLUMN 29

Form 1-129, "n-$C_{10}H_{21}\underset{\underset{O}{\|}}{C}$" should read --n-$C_{10}H_{21}\underset{\underset{O}{\|}}{C}O$--.

COLUMN 40

Line 41, "another" should read --other--.

COLUMN 71

Form 209, "$C_{10}H_{21}$" should read --$OC_{10}H_{21}$--.

COLUMN 77

Form 250, " -〈◯〉- " should read -- -〈◯〉- --.

COLUMN 79

Form 264, "$H_1$" should read --$H_{11}$--.

COLUMN 83

Line 30, "and" should read --or--.
Line 42, "of which" should read --whose--.
Line 68, "i)" should read --i--.

UNITED STATES PATENT AND TRADEMARK OFFICE
CERTIFICATE OF CORRECTION

PATENT NO. : 5,116,530

DATED : May 26, 1992

INVENTOR(S) : TAKESHI TOGANO ET AL.

It is certified that error appears in the above-identified patent and that said Letters Patent is hereby corrected as shown below:

COLUMN 84

Line 53, "liter" should read --liters--.

COLUMN 85

Line 31, "liter" should read --liters--.

COLUMN 86

Line 6, "neutrality," should read --neutrally,--.
Line 46, "1-58)" should read --1-58--.
Line 47, "i)" should read --i--.

COLUMN 87

Line 27, "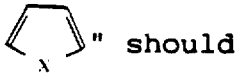" should read ----.

Line 36, "liter" should read --liters--.
Line 42, "liter" should read --liters--.
Line 57, "liter" should read --liters--.
Line 62, "liter" should read --liters--.
Line 63, "liter" should read --liters--.
Line 68, "66.7" should read --66.7%).--.

COLUMN 88

Line 61, "neutrality," should read --neutrally,--.

UNITED STATES PATENT AND TRADEMARK OFFICE
CERTIFICATE OF CORRECTION

PATENT NO. : 5,116,530

DATED : May 26, 1992

INVENTOR(S) : TAKESHI TOGANO ET AL.

It is certified that error appears in the above-identified patent and that said Letters Patent is hereby corrected as shown below:

COLUMN 92

Line 58, "(°C)). The" should read --(°C) the--.

COLUMN 93

Line 38, "second" should read --seconds--.

COLUMN 116

Line 23, "mula" should read --mulas--.
Form 1-8, "$H_{17}$-n" should read --$H_{17}$--.

COLUMN 123

Form 1-52, "n-$C_{10}H_{21}$" should read --n-$C_{10}H_{21}\underset{\underset{O}{\|}}{C}$--.

COLUMN 125

Form 1-65, "n-$C_4$" should read --$C_4$--.

COLUMN 135

Form 1-129, "n-$C_{10}H_{21}\underset{\underset{O}{\|}}{C}$" should read --n-$C_{10}H_{21}\underset{\underset{O}{\|}}{C}O$--.

UNITED STATES PATENT AND TRADEMARK OFFICE
CERTIFICATE OF CORRECTION

PATENT NO. : 5,116,530

DATED : May 26, 1992

INVENTOR(S) : TAKESHI TOGANO ET AL.

It is certified that error appears in the above-identified patent and that said Letters Patent is hereby corrected as shown below:

<u>COLUMN 144</u>

Line 60, "devide" should read --device--.

Signed and Sealed this

Nineteenth Day of October, 1993

Attest:

BRUCE LEHMAN

*Attesting Officer*   *Commissioner of Patents and Trademarks*